US012186136B2

(12) United States Patent
Gupta et al.

(10) Patent No.: US 12,186,136 B2
(45) Date of Patent: Jan. 7, 2025

(54) SYSTEMS AND METHODS FOR INTRAOPERATIVELY MEASURING ANATOMICAL ORIENTATION

(71) Applicant: Medos International Sarl, Le Locle (CH)

(72) Inventors: Saurav V. Gupta, Medway, MA (US);
Mark Hall, Bridgewater, MA (US);
Dennis Chien, West Chester, PA (US);
Michael J. O'Neil, West Barnstable, MA (US)

(73) Assignee: Medos International Sàrl, Le Locle (CH)

( * ) Notice: Subject to any disclaimer, the term of this patent is extended or adjusted under 35 U.S.C. 154(b) by 148 days.

(21) Appl. No.: 17/957,866

(22) Filed: Sep. 30, 2022

(65) Prior Publication Data
US 2023/0157782 A1  May 25, 2023

Related U.S. Application Data

(63) Continuation of application No. 15/429,566, filed on Feb. 10, 2017, now Pat. No. 11,464,596.

(Continued)

(51) Int. Cl.
*A61B 90/00* (2016.01)
*A61B 5/00* (2006.01)
(Continued)

(52) U.S. Cl.
CPC ............. *A61B 90/06* (2016.02); *A61B 5/062* (2013.01); *A61B 5/4566* (2013.01);
(Continued)

(58) Field of Classification Search
CPC ....... A61B 90/06; A61B 34/20; A61B 5/4566; A61B 2034/2048
See application file for complete search history.

(56) References Cited

U.S. PATENT DOCUMENTS 5,156,162 A  10/1992 Gerhardt
5,251,127 A  10/1993 Raab
(Continued)

FOREIGN PATENT DOCUMENTS

JP  2010233354 A  10/2010
JP  2012120648 A  6/2012
(Continued)

OTHER PUBLICATIONS

** Lafon, et al., Intraoperative three-dimensional correction during rod rotation technique. Spine (Phila Pa 1976). Mar. 1, 2009;34(5):512-9. doi: 10.1097/BRS.0b013e31819413ec.
(Continued)

*Primary Examiner* — Eric F Winakur
(74) *Attorney, Agent, or Firm* — Barnes & Thornburg LLP

(57) ABSTRACT

Systems and methods are disclosed in which changes in the position and/or orientation of an anatomical structure or of a surgical tool can be measured quantitatively during surgery. In some embodiments, the systems and methods disclosed herein can make use of inertial motion sensors to determine a position or orientation of an instrument or anatomy at different times and to calculate changes between different positions or orientations. In other embodiments, such sensors can be utilized in conjunction with imaging devices to correlate sensor position with anatomical landmarks, thereby permitting determination of absolute angular orientation of a landmark. Such systems and methods can facilitate real-time tracking of progress during a variety of procedures, including, e.g., spinal deformity correction, etc.

14 Claims, 45 Drawing Sheets

Related U.S. Application Data

(60) Provisional application No. 62/344,642, filed on Jun. 2, 2016, provisional application No. 62/294,730, filed on Feb. 12, 2016.

(51) Int. Cl.
    *A61B 5/06*          (2006.01)
    *A61B 17/00*         (2006.01)
    *A61B 17/17*         (2006.01)
    *A61B 17/56*         (2006.01)
    *A61B 17/88*         (2006.01)
    *A61B 34/00*         (2016.01)
    *A61B 34/20*         (2016.01)

(52) U.S. Cl.
    CPC .......... *A61B 17/1703* (2013.01); *A61B 34/20* (2016.02); *A61B 34/25* (2016.02); *A61B 90/08* (2016.02); *A61B 2017/00199* (2013.01); *A61B 2017/00221* (2013.01); *A61B 2017/0023* (2013.01); *A61B 2017/00367* (2013.01); *A61B 2017/00477* (2013.01); *A61B 2017/00734* (2013.01); *A61B 17/56* (2013.01); *A61B 2017/565* (2013.01); *A61B 17/8863* (2013.01); *A61B 2034/2048* (2016.02); *A61B 2034/2051* (2016.02); *A61B 2034/2065* (2016.02); *A61B 2034/252* (2016.02); *A61B 2034/254* (2016.02); *A61B 2090/067* (2016.02); *A61B 2090/0807* (2016.02); *A61B 2090/365* (2016.02); *A61B 2090/376* (2016.02); *A61B 2090/3916* (2016.02); *A61B 2090/3966* (2016.02); *A61B 2090/3983* (2016.02); *A61B 2090/3991* (2016.02); *A61B 2505/05* (2013.01); *A61B 2562/0219* (2013.01); *A61B 2562/0223* (2013.01)

(56) References Cited

U.S. PATENT DOCUMENTS

| | | |
|---|---|---|
| 5,291,901 A | 3/1994 | Graf |
| 5,305,203 A | 4/1994 | Raab |
| 5,329,933 A | 7/1994 | Graf |
| 5,748,767 A | 5/1998 | Raab |
| 5,772,610 A | 6/1998 | McGorry et al. |
| 6,015,409 A | 1/2000 | Jackson |
| 6,514,219 B1 | 2/2003 | Guimond et al. |
| 6,565,519 B2 | 5/2003 | Benesh |
| 6,711,432 B1 | 3/2004 | Krause et al. |
| 6,715,213 B2 | 4/2004 | Richter |
| 7,001,346 B2 | 2/2006 | White |
| 7,131,952 B1 | 11/2006 | Dickholtz, Sr. et al. |
| 7,139,601 B2 | 11/2006 | Bucholz et al. |
| 7,335,167 B1 | 2/2008 | Mummy |
| 7,559,931 B2 | 7/2009 | Stone |
| 7,611,522 B2 | 11/2009 | Gorek |
| 7,634,119 B2 | 12/2009 | Tsougarakis et al. |
| 7,634,306 B2 | 12/2009 | Sarin et al. |
| 7,706,000 B2 | 4/2010 | Cohen et al. |
| 7,918,887 B2 | 4/2011 | Roche |
| 7,956,887 B2 | 6/2011 | Hoeg et al. |
| 7,957,809 B2 | 6/2011 | Bourget et al. |
| 7,974,677 B2 | 7/2011 | Mire et al. |
| 7,981,115 B2 | 7/2011 | Justis et al. |
| 8,057,479 B2 | 11/2011 | Stone |
| 8,057,482 B2 | 11/2011 | Stone et al. |
| 8,128,662 B2 | 3/2012 | Altarac et al. |
| 8,167,823 B2 | 5/2012 | Nycz et al. |
| 8,348,954 B2 | 1/2013 | Carls et al. |
| 8,442,621 B2 | 5/2013 | Gorek et al. |
| 8,535,337 B2 | 9/2013 | Chang et al. |
| 8,549,888 B2 | 10/2013 | Isaacs |
| 8,565,853 B2 | 10/2013 | Frigg et al. |
| 8,690,888 B2 | 4/2014 | Stein et al. |
| 8,888,821 B2 | 11/2014 | Rezach et al. |
| 9,198,698 B1 | 12/2015 | Doose et al. |
| 9,554,411 B1 | 1/2017 | Hall et al. |
| 9,579,043 B2 | 2/2017 | Chien et al. |
| 9,993,177 B2 | 6/2018 | Chien et al. |
| 10,335,241 B2 | 7/2019 | Frasier et al. |
| 10,396,606 B2 | 8/2019 | Hall et al. |
| 10,499,996 B2 | 12/2019 | de Almeida Barreto |
| 10,714,987 B2 | 7/2020 | Hall et al. |
| 10,820,835 B2 | 11/2020 | Gupta et al. |
| 11,089,975 B2 | 8/2021 | Frasier et al. |
| 11,160,619 B2 | 11/2021 | Frasier et al. |
| 11,223,245 B2 | 1/2022 | Hall et al. |
| 11,395,604 B2 | 7/2022 | Chien et al. |
| 11,563,345 B2 | 1/2023 | Hall et al. |
| 2002/0035321 A1 | 3/2002 | Bucholz et al. |
| 2002/0120880 A1 | 8/2002 | Simon et al. |
| 2004/0152970 A1 | 8/2004 | Hunter et al. |
| 2005/0033430 A1 | 2/2005 | Powers et al. |
| 2005/0166410 A1 | 8/2005 | Richter et al. |
| 2005/0222793 A1 | 10/2005 | Lloyd et al. |
| 2005/0251026 A1 | 11/2005 | Stone |
| 2005/0262911 A1 | 12/2005 | Dankowicz et al. |
| 2006/0030771 A1 | 2/2006 | Levine et al. |
| 2006/0100508 A1 | 5/2006 | Morrison |
| 2006/0247773 A1 | 11/2006 | Stamp |
| 2007/0060799 A1 | 3/2007 | Lyon et al. |
| 2007/0106146 A1 | 5/2007 | Altmann et al. |
| 2008/0103557 A1 | 5/2008 | Davis et al. |
| 2008/0177203 A1 | 7/2008 | von Jako |
| 2008/0228195 A1 | 9/2008 | von Jako et al. |
| 2008/0266017 A1 | 10/2008 | Simon et al. |
| 2008/0269767 A1 | 10/2008 | O'Brien |
| 2008/0292161 A1 | 11/2008 | Funk et al. |
| 2009/0021752 A1 | 1/2009 | Cohen et al. |
| 2009/0171328 A1 | 7/2009 | Horvath |
| 2009/0249851 A1 | 10/2009 | Isaacs |
| 2010/0010494 A1 | 1/2010 | Quirno |
| 2010/0036384 A1 | 2/2010 | Gorek et al. |
| 2010/0063508 A1 | 3/2010 | Borja et al. |
| 2010/0069919 A1 | 3/2010 | Caris et al. |
| 2010/0087823 A1 | 4/2010 | Kondrashov |
| 2010/0100011 A1 | 4/2010 | Roche |
| 2010/0164296 A1 | 7/2010 | Kurs et al. |
| 2010/0191071 A1 | 7/2010 | Anderson et al. |
| 2010/0191088 A1 | 7/2010 | Anderson et al. |
| 2010/0204575 A1 | 8/2010 | Roche et al. |
| 2010/0204955 A1 | 8/2010 | Roche et al. |
| 2010/0312103 A1 | 12/2010 | Gorek et al. |
| 2011/0040340 A1 | 2/2011 | Miller et al. |
| 2011/0125196 A1 | 5/2011 | Quevedo et al. |
| 2011/0196455 A1 | 8/2011 | Sieracki et al. |
| 2011/0260681 A1 | 10/2011 | Guccione et al. |
| 2011/0270262 A1 | 11/2011 | Justis et al. |
| 2011/0275957 A1 | 11/2011 | Bhandari |
| 2011/0295159 A1 | 12/2011 | Shachar et al. |
| 2012/0035868 A1 | 2/2012 | Roche et al. |
| 2012/0065497 A1 | 3/2012 | Brown et al. |
| 2012/0095330 A1 | 4/2012 | Shechter et al. |
| 2012/0112690 A1 | 5/2012 | Stulen et al. |
| 2012/0123252 A1 | 5/2012 | Brunner |
| 2012/0157019 A1 | 6/2012 | Li |
| 2012/0172653 A1 | 7/2012 | Chornenky et al. |
| 2012/0203140 A1 | 8/2012 | Malchau et al. |
| 2012/0209117 A1 | 8/2012 | Mozes et al. |
| 2012/0232834 A1 | 9/2012 | Roche et al. |
| 2013/0079678 A1 | 3/2013 | Stein et al. |
| 2013/0079679 A1 | 3/2013 | Roche et al. |
| 2013/0079680 A1 | 3/2013 | Stein et al. |
| 2013/0079793 A1 | 3/2013 | Stein et al. |
| 2013/0087950 A1 | 4/2013 | Günther et al. |
| 2013/0131556 A1 | 5/2013 | Chantz |
| 2013/0135312 A1 | 5/2013 | Yang et al. |
| 2013/0165940 A1 | 6/2013 | DiSilvestro |
| 2013/0241468 A1 | 9/2013 | Moshfeghi |
| 2013/0268007 A1 | 10/2013 | Rezach et al. |
| 2013/0303225 A1 | 11/2013 | Maguire |
| 2013/0345718 A1 | 12/2013 | Crawford et al. |

(56) References Cited

U.S. PATENT DOCUMENTS

| | | |
|---|---|---|
| 2014/0031829 A1 | 1/2014 | Paradis et al. |
| 2014/0052149 A1 | 2/2014 | van der Walt et al. |
| 2014/0057572 A1 | 2/2014 | Klinghult et al. |
| 2014/0088607 A1 | 3/2014 | Recknor |
| 2014/0148808 A1 | 5/2014 | Inkpen et al. |
| 2014/0171965 A1 | 6/2014 | Loh et al. |
| 2014/0232333 A1 | 8/2014 | Kim et al. |
| 2014/0273833 A1 | 9/2014 | McCormack et al. |
| 2014/0273852 A1 | 9/2014 | McCormack et al. |
| 2014/0275940 A1 | 9/2014 | Hladio et al. |
| 2014/0275981 A1 | 9/2014 | Selover et al. |
| 2014/0276871 A1 | 9/2014 | Sherman et al. |
| 2014/0303522 A1 | 10/2014 | Akimoto et al. |
| 2014/0330112 A1 | 11/2014 | Wasielewski |
| 2015/0011874 A1 | 1/2015 | Amoako-Tuffour et al. |
| 2015/0057733 A1 | 2/2015 | Lotfi |
| 2015/0137746 A1 | 5/2015 | Lee et al. |
| 2015/0142372 A1 | 5/2015 | Singh |
| 2015/0150646 A1 | 6/2015 | Pryor et al. |
| 2015/0180263 A1 | 6/2015 | Sud et al. |
| 2015/0185846 A1 | 7/2015 | Otto et al. |
| 2015/0272694 A1 | 10/2015 | Charles |
| 2015/0305786 A1 | 10/2015 | Wehrle et al. |
| 2015/0313482 A1 | 11/2015 | Nabutovsky et al. |
| 2015/0313566 A1 | 11/2015 | Diers et al. |
| 2016/0007909 A1 | 1/2016 | Singh et al. |
| 2016/0022176 A1 | 1/2016 | Le Huec et al. |
| 2016/0058320 A1 | 3/2016 | Chien et al. |
| 2016/0058523 A1 | 3/2016 | Chien et al. |
| 2016/0191887 A1 | 6/2016 | Casas |
| 2016/0225192 A1 | 8/2016 | Jones et al. |
| 2016/0235480 A1 | 8/2016 | Scholl et al. |
| 2016/0262800 A1 | 9/2016 | Scholl et al. |
| 2016/0360997 A1 | 12/2016 | Yadav et al. |
| 2017/0143426 A1 | 5/2017 | Isaacs et al. |
| 2017/0189121 A1 | 7/2017 | Frasier et al. |
| 2017/0194820 A1 | 7/2017 | Hall et al. |
| 2017/0196507 A1 | 7/2017 | Singh et al. |
| 2017/0231709 A1 | 8/2017 | Gupta et al. |
| 2017/0348061 A1 | 12/2017 | Joshi et al. |
| 2018/0070860 A1 | 3/2018 | Gupta et al. |
| 2018/0256067 A1 | 9/2018 | Chien et al. |
| 2018/0279913 A1 | 10/2018 | Frasier et al. |
| 2019/0090955 A1 | 3/2019 | Singh et al. |
| 2019/0321109 A1 | 10/2019 | Frasier et al. |
| 2019/0341818 A1 | 11/2019 | Hall et al. |
| 2020/0297432 A1 | 9/2020 | Frasier et al. |
| 2020/0303971 A1 | 9/2020 | Hall et al. |
| 2021/0338107 A1 | 11/2021 | Frasier et al. |
| 2022/0039877 A1 | 2/2022 | Frasier et al. |
| 2022/0103024 A1 | 3/2022 | Hall et al. |
| 2022/0322959 A1 | 10/2022 | Chien et al. |

FOREIGN PATENT DOCUMENTS

| | | |
|---|---|---|
| JP | 2013544144 A | 12/2013 |
| JP | 2015502766 A | 1/2015 |
| JP | 2015109785 A | 6/2015 |
| JP | 2015213753 A | 12/2015 |
| JP | 2017510307 A | 4/2017 |
| WO | 1991003980 A1 | 4/1991 |
| WO | 1999015097 A2 | 4/1999 |
| WO | 2005077000 A2 | 8/2005 |
| WO | 2013053398 A1 | 4/2013 |
| WO | 2013169674 A1 | 11/2013 |
| WO | 2014025305 A1 | 2/2014 |
| WO | 2014063181 A1 | 5/2014 |
| WO | 2015003224 A1 | 1/2015 |
| WO | 2015114119 A1 | 8/2015 |
| WO | 2015162965 A1 | 10/2015 |
| WO | 2016032875 A1 | 3/2016 |
| WO | 2019055912 A1 | 3/2019 |

OTHER PUBLICATIONS

\** Lamecker, Hans, Thomas H. Wenckebach, and H-C. Hege. "Atlas-based 3D-shape reconstruction from X-ray images," Pattern Recognition, 2006. ICPR 2006. 18th International Conference on. vol. 1. IEEE, 2006; pp. 1-4.

\** Luc Duong, et al., Real time noninvasive assessment of external trunk geometry during surgical correction of adolescent idiopathic scoliosis. Scoliosis. Feb. 24, 2009;4:5. doi: 10.1186/1748-7161-4-5.

\** Mac-Thiong, et al., A new technique for intraoperative analysis of trunk geometry in adolescent idiopathic scoliosis. Can J Surg. Jun. 2002;45(3):219-23.

\** Mac-Thiong, et al., The effect of intraoperative traction during posterior spinal instrumentation and fusion for adolescent idiopathic scoliosis. Spine (Phila Pa 1976). Jul. 15, 2004:29(14):1549-54.

Markelj, Primoz, et al. "A review of 3D/2D registration methods for image-guided interventions," Medical image analysis 16.3 (2012): 642-661.

Mazzilli, F., et al. "Ultrasound Energy Harvesting System for Deep Implanted-Medical-Devices (IMDs)", 2012 IEEE International Symposium on Circuits and Systems (ISCAS), Seoul, 2012, pp. 2865-2868.

Sarkalkan, Nazli, Harrie Weinans, and Amir A. Zadpoor, "Statistical shape and appearance models of bones," Bone 60 (2014): 129-140.

Schumann, S., Thelen, B., Ballestra, S., Nolte, L. P., Buchler, P., & Zheng, G., "X-ray Image Calibration and Its Application to Clinical Orthopedics," Medical Engineering & Physics (2014): 36(7), 968-974.

The, B., et al., "Digital Correction of Magnification in Pelvic X-rays for Preoperative Planning of Hip Joint Replacements: Theoretical Development and Clinical Results of a New Protocol," Medical Physics 32.8 (2005): 2580-2589.

Written Opinion for Application No. PCT/US2017/050023, mailed Jan. 8, 2018 (4 Pages).

Zheng, Guoyan, et al., "A 2D/3D correspondence building method for reconstruction of a patient-specific 3D bone surface model using point distribution models and calibrated X-ray images," Medical image analysis 13.6 (2009): 883-899.

State A - Zero at starting location

State B - Measurement of the angle at ending location

State C - Zero at new starting location

State D - Measurement at new ending location

State E - Reset everything to zero to measure new angle

Press these two buttons to reset

State A — Zero's the angle for the 1st measurement 136a

State B — Measures the angle $\theta_1^\circ$ for 1st measurement 136b

Section thru X Plane

State A — Zero's the angle for the 1st measurement in orthogonal plane 136a

State B — Measures the angle $\phi_1^\circ$ in the orthogonal plane 136b

Section thru Y Plane

[1] Align reference on instrument to the projection plane, press button

[2] Align handle to first reference point and press button

[3] Align handle to second reference point and press button

[5] Redefine projection plane

[6] Re-align handle to first reference point and press button

[7] Re-align handle to second reference point and press button

[8] Final data displayed

[1] Align reference on instrument to the projection plane, press button

Sensor module on top of instrument handle

[2] Align handle to first reference point and press button

[3] Align handle to second reference point and press button

[4] Angle between both points projected on plane displayed

5 Make new measurements or press both buttons to save angle

6 After subsequent measurements the saved data can be recalled by pressing both buttons

[5] Redefine projection plane

[6] Re-align handle to first reference point and press putton

[7] Re-align handle to second reference point and press button

[8] Final data displayed

[1] Align reference on instrument to the projection plane, press button

[2] Align handle to first reference point and press button

[3] Align handle to second reference point and press button

[4] Final data displayed

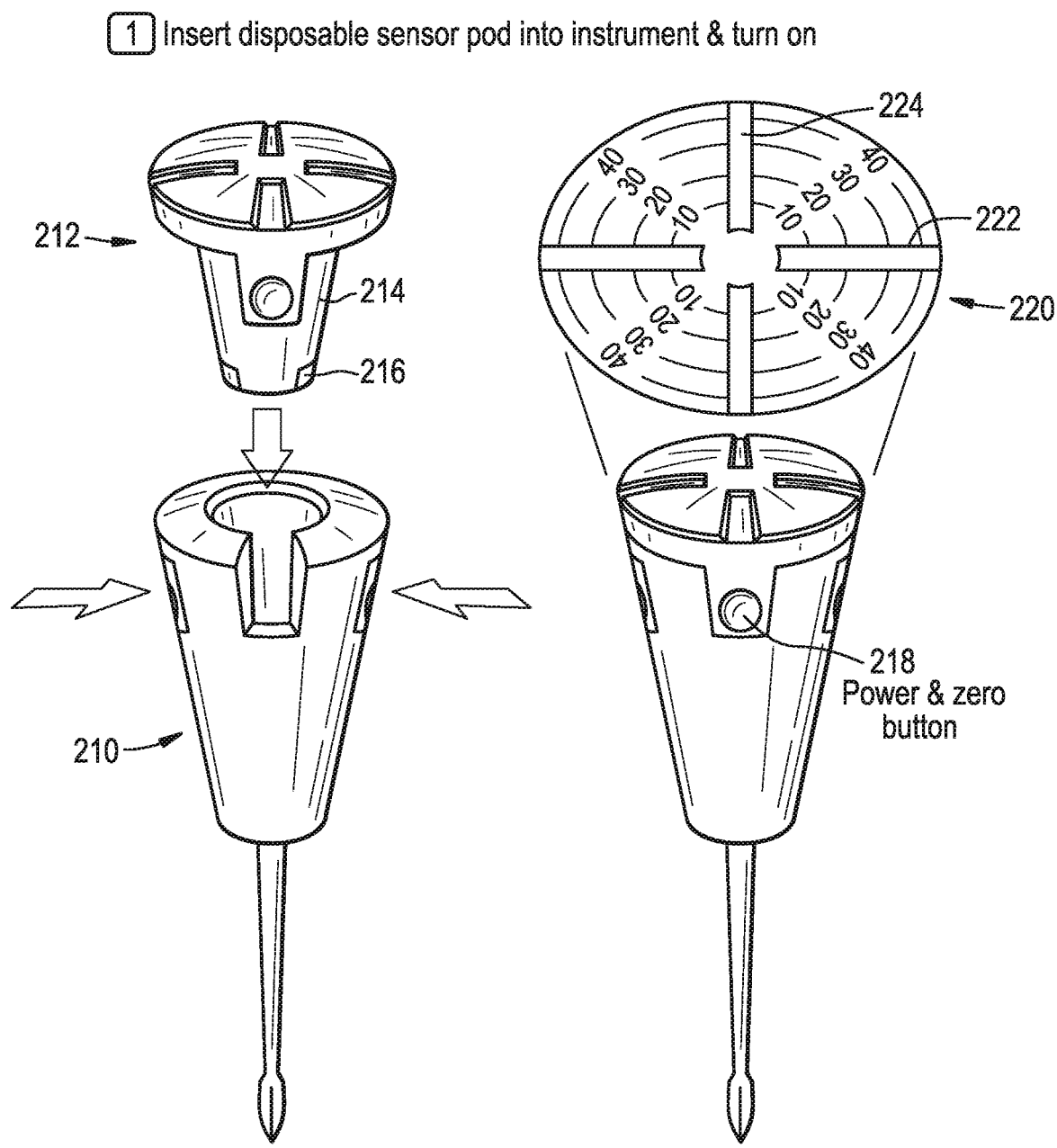

FIG. 20B
☐2 Initial angle shown relative to gravity
FIG. 20C
☐3 Press zero button
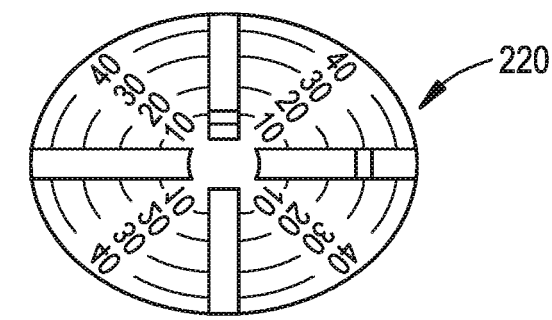
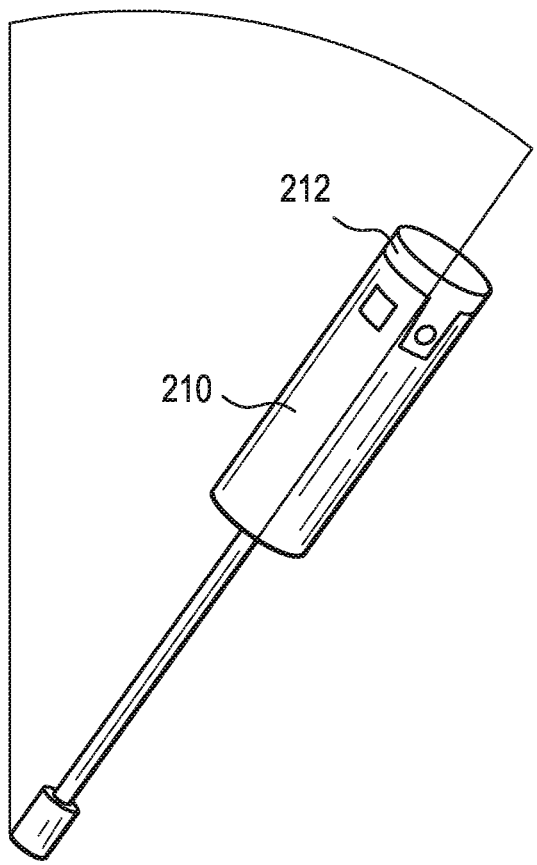
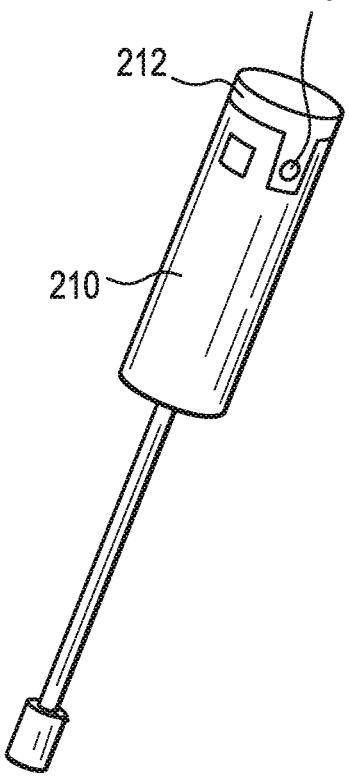

[3] Angles shown relative to zero position

1. Find pedicle trajectory, press button

2. Handle displays mirror image trajectory and flashes when lined up

☐ French Rod-Bending

TK, thoracic kyphosis; LLA, lumbar lordotic angle; SVA, sagittal vertical axis;
SS, sacral slope; PT, pelvic tilt; PI, pelvic incidence.

set sagittal plane sensor aside

A Option - fluoro images captured wirelessly

B Option - fluoro images captured via camera

Touch screen interface

Rod bending

Derotation

Osteotomy closure

SYSTEMS AND METHODS FOR INTRAOPERATIVELY MEASURING ANATOMICAL ORIENTATION

CROSS-REFERENCE TO RELATED APPLICATIONS

This application is a continuation of U.S. application Ser. No. 15/429,566, filed Feb. 10, 2017, and entitled "Systems And Methods For Intraoperatively Measuring Anatomical Orientation," and now issued as U.S. Pat. No. 11,464,596. U.S. application Ser. No. 15/429,566 claims the benefit of U.S. Provisional Application No. 62/294,730, filed Feb. 12, 2016 and entitled "Systems And Methods For Intraoperatively Measuring Anatomical Orientation," as well as U.S. Provisional Application No. 62/344,642, filed Jun. 2, 2016 and entitled "Systems And Methods For Intraoperatively Measuring Anatomical Orientation." Each of these applications is hereby incorporated by reference in its entirety.

FIELD

The present disclosure is related to systems and methods for measuring anatomical position and/or orientation. In some embodiments, systems and methods quantitatively measure changes in the position and/or orientation of a portion of a patient's anatomy with respect to another portion of the patient's anatomy during surgery.

BACKGROUND

Many surgical procedures require a surgeon to intraoperatively assess changes in the position or orientation of one or more portions of a patient's anatomy. However, even in open surgeries, there can be obstructions that prevent a surgeon from viewing relevant anatomy at a surgical site, e.g., blood, adjacent soft tissue, etc. Traditional surgical procedures use imaging techniques, such as CT-scans, x-rays, etc., to pre-operatively plan for a desired anatomical correction and then to post-operatively assess whether the desired anatomical correction has been achieved. Viewing the anatomical changes intraoperatively using such imaging techniques can be difficult, however, as it may require interruption of the surgery. Also, many imaging techniques only provide snapshots illustrating progressive changes in a qualitative manner, but do not provide data of changes as they occur in real-time. A further limitation of such imaging techniques is that they may only provide qualitative data, thus requiring a surgeon to make a subjective assessment of when a desired anatomical orientation has been achieved. Such imaging techniques also expose the patient and the operating room staff to potentially-harmful radiation.

During a traditional pedicle subtraction osteotomy, surgeons remove bone from a vertebra of a patient suffering from a spinal deformity to correct spinal curvature. To intraoperatively determine when the appropriate amount of bone has been removed, the surgeon must be able to accurately assess the amount of correction that has been achieved at a given time. Traditionally, to make this assessment, the surgeon must step back from the surgical procedure while an imaging device is brought in and positioned to view the curvature of the spine. However, this provides only a subjective measure of angular correction and involves an interruption in the surgical procedure, adding time and inconvenience. Often times, this results in sub-optimal patient outcomes and repeat surgeries due to over- or under-correction of the deformity.

Thus, there is a need for improved systems and methods for intraoperatively measuring anatomical position and/or orientation.

SUMMARY

Systems and methods are disclosed in which changes in the position and/or orientation of an anatomical structure or of a surgical tool can be measured quantitatively during surgery. In some embodiments, a surgical electronic module can be configured to attach to a portion of a patient's anatomy and/or to a surgical device, to continually detect changes in a position and/or orientation of the patient's anatomy and/or the surgical device during surgery, and to communicate the changes to a user. Where the surgical device is attached to a portion of a patient's anatomy and/or is used to manipulate the patient's anatomy, the surgical electronic module can detect changes in the position and/or orientation of said anatomy. In embodiments where more than one module is used during surgery, the modules can continually detect changes in their positions and/or orientations relative to one another, which correspond to changes in relative positions and/or orientations of portions of the patient's anatomy and/or the surgical devices to which the modules are attached.

In one exemplary embodiment, a surgical electronic module is provided that includes a housing having one or more engagement features that are configured to removably attach the housing to a surgical device, a sensor, a processor, and a display. The sensor can be disposed in the housing and can be configured to detect a position or orientation of the module with respect to the earth. The processor can be coupled to the sensor and can be configured to calculate a change in position or orientation of the surgical device with respect to one or more reference points when the surgical device is attached to the module, based on the position or orientation detected by the sensor. The display can be configured to display the change calculated by the processor to thereby assist a user in assessing changes in position or orientation of anatomy coupled to or manipulated by the surgical device. In some embodiments, the display can be disposed on the housing.

In some embodiments, the surgical electronic module can include additional components. By way of non-limiting example, the surgical electronic module can further include a reset mechanism that, when actuated, sets an initial position or orientation of the module to be used in calculating the change in the position or orientation of the surgical device. Additionally or alternatively, the surgical electronic module can include a memory configured to store at least one of the position or orientation detected by the sensor and the change calculated by the processor. In still further embodiments, the surgical electronic module can include a communications interface configured to send the position or orientation detected by the sensor to an external device and to receive a position or orientation of the one or more reference points from the external device. The external device can be a second surgical electronic module.

In some embodiments, the one or more reference points can include a second surgical electronic module. In some embodiments, the sensor can be configured to detect the position or orientation at predetermined time intervals and/or the processor can be configured to calculate the change at the predetermined time intervals. The processor can further be configured to calculate first, second, and/or third derivatives of the position or orientation of the surgical device. In still further embodiments, the one or more engagement features can be configured to identify an aspect of the surgical device when the surgical device is attached to the module.

In another aspect, a surgical method is provided for measuring a change in anatomical position or orientation. The method can involve detecting an absolute angle of a first electronic module attached to a first surgical device by a sensor of the first electronic module, with the first surgical device being operatively coupled with a first portion of a patient's anatomy and detecting an absolute angle of a second electronic module attached to a second surgical device by a sensor of the second electronic module, with the second surgical device being operatively coupled with a second portion of the patient's anatomy. The method can also include calculating by a processor of at least one of the first and second electronic modules a change in an angle of the first electronic module with respect to the second electronic module multiple times during a surgery to determine a change in an angle of the first surgical device with respect to the second surgical device. The method can further include conveying to a user the change in the angle of the first surgical device with respect to the second surgical device to thereby assist the user in determining a change in an angle of the first portion of the patient's anatomy with respect to the second portion of the patient's anatomy. In some embodiments, the change in the angle of the first surgical device with respect to the second surgical device is conveyed to the user on a display of at least one of the first electronic module and the second electronic module.

In some embodiments, the method can further include actuating reset mechanisms of the first and second electronic modules to set an initial angle of the first module with respect to the second module. The initial angle can be used in calculating the change in the angle of the modules relative to one another. The calculating and the conveying steps can be repeated until a target position or orientation of the first surgical device with respect to the second surgical device has been reached. In such embodiments, the method can further include alerting the user when the target position or orientation has been reached. In still further embodiments, the method can include calculating a rate of the change in the angle of the first surgical device with respect to the second surgical device.

In some embodiments, the first and second portions of the patient's anatomy are first and second vertebra on opposite sides of an osteotomy site. When the first portion of the patient's anatomy is a first vertebra and the first surgical device is a first bone screw implanted in the first vertebra, the method can further include attaching the first electronic module to the first bone screw. Additionally, when the second portion of the patient's anatomy is a second vertebra disposed opposite an osteotomy site from the first vertebra and the second surgical device is a second bone screw implanted in the second vertebra, the method can further include attaching the second electronic module to the second bone screw. In such embodiments, the method can also include locking a spinal rod to the first and second bone screws after a target position or orientation of the first vertebra with respect to the second vertebra has been reached.

In yet another aspect, a surgical method is provided for guiding a surgical instrument. The method can include detecting an orientation of a first electronic module that is attached to the surgical instrument by a sensor of the first electronic module, detecting a position of the first electronic module via communications between the first electronic module and at least two electronic modules attached to at least two surgical devices, calculating by a processor of the first electronic module a change in the orientation of the surgical instrument and a change in the position of the surgical instrument over time, and conveying to a user the change in the orientation and the position of the surgical instrument to thereby assist the user in guiding the surgical instrument during surgery. In some embodiments, the change in the position and the orientation of the surgical instrument is conveyed to the user on a display of the first electronic module. In some embodiments, the at least two surgical devices do not move with respect to a patient's anatomy while the user is guiding the surgical instrument.

In another aspect, a surgical electronic module is provided that can include a housing, a sensor disposed in the housing and configured to detect a position or orientation of the module, an input disposed on an outer surface of the housing, and a processor coupled to the sensor and configured to record the position or orientation of the module in response to instruction from the input. The processor can be further configured to simultaneously calculate a change in position or orientation of the module in two orthogonal planes with respect to a reference point based on the position or orientation detected by the sensor. The module can also include a display configured to display the change calculated by the processor to thereby assist a user in assessing changes in position or orientation of anatomy coupled to the module.

Any of a variety of additional features or substitutions are possible. For example, in some embodiments the housing can include an engagement feature configured to removably attach the housing to a surgical instrument. In other embodiments, however, the module can be integrally formed in a surgical instrument. Any of a variety of surgical instruments can be utilized, including, for example, any of an osteotome, a chisel, a deformity correction instrument, a probe, an awl, a drill, a tap, and a gearshift.

The sensor included in the electronic module can be an inertial motion sensor that can include any of an accelerometer, a gyroscope, and a magnetometer. In some embodiments, for example, the sensor can be a 9-axis inertial motion sensor which can include an accelerometer, a gyroscope, and a magnetometer. In other embodiments, alternative sensors can be utilized that can include a subset of these components, e.g., an inertial motion sensor including solely a 3-axis accelerometer, a "10-axis" sensor including an altimeter, an "11-axis" sensor including a temperature sensor, etc. Moreover, in some embodiments a sensor can be configured to utilize only a subset of its available components, e.g., a 9-axis sensor having an accelerometer, a gyroscope, and a magnetometer that can be configured to make use of, for example, only the accelerometer and the gyroscope (thereby forming an effective "6-axis" sensor). In other embodiments various other sensors can be employed that can provide position and/or orientation information.

The input can have a variety of forms. In some embodiments, for example, the input can be a single button. In other embodiments, the input can include a plurality of buttons (e.g., 4 buttons, 5 buttons, etc.). In still other embodiments, button alternatives can be utilized, including switches, pressure sensitive sensors, etc. The buttons, switches, etc. can each be selectively lighted in some embodiments to provide feedback to a user and/or to prompt a user for input (e.g., a first button can light up to prompt recording of a first position or orientation, and a second button can light up to prompt recording of a second position or orientation).

As described in more detail below, in some embodiments the electronic module can be configured to calculate changes between two positions and project those changes into a previously-defined orthogonal reference planes. In some embodiments, the module can include a reference plane alignment feature for defining the two orthogonal planes. The reference plane alignment feature can be an extended ridge, protrusion, or other feature formed on the housing in some embodiments.

In one aspect, a surgical method is provided that can include positioning a surgical instrument in a first position or orientation relative to anatomy, receiving instruction from an input and recording the first position or orientation using a sensor coupled to the surgical instrument and configured to detect a position or orientation thereof, positioning the surgical instrument in a second position or orientation relative to anatomy, receiving instruction from the input and recording the second position or orientation using the sensor, calculating changes in position or orientation between the first and second positions or orientations in two orthogonal planes, and displaying the changes in position or orientation in the two orthogonal planes using a display coupled to the surgical instrument.

As with the module described above, a number of variations and additions are possible. For example, in some embodiments the method can further include coupling a surgical electronic module including the sensor and the display to the surgical instrument, whereas in other embodiments the sensor and the display can be integrally formed in the surgical instrument. Any of a variety of surgical instruments can be utilized and, in some embodiments, the surgical instrument can be any of an osteotome, a chisel, a deformity correction instrument, a probe, an awl, a drill, a tap, and a gearshift.

As noted above, in some embodiments the input can be a single button, while in other embodiments the input can be a plurality of buttons. In still other embodiments, any of a variety of button alternatives, such as switches, pressure-sensitive sensors, etc., can be utilized. In an embodiment in which a plurality of buttons is utilized, the method can further include resetting any of the recorded first and second positions or orientations in response to simultaneous depression of more than one button.

In some embodiments, the method can further include positioning the surgical instrument in a third position or orientation relative to anatomy, receiving instruction from the input and recording the third position or orientation using the sensor, positioning the surgical instrument in a fourth position or orientation relative to anatomy, and receiving instruction from the input and recording the fourth position or orientation using the sensor. The method can also include calculating changes in position or orientation between the third and fourth positions or orientations as projected onto a first plane defined between the first and second positions or orientations and a second plane orthogonal to the first plane, and displaying the changes in position or orientation between the third and fourth positions or orientations using the display. In this manner, the first and second positions of the surgical instrument recorded by the sensor can be used to define a first reference plane and a second reference plane orthogonal thereto, and position/orientation changes between third and fourth positions can be projected onto the two reference planes.

In another aspect, a method for performing bone or tissue correction or manipulation is provided that can include coupling first and second sensors to respective first and second portions of a patient's anatomy, and actuating an imaging device to capture an image of the first and second portions of the anatomy with the first and second sensors coupled thereto. The method can further include utilizing the image of the first and second portions of the anatomy in a simulated environment to identify a desired anatomical landmark with respect to each of the attached sensors, as well as, using a processor, determining a compensatory angle between each sensor and its respective anatomical landmark, and utilizing the compensatory angles and a measured angle between the first and second sensors to calculate an absolute anatomical angular orientation of the landmarks.

In some embodiments, coupling the first and second sensors can include implanting the first and second sensors in the patient. Further, in some embodiments the first and second sensors can be percutaneously implanted in the patient. As explained in more detail below, in some embodiments a mount can be employed to achieve percutaneous implantation of a sensor.

In some embodiments, the absolute angular orientation can be calculated in real-time or substantially in real-time, thereby providing a constant update to a surgeon or other user without the need to interrupt a procedure. In still other embodiments, the method can further include coupling a reference plane sensor to a patient's anatomy to define a reference plane in which angular orientation can be measured. In some embodiments, the reference plane sensor can be used to define a first reference plane and a second reference plane orthogonal to the first reference plane.

In another aspect, a method of measuring an absolute spinal angle is provided that can include coupling first and second sensors to respective first and second portions of a patient's spine, as well as capturing at least one image of the first and second sensors and the patient's spine using an imaging device. The method can further include identifying in the at least one captured image first and second vertebral endplates that define the absolute spinal angle to be measured, calculating, by a processor, a first compensation angle between the first endplate and the first sensor in the at least one captured image, and calculating, by a processor, a second compensation angle between the second endplate and the second sensor in the at least one captured image. The method can also include obtaining a relative angle measured between the first and second sensors, adjusting, by a processor, the relative angle based on the first and second compensation angles to calculate the absolute spinal angle, and communicating the absolute spinal angle to a user.

In some embodiments, the absolute spinal angle can be calculated and communicated to the user in real-time or substantially in real-time. Further, in some embodiments the absolute spinal angle can be at least one of lumbar lordosis and thoracic kyphosis.

In certain embodiments, communicating the absolute spinal angle can include displaying the angle on an electronic display. In other embodiments, different communication methods can be employed, such as audio communication through a speaker, or combinations of audio, visual, and tactile feedback. Further, in some embodiments, identifying the endplates can include interacting with a graphical user interface that displays the at least one captured image to select the endplates with an input device.

As with the method described above, in some embodiments coupling the first and second sensors can include implanting the first and second sensors in the patient. Moreover, in certain embodiments the first and second sensors can be percutaneously implanted in the patient. This can be accomplished in some embodiments using a percutaneous mount configured to receive a sensor and to extend into a patient.

In still another aspect, a surgical system is provided that can include a first sensor configured to couple to a first portion of a patient's anatomy, a second sensor configured to couple a second portion of the patient's anatomy, and an imaging device configured to capture an image of the patient's anatomy and the first and second sensors. The system can further include a processor configured to receive via an input identification of a desired anatomical landmark with respect to one of the first and second sensors, and determine a compensatory angle between each sensor and its respective anatomical landmark, wherein the processor is further configured to calculate an absolute anatomical angular orientation of the landmarks utilizing the compensatory angles and a measured angle between the first and second sensors. The system can further include a display configured to display the captured image and calculated absolute anatomical angular orientation of the landmarks.

The system can include a number of additions or variations. For example, in some embodiments the system can further include a reference plane sensor configured to be coupled to the patient's anatomy to define a reference plane in which angular orientation can be measured. In certain embodiments, the reference plane sensor can also define a second reference plane orthogonal to the reference plane. In some embodiments, the reference plane sensor can be direction-specific, e.g., a first end can be configured to point toward a user's head or other portion of anatomy while a second end can be configured to point toward a user's feet or other portion of anatomy. In such an embodiment, the reference plane sensor can include an orientation indicator to aid a user in aligning the reference plane sensor. An orientation indicator can be an arrow or other marking in some embodiments. In other embodiments, the reference plane sensor can be formed in the shape of a human patient such that a surgeon or other user can intuitively align the shape of the reference plane sensor with the shape of the patient during use.

In some embodiments, each of the first and second sensors can be an inertial motion sensor including any of an accelerometer, a gyroscope, and a magnetometer. For example, in some embodiments the sensor can be a 9-axis inertial motion sensor including an accelerometer, a gyroscope, and a magnetometer. In other embodiments, different inertial motion sensors can be utilized having a subset of these components. For example, in some embodiments a sensor having solely a 3-axis accelerometer can be employed, etc.

In some embodiments, each of the first and second sensors can be radiopaque to facilitate capture of the sensors by the imaging device. For example, if the imaging device is configured to capture X-ray images, radiopaque sensors can be clearly visible in the captured images.

As noted above, in some embodiments the first and second sensors can be implanted in a patient and, in certain embodiments, can be implanted percutaneously. In some embodiments, the system can further include first and second mounts configured to permit percutaneous coupling of the first and second sensors to the patient's anatomy. Each of the first and second mounts can include a needle-shaped distal portion for percutaneous insertion through a patient's skin and a proximal recess configured to receive one of the first and second sensors therewithin.

Any of the features or variations described above can be applied to any particular aspect or embodiment of the disclosure in a number of different combinations. The absence of explicit recitation of any particular combination is due solely to the avoidance of repetition in this summary.

BRIEF DESCRIPTION OF THE DRAWINGS

The invention will be more fully understood from the following detailed description taken in conjunction with the accompanying drawings, in which:

FIG. 20A is a schematic illustration of one embodiment of an electronic module configured to selectively couple to a surgical instrument;

FIG. 20B is a schematic illustration of the electronic module and surgical instrument of FIG. 20A measuring a first position or orientation relative to earth;

FIG. 20C is a schematic illustration of the electronic module and surgical instrument of FIG. 20A being zeroed at the first position or orientation;

DETAILED DESCRIPTION

Figure 1A:
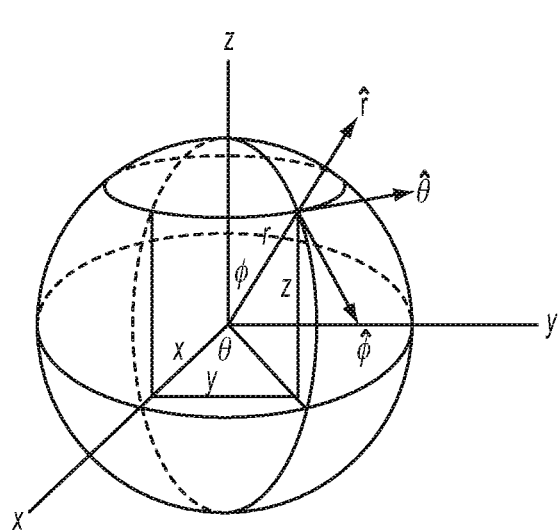
FIG. 1A is a schematic illustration of a spherical coordinate system.

Certain exemplary embodiments will now be described to provide an overall understanding of the principles of the structure, function, manufacture, and use of the devices and methods disclosed herein. One or more examples of these embodiments are illustrated in the accompanying drawings. Those of skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In the present disclosure, like-numbered components of the embodiments generally have similar features and/or purposes. Further, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the size and shape of the components with which the systems and devices are being used, the anatomy of the patient, and the methods and procedures in which the systems and devices will be used. The figures provided herein are not necessarily to scale.

Systems and methods are disclosed in which changes in a position and/or orientation of an anatomical structure or of a surgical tool can be measured quantitatively during surgery. In some embodiments, a surgical electronic module can be configured to attach to a surgical device, to continually detect changes in a position and/or orientation of the surgical device during surgery, and to communicate the changes to a user. In this way, where the surgical device is attached to a portion of a patient's anatomy and/or is used to manipulate the patient's anatomy, the surgical electronic module can detect changes in the position and/or orientation of said anatomy. In embodiments where more than one module is used during surgery, the modules can continually detect changes in their positions and/or orientations relative to one another, which correspond to changes in relative positions and/or orientations of the surgical devices to which the modules are attached. Additionally or alternatively, at least one of the modules can help to establish a reference 3D location in the operating room, particularly where the at least one of the modules is stationary. In some embodiments, the modules can include a resetting or "zeroing" function that allows a user to selectively set an initial relative position and/or orientation of the modules to zero. Subsequent changes in the relative positions and/or orientations of the modules can then be measured and displayed to the user so that the user knows when a desired change in position and/or orientation of the modules has been reached. In some embodiments, all of the components necessary for detecting, calculating, and/or communicating positional information (i.e., position and/or orientation) are contained within the module itself, thus eliminating the need for an external base station or other additional bulky equipment. By thus providing a means for quantitatively measuring changes in anatomical orientation in real-time during surgery, exemplary systems and methods provided herein can enhance the accuracy of the surgery and reduce or eliminate the need for intraoperative imaging, thereby reducing radiation exposure and increasing efficiency.

Figure 1B:
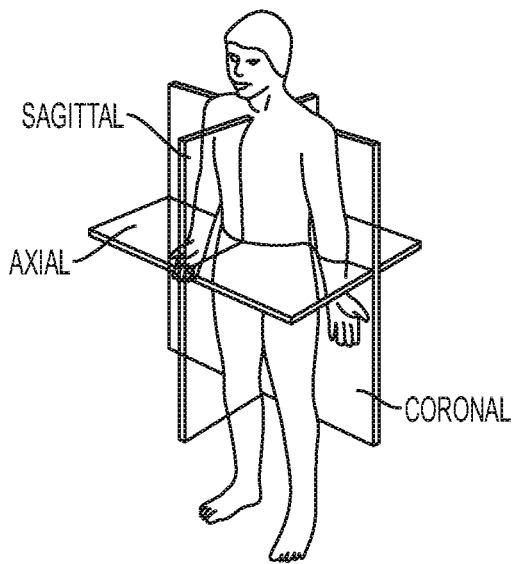
FIG. 1B is a schematic illustration of relevant anatomical planes.

The positional information detected and/or calculated by the surgical electronic module can include one or more angles of the module with respect to the earth (referred to hereinafter as "absolute" angles), one or more angles of the module with respect to a some other reference point (referred to hereinafter as "relative" angles), distances between the module and one or more external reference points, changes in any of these values, a rate of changes in any of these values, and/or higher order derivatives of any of these values. The module can be configured to detect and/or calculate the positional information in a variety of units and coordinate systems. To provide relevant anatomical measurements during surgery, in some embodiments the module can be configured to translate positions and/or orientations detected in a spherical coordinate system, illustrated in FIG. 1A and defined by an absolute azimuth angle θ, an absolute polar angle φ, and a radial distance r, into positions and/or orientations along the sagittal, axial, and coronal planes, illustrated in FIG. 1B.

Figure 2:
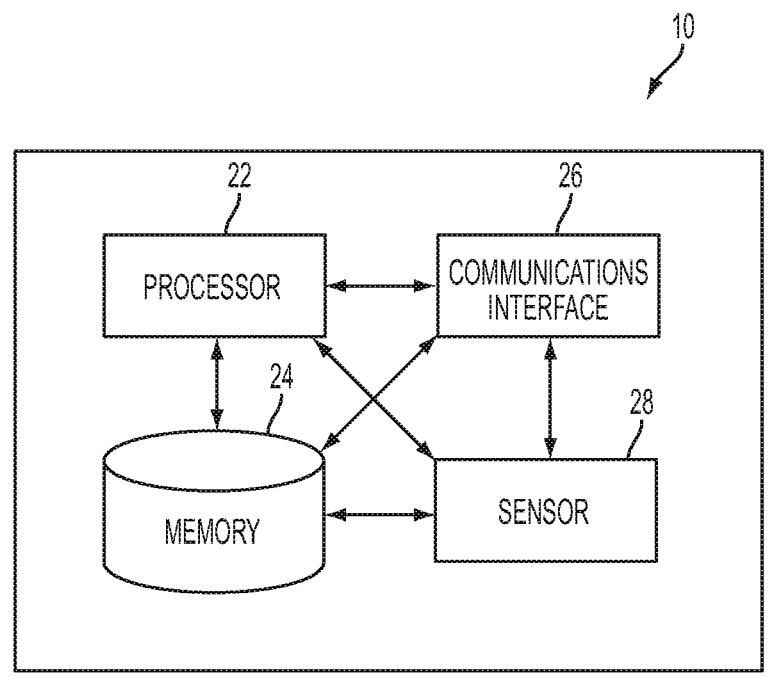
FIG. 2 is a schematic illustration of an exemplary surgical electronic module.

The surgical electronic module can include one or more components for detecting, processing, communicating, and/or storing positional information of the module and the surgical device to which it is attached. As schematically illustrated in FIG. 2, an exemplary module 10 can include a processor 22, a memory 24, a communications interface 26, and a sensor 28—all of which can be in communication with each other. Any of these components can exist external to the module 10, however, for example at a remote base station configured to communicate with the module 10 through the communications interface 26. Further, although each of these components are referred to in the singular, it will be appreciated by a person skilled in the art that the various functions described as being carried out by one of the components can actually be carried out by multiple of those components, e.g., the functions described as being carried out by the processor 22 can be carried out by multiple processors. The electrical components can be powered by a battery contained within the module 10, for example a lithium ion battery, or can be powered by an external power source coupled to the module 10 via an adaptor.

The sensor 28 can be or can include any type of sensor that is configured to detect positional information of the module 10. By way of non-limiting example, the sensor 28 can include an accelerometer (e.g., a 9-axis accelerometer for measuring one or more angles of the module 10 with respect to a reference point such as the earth), a gyroscopic sensor, a geomagnetic sensor, and the like. Additionally or alternatively, where the module 10 is configured to detect a distance of the module from a reference point, the sensor 28 can include ultrasound, electromagnetic, and/or infrared transceivers for communicating with a positioning system. In an exemplary embodiment, the sensor 28 can be configured to detect an absolute position and/or orientation of the module in the spherical coordinate system. The sensor 28 can be configured to detect the positional information at intervals throughout a surgical procedure, for example every second, every millisecond, every microsecond, etc., such that the positional information is effectively detected continuously and in real-time. The positional information can be detected regularly, intermittently, or at non-regular intervals. The positional information can be conveyed to the surgeon, stored in the memory 24, conveyed to the processor 22 for processing, and/or communicated to one or more external devices via the communications interface 26 for processing or storage.

Where the sensor 28 is configured to detect both an orientation and a position (e.g., a distance of the module 10 from some reference point), the module 10 can be configured to switch between an orientation detection mode in which the sensor 28 detects only the orientation and a full detection mode in which the sensor 28 detects both the orientation and the position. The module 10 can be configured to switch between the orientation detection mode and the full detection mode at the request of the surgeon, for example via actuation of an input device on the module 10, and/or based on an identity of the surgical device to which the module 10 is attached.

The processor 22 can include a microcontroller, a microcomputer, a programmable logic controller (PLC), a field-programmable gate array (FPGA), an application specific integrated circuit (ASIC), integrated circuits generally referred to in the art as a computer, and other programmable circuits, and these terms are used interchangeably herein. The processor 22 can be configured to generate positional information and/or perform various calculations based on the positional information detected by the sensor 28, stored in the memory 24, and/or received from an external device via the communications interface 26. By way of non-limiting example, the processor 22 can be configured to calculate a relative position and/or orientation of the module 10 with respect to an external reference point based on an absolute position and/or orientation of the module 10 that is detected by the sensor 28 and/or an absolute position and/or orientation of the external reference point that is received through the communications interface 26. The processor 22 can be configured to calculate changes in the absolute and relative positions and/or orientations of the module 10 and/or a speed at which those changes occur, which will correspond to changes and/or a speed of the surgical device to which the module 10 is attached.

The processor 22 can be coupled to the memory 24, which can include a random access memory (RAM), a read-only memory (ROM), a flash memory, a non-transitory computer readable storage medium, and so forth. The memory 24 can store instructions for execution by the processor 22 to implement the systems disclosed herein or to execute the methods disclosed herein. Additionally or alternatively, the memory 24 can store the positional information sensed by the sensor 28, calculated by the processor 22, and/or received from an external device through the communications interface 26.

The communications interface 26 can be configured to receive and transmit information from any of the processor 22, the memory 24, and the sensor 28 with one or more external devices, e.g., another surgical electronic module, a base station, etc. The communications interface 26 be wireless (e.g., near-field communication (NFC), Wi-Fi, Bluetooth, Bluetooth LE, ZigBee, and the like) or wired (e.g., USB or Ethernet). In the case of NFC, for example, the module 10 can include a radio transceiver configured to communicate with a radio transceiver of another device, e.g., a second module, using one or more standards such as ISO/IEC 14443, FeliCa, ISO/IEC 18092, and those defined by the NFC Forum. The communication interface 26 can be selected to provide the desired communication range. In some embodiments, Bluetooth (e.g., class 2 Bluetooth having a range of 5-10 meters) can be used for the communication interface to allow the module 10 to remain somewhat distant from the device with which it is communicating, e.g., the second module and/or a base station, while at the same time limiting the communication range such that other mobile devices unlikely to be used in the surgery are not needlessly involved.

Figure 3:
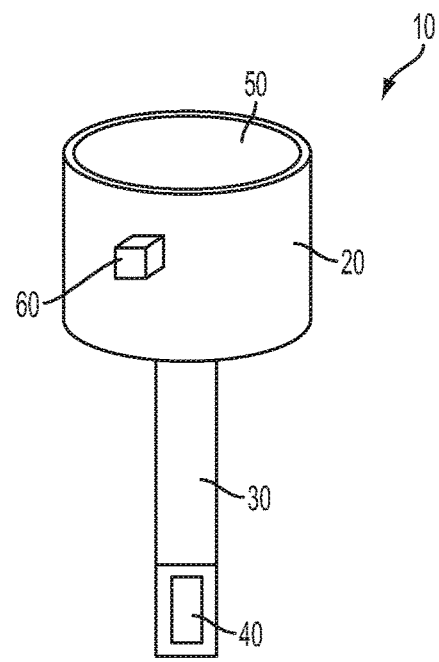
FIG. 3 is a perspective view of the surgical electronic module of FIG. 2.

As shown in FIG. 3, the exemplary module 10 can include a proximal housing 20 and a distal shaft 30. In general, the housing 20 and the shaft 30 can be any size and shape configured to be inserted at least partially into a patient's body during surgery while not substantially obstructing a surgeon's view of or access to a surgical site. Any or all of the above described components for detecting, processing, and/or communicating positional information can be housed within the housing 20. Further, the housing 20 can have various external features for inputting and outputting the positional information, for example the housing 20 can include an electronic display 50 for communicating information detected and/or calculated by the module 10 and/or a zeroing button 60 to allow the user to indicate that the module 10 is in an initial position and/or orientation. The shaft 30 can extend distally from the housing 20 and can be configured to rigidly and mechanically attach the module 10 to the surgical device such that changes in the position and/or orientation of the surgical device result in corresponding changes in the position and/or orientation of the module 10.

The display 50 can be configured to communicate the positional information detected and/or calculated by the module 10 to assist the surgeon in assessing anatomical changes effected by the surgical device to which the module 10 is attached. In the illustrated embodiment, the display 50 is formed on a proximal-facing surface of the housing 20, although the display 50 can be located anywhere on the module 10, e.g., such that it is visible to the surgeon during surgery, or it can be located remotely from the module. The display 50 can be any type of display screen, e.g., liquid crystal, light emitting diode, etc., and in some embodiments can be configured to withstand exposure to sterilization, liquids, and/or high levels of moisture. In an exemplary embodiment, the display 50 can display a change in the absolute or relative position and/or orientation of the module 10 during surgery, which corresponds to a change in the position and/or orientation of the surgical device to which the module 10 is attached. In some embodiments, the display 50 can additionally or alternatively provide positive and/or negative feedback to the surgeon about the position and/or orientation of the module 10. By way of non-limiting example, when the module 10 detects that a desired position and/or orientation has been reached, the display 50 can provide positive feedback to the surgeon, e.g., a green light. When the module 10 is determined to be outside a desirable positional range, the display 50 can provide negative feedback to the surgeon, e.g., a red light, an error message, etc. Other means for communicating information to the surgeon can include, without limitation, a vibrator, a speaker or buzzer for providing audio feedback and an internal or external display in communication with the module 10 for providing visual feedback. The external display can be larger than the display 50 and, in some embodiments, can provide a real-time graphical illustration of the movement of the module 10 and optionally one or more other modules during surgery.

The positional information output by the module 10, for example on the display 50, can be reset to zero at any time by user actuation of a resetting or "zeroing" mechanism to thereby indicate that the module 10 is in an initial position and/or orientation. For example, a position and/or orientation of the module 10 displayed at a starting point of the surgery can to be set to zero upon actuation of the zeroing button 60 by the surgeon, although it will be appreciated by a person skilled in the art that the zeroing mechanism can be any feature on the module 10 or it can be remote to the module 10. After the zeroing button 60 has been pressed, the display 50 can display a change in the position and/or orientation of the module 10 relative to a zero position and/or orientation, such that the surgeon can readily know the difference between the initial position and/or orientation of the module 10 and a current position and/or orientation of the module 10. Thus, where the surgery requires changing a position and/or orientation of a patient's anatomy that is connected to the module 10 via the surgical device by a desired amount, the surgeon can know that the desired change has been effected when the desired change of the module 10 is displayed on the display 50. In some embodiments, actuation of the button 60 can also initiate detection and/or calculation of the position and/or orientation of the module 10.

The module 10 can be configured to attach directly to a patient's anatomy and/or to the surgical device via one or more engagement features 40 formed on a distal portion of the module 10, for example on the distal end of the shaft 30. The surgical device can be anything used in the operating room that facilitates the surgery, including, by way of non-limiting example, surgical implants, surgical instruments, fixtures in the operating room, e.g., an operating table, etc. The engagement features 40 can be specifically configured to mate the module 10 only to a single type of surgical device, or they can be adaptable or modular to allow for mating of the module 10 to any of a variety of surgical devices. Further, the engagement features 40 can be configured to mate the module 10 to more than one surgical device at a time. The engagement features 40 can provide for direct rigid mechanical attachment of the module 10 to the surgical device to thereby ensure that changes in a position and/or orientation of the surgical device result in corresponding changes in the position and/or orientation of the module 10. In some embodiments, the engagement features 40 can be configured to rigidly attach to engagement features of another surgical electronic module to calibrate the module 10 with the other surgical electronic module, e.g., by synchronizing coordinate systems. Non-limiting examples of engagement features 40 include a snap mechanism, a lock-and-key mechanism, an electronic contact, a screw or other threaded feature, etc.

In some embodiments, the engagement features 40 can be configured to detect identification information about the surgical device to which the module 10 is attached. For example, the engagement features 40 can comprise one or more buttons, switches, pressure transducers, etc. that are configured to align with one or more protrusions on the surgical device. The number and arrangement of protrusions can serve to uniquely identify the surgical device. In this way, the number and arrangement of buttons or other components that are engaged by the one or more protrusions on the surgical device can convey identification information about the surgical device. In another embodiment, the engagement features 40 can include a radio frequency identification (RFID) transceiver or optical scanner that is configured to read a unique device identifier (UDI) contained in either an RFID tag or bar code, respectively, on the surgical device. The identification information can include a type of the surgical device, a serial number of the surgical device, an angle at which the surgical device is configured to attach to the module 10, an age of the surgical device, an intended use of the surgical device, etc.

The identification information can be conveyed to the surgeon, for example to ensure that the module 10 has been securely attached to the correct surgical device. Where the module 10 is determined not to have been attached to the correct surgical device, the module 10 can alert the surgeon to the error, for example by displaying an error message on the display 50. In some embodiments, where the identification information includes an angular offset of a portion of the surgical device from the module 10 when the surgical device is attached to the module 10, the identification information can be used to calculate an absolute position and/or orientation of that portion of the surgical device. Additionally or alternatively, the identification information, e.g., a type of the surgical device, can cause the module 10 to detect and/or calculate different types of positional information. By way of non-limiting example, the module 10 can be configured to switch into the full detection mode when the engagement features 40 detect that the module 10 is connected to a surgical instrument that is intended to change position and orientation during surgery, and into the orientation detection mode when the engagement features 40 detect that the module 10 is connected to a surgical device, e.g., an implant, that is only or primarily intended to change orientation during the surgery. In still further embodiments, where the module 10 is in communication with an external display that provides a graphical depiction of the surgery in real-time based on positional information transmitted from the module 10, the external display can use the identification information to incorporate an illustration of the surgical device to which the module 10 is attached in the graphical depiction. The identification information can be stored along with positional information collected and/or calculated by the module 10 during surgery, e.g., to facilitate later reconstruction of the surgery.

The surgical electronic modules disclosed herein can generally be used to detect a position and/or orientation of a surgical device to which they are attached as well as changes in said position and/or orientation. Where the surgical device is also attached to a portion of a patient's anatomy, the surgical electronic module can be used to detect a position and/or orientation of that portion of the patient's anatomy as well as changes in said position and/or orientation. In an exemplary embodiment, two surgical electronic modules can be attached to two pedicle screws to detect an amount of correction in a patient's spinal curvature during a pedicle subtraction osteotomy.

Figure 4:
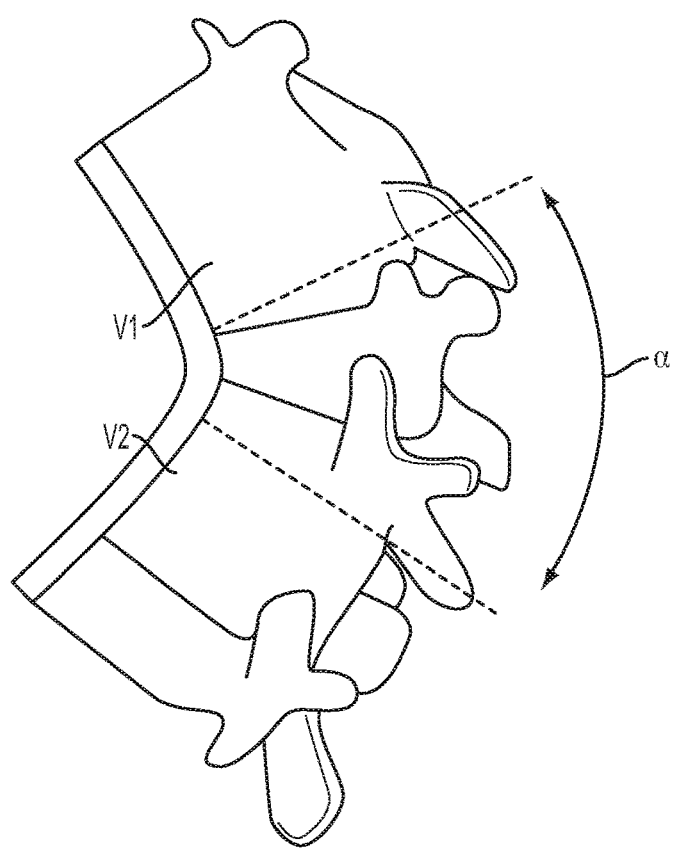
FIG. 4 is a perspective view of a spine of a patient with a spinal deformity.
Figure 5:
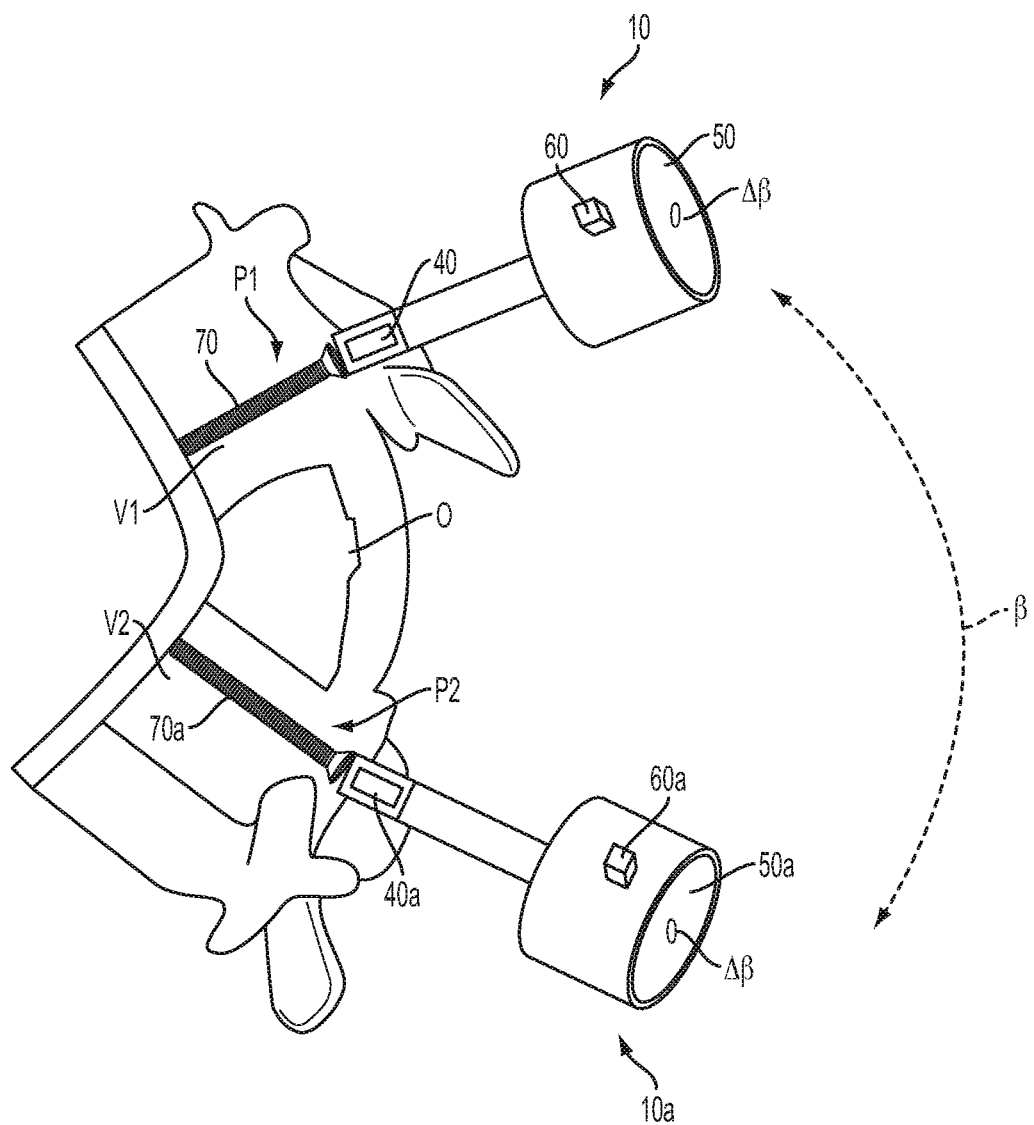
FIG. 5 is a perspective view of one step of an exemplary method for correcting spinal deformity using surgical electronic modules.
Figure 6:
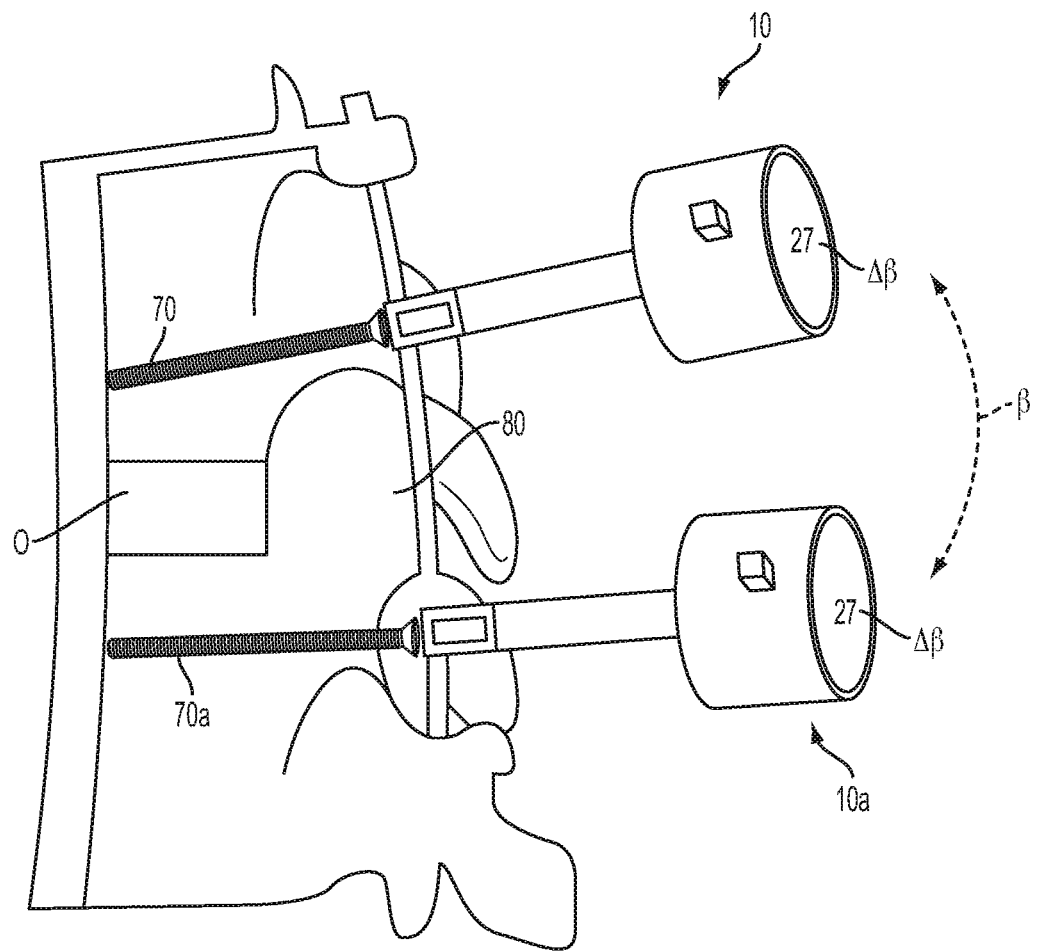
FIG. 6 is a perspective view of another step of the method of FIG. 5.

The steps of an exemplary pedicle subtraction osteotomy utilizing the module 10 and a second module 10a, which can be identical to the module 10, are illustrated in FIGS. 4-6. However, it will be appreciated by a person skilled in the art that any surgical electronic module as described herein can be used, either the same or different from one another, and that the modules 10, 10a can be used in a variety of surgical procedures that effect changes in anatomical position and/or orientation. Further, it will be appreciated that the calculations said to be performed by the modules 10, 10a can either be performed by both of the processors 22, 22a or by only one of the processors 22, 22a. Where the below-described calculations are performed by both of the processors 22, 22a, the modules 10, 10a can communicate the results of the calculations with one another to check for accuracy and can display an error message to the user when there is a mismatch. The calculations can also be performed by a remote base station configured to receive positional information from the modules 10, 10a.

As shown in FIG. 4, prior to the exemplary osteotomy procedure, the patient's lumbar spine includes a kyphotic deformity in which a first vertebra VI is positioned at an angle α in the sagittal plane relative to a second vertebra V2. A purpose of the osteotomy procedure can be to reduce the angle α to a desired value, e.g., by removing a corresponding amount of bone from a vertebra disposed between the vertebrae VI, V2. The amount of angular correction can be determined based on pre-operative imaging and calculations. In some embodiments, prior to surgery, the modules 10, 10a can be calibrated to one another to thereby synchronize their coordinate systems. For example, the modules 10, 10a can be mechanically connected to one another via, e.g., the engagement features 40, 40a, and rotated through space as a pair until sufficient information has been gathered to synchronize their coordinate systems. An output signal can be provided to the user, for example a visual signal on the display 50, a vibration, and/or an audio signal, to indicate when synchronization has been completed. Such synchronization can facilitate automated error correction, e.g., for axial rotations, and/or can facilitate quantification of coronal plane changes.

First and second pedicle screws 70, 70a can be implanted into first and second pedicles P1 and P2 of first and second vertebrae VI and V2, as shown in FIG. 5, according to customary surgical procedures. The first module 10 can be rigidly attached to the first pedicle screw 70 and the second module 10a can be rigidly attached to the second pedicle screw 70a via the engagement features 40, 40a of the first and second modules 10, 10a. The modules 10, 10a can be attached to the pedicle screws 70, 70a either before or after the pedicle screws are implanted. Through this series of connections, changes in the positions and/or orientations of the first and second modules 10, 10a can correspond to changes in positions and/or orientations of the first and second pedicle screws 70, 70a, respectively, and to changes in positions and/or orientations of the first and second pedicles PI, P2 to which the pedicle screws 70, 70a are attached.

Once the modules 10, 10a have been attached to the screws 70, 70a and the screws 70, 70a have been implanted in the pedicles PI, P2 in an initial position and/or orientation, the modules can be powered up and the zeroing buttons 60, 60a can be actuated to indicate to the modules 10, 10a that the modules 10, 10a are in the initial position and/or orientation. Thus, as shown in FIG. 5, the displays 50, 50a can each display "0" to indicate that the modules 10, 10a are oriented at an initial angle relative to one another. As the procedure is performed, the sensors 28, 28a of the modules 10, 10a can detect absolute azimuth and polar angles θ, φ of each of the modules 10, 10a with respect to the earth. The modules 10, 10a can communicate their absolute azimuth and polar angles θ, φ to one other via the communications interfaces 26, 26a. Given this information, the processors 22, 22a can then calculate a relative angle ß of the first module 10 with respect to the second module 10a in the sagittal plane (e.g., by subtracting the absolute angles measured by the modules). The relative angle ß at the initial position and/or orientation of the modules 10, 10a can be stored in the memories 24, 24a.

Angular correction of the spine along the sagittal plane can then be performed according to customary surgical procedures, which can include removal of bone between the first and second vertebrae VI, V2 at an osteotomy site O of a vertebra disposed between the vertebrae VI, V2. During the correction, the sensors 28, 28a can continually detect the absolute azimuth and polar angles θ, φ of the modules 10, 10a and the processors 22, 22a can continually calculate the relative angle ß based on the updated azimuth and polar angles θ, φ. As the relative angle ß changes during the surgery, the processors 22, 22a can further calculate a change Δß in the relative angle ß over a specified period of time. In the illustrated embodiment, where the modules 10, 10a were zeroed at the initial position and/or orientation, the change Δß in the relative angle ß between the initial angle and the current angle (and thus the amount of correction achieved) can be displayed on the displays 50, 50a. In this way, the user can be provided with a real-time, quantitative measurement of angular correction throughout the surgery. When the desired angular correction has been achieved (FIG. 6), as indicated for example by the value of Δß displayed on the displays 50, 50a, the patient's spine can be stabilized in the corrected position and/or orientation.

In some embodiments, the processors 22, 22a can further calculate derivatives of values detected by the sensors 28, 28a and/or calculated by the processors 22, 22a, such as ß, θ, and φ. By way of non-limiting example, the processors 22, 22a can calculate a first derivative of ß, i.e., a rate of change Δß/Δt in the relative angle ß over time, a second derivative of p, i.e., a relative acceleration $Δß/Δt^2$, and/or a third derivative of ß, i.e., a relative jerk $Δß/Δt^3$ of the modules 10, 10a The rates of change Δß/Δt, Δθ/Δt and/or Δφ/Δt can be useful for error checking, for example to indicate whether the patient has been accidentally moved during the procedure. For example, in embodiments where the processors 22, 22a calculate a rate of change Δθ/Δt for each of the modules 10, 10a, it can be assumed that the patient is moving when the rate of change Δθ/Δt of the first module 10 is equal to the rate of change Δθ/Δt of the second module 10a, since it is unlikely that the first and second modules 10, 10a would be moved at precisely the same rate as part of the surgical procedure. Thus, when the rate of change Δθ/Δt of the first module 10 is equal, or at least substantially equal, to the rate of change Δθ/Δt of the second module 10a, either or both modules 10, 10a can alert the surgeon to the patient's movement, for example by displaying an error message on the displays 50, 50a. Additionally or alternatively, to provide clinical feedback, the rates of change Δß/Δt, Δθ/Δt and/or Δφ/Δt can be displayed, e.g., on the displays 50, 50a, and/or stored, e.g., in the memories 24, 24a. Information about the rates of change Δß/Δt, Δθ/Δt and/or Δφ/Δt can be useful for clinicians because they provide a measure of how quickly an anatomical adjustment is made, which may correlate to patient outcomes.

In some embodiments, spinal fixation or stabilization hardware (e.g., screws and rods) can be coupled to a first side of the patient's spine before correction is performed without locking down the fixation hardware. The modules can be coupled to screws implanted in a second, contralateral side of the patient's spine. After the desired amount of correction is achieved, the fixation hardware in the first side of the patient's spine can be locked down to maintain the corrected angle. The modules can then be removed and a spinal fixation element 80 can be attached to the pedicle screws 70, 70a implanted in the second, contralateral side to complete the fixation. In other embodiments, spinal fixation or stabilization hardware can be coupled only to a single side of the patient's spine, e.g., a side on which the modules 10, 10a are attached. It will be appreciated that the modules 10, 10a can be removed from the pedicle screws 70, 70a either before or after a spinal fixation element or rod 80 is coupled to the pedicle screws.

The above-described method involves a single level osteotomy and first and second modules 10, 10a configured to measure a local correction, however it will be appreciated that more complex deformity correction can also be performed. For example, rotational deformities or angular deformities in any of the sagittal, axial, and/or coronal planes can be corrected and the degree of correction monitored using the modules disclosed herein. By way of further example, several modules (e.g., three, four, five, six, seven, eight, or more) can be coupled to corresponding vertebrae to provide correction measurements for a spinal segment (e.g., a lumbar region, a thoracic region, a cervical region, etc.) or for an entire spine (e.g., from skull to tailbone). Measurement data associated with such procedures can be communicated to an external display to give the surgeon a graphical depiction of overall spinal correction.

Although not shown, additional information can be displayed on the displays 50, 50a and/or on an external display in communication with the modules 10, 10a. The information displayed on the display 50 can be selected by a user before the procedure, can be impacted by the surgical device to which the module 10 is attached, and/or can be preconfigured as part of the factory settings of the module 10. By way of non-limiting example, the modules 10, 10a can convey positive and/or negative feedback to the surgeon during surgery. For example, the displays 50, 50a can convey an error message to the user when the change $\Delta\beta$ in the relative angle $\beta$ exceeds the desired angular correction, when the engagement features 40, 40a detect that they are not attached to the correct surgical device, and/or when engagement between the engagement features 40, 40a and the pedicle screws 70, 70a has been lost or weakened. In some embodiments, where the processors 22, 22a are configured to calculate the rate of change $\Delta\beta/\Delta t$ in the relative angle $\beta$, the displays 50, 50a can convey an error message to the user when the rate exceeds a predetermined speed limit. In still further embodiments, should the patient be rotated in the axial plane during the surgery, for example due to a table rotation or rolling over of the patient, one or both of the modules 10, 10a can detect the change and can be configured to alert the surgeon via an error message on the displays 50, 50a, which may include an instruction to recalibrate. In case of a need to recalibrate, the modules 10, 10a can be detached from the screws 70, 70a and can be attached to one another to repeat the calibration procedure described above.

Information detected and/or calculated by the modules 10, 10a during the procedure can be collected and stored for later use. The information can be stored locally in the memories 24, 24a and/or can be transmitted via the communications interfaces 26, 26a to one or more external base stations. The stored information can be used at a later time for various purposes, for example to create a reproduction of the surgery, for clinical improvement, research, and/or ethnography.

Figure 7:
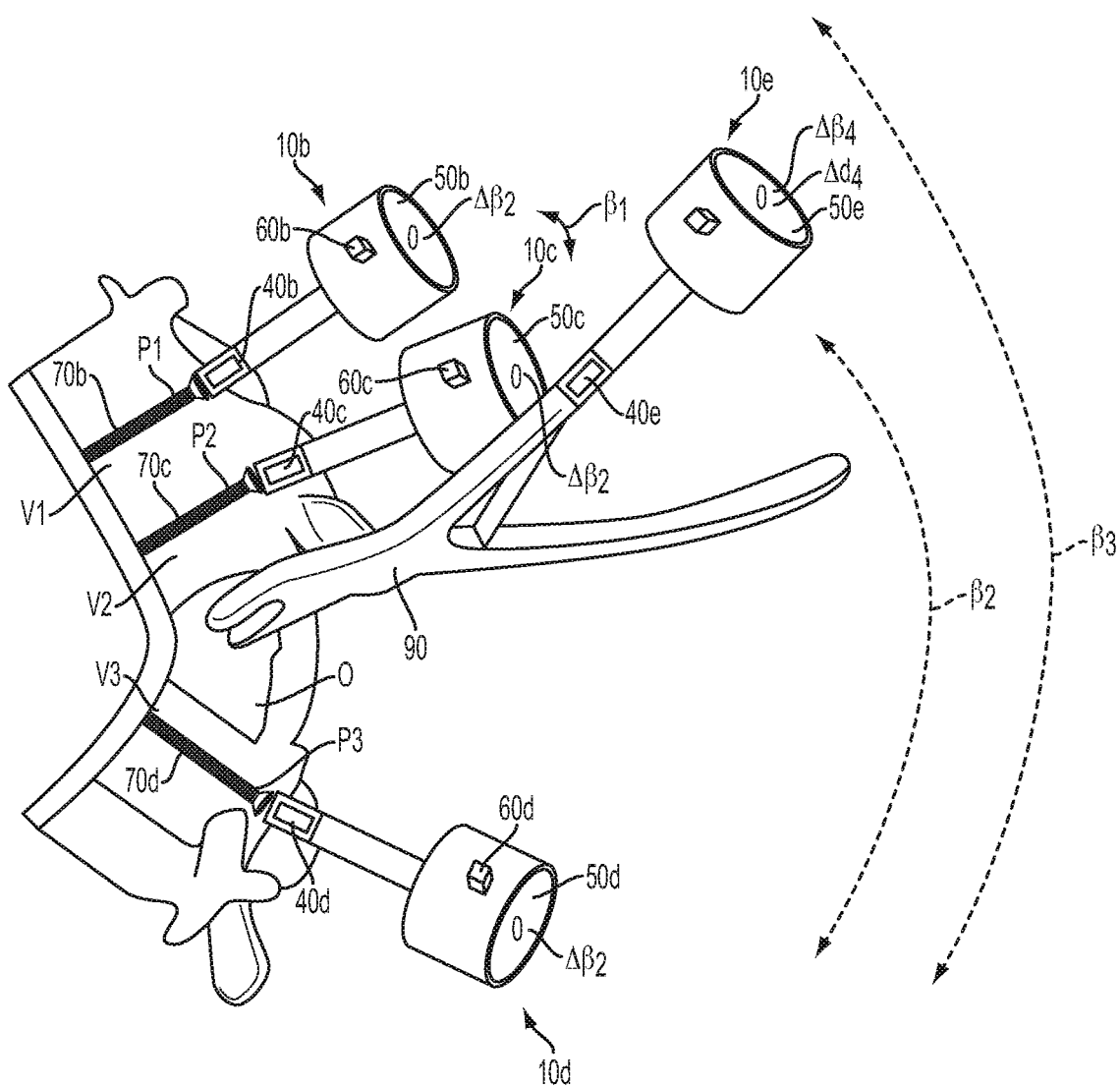
FIG. 7 is a perspective view of one step of another exemplary method for correcting spinal deformity using surgical electronic modules.
Figure 8:
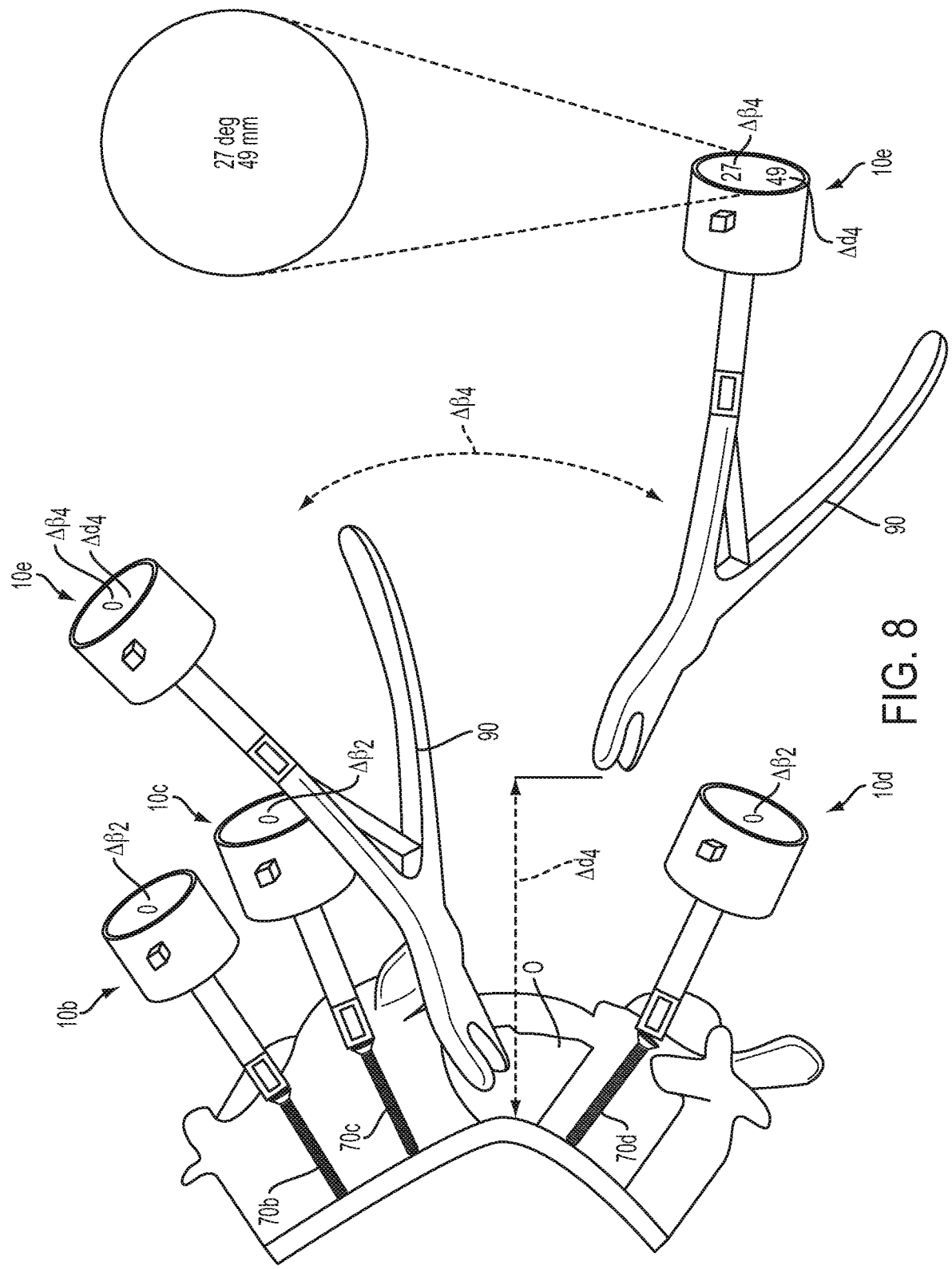
FIG. 8 is a perspective view of another step of the method of FIG. 7.

Another exemplary pedicle subtraction osteotomy using one or more surgical electronic modules as described herein is illustrated in FIGS. 7 and 8. The procedure according to this method involves the use of four surgical electronic modules 10b, 10c, 10d, 10e, which can detect, calculate, store, and/or transmit information in a similar manner to the modules 10, 10a described above during the exemplary pedicle subtraction osteotomy of FIGS. 4-6. It will be appreciated by a person skilled in the art that any surgical electronic module as described herein can be used, either the same or different from one another, and that the modules 10b, 10c, 10d, 10e can be used in a variety of surgical procedures that effect changes in anatomical position and/or orientation.

Similarly to the procedure described with reference to FIGS. 4-6, a desired angular correction of the spine can be determined prior to the surgery. The modules 10b, 10c, 10d, 10e can be calibrated by freely rotating mated pairs of the modules 10b, 10c, 10d, 10e until enough positional information has been acquired to synchronize their coordinate systems. For example, the module 10b can be attached to each of the other modules 10c, 10d, 10e, and synchronized with each of the other modules 10c, 10d, 10e to ensure that all of the modules 10b, 10c, 10d, 10e are synchronized to each other.

The first three modules 10b, 10c, 10 can be rigidly attached to three pedicle screws 70b, 70c, and 70d, while the fourth module 10d can be rigidly attached to a surgical cutting instrument such as a rongeur 90. The engagement features 40b, 40c, 40d, 40e can detect an identity of the device to which the modules 10b, 10c, 10d, 10e are attached, such that the first three modules 10b, 10c, 10d can detect that they are each attached to a pedicle screw and the fourth module 10e can detect that it is attached to a rongeur. Based on this information, the first three modules 10b, 10c, 10d can switch into the orientation detection mode in which only orientation information is displayed to the user, and the fourth module 10e can switch into the full detection mode in which orientation and position information is displayed. Further, as explained in detail below, the processors 22b, 22c, 22d of the first three modules 10b, 10c, 10d can be configured to calculate different positional information from the processor 22e of the fourth module 10e. It will be appreciated by a person skilled in the art, however, that the procedure can be performed utilizing only three modules, two of which are attached to two pedicle screws and the third of which is attached to a surgical cutting instrument.

The pedicle screws 70b, 70c, 70d can be implanted into pedicles PI, P2, and P3 on vertebrae VI, V2, and V3, either before or after the modules 10b, 10c, 10d are attached thereto. At least one of the pedicle screws 70b, 70c, 70d can be implanted on an opposite side of an intended osteotomy site O from at least one of the other pedicle screws 70b, 70c, 70d. Similarly to the modules 10, 10a used in the exemplary procedure of FIGS. 4-6, an initial position and/or orientation of the modules 10b, 10c, 10d with respect to one another can be set by actuating the zeroing buttons 60b, 60c, 60d. Thus, as shown in FIG. 7, the displays 50b, 50c, 50d can each display "0" to indicate that the modules 10b, 10c, 10d are oriented at an initial angle relative to one another. Angular correction of the spine along the sagittal plane can then be performed according to customary surgical procedures, which can include removal of bone from a vertebra disposed between the second and third vertebrae V2, V3 by the rongeur 90. During the procedure, the sensors 22b, 22c, 22d can continually detect absolute azimuth and polar angles θ, φ of each of the modules 10b, 10c, 10d. The modules 10b, 10c, 10d can communicate their absolute azimuth and polar angles θ, φ with each other (e.g., via Bluetooth or other wired or wireless communication) to thereby allow for the processors 22b, 22c, 22d to calculate a relative angle $ß_1$ of the first module 10b with respect to the second module 10c, a relative angle $ß_2$ of the second module 10c with respect to the third module 10d, and a relative angle $ß_3$ of the first module 10b with respect to the third module 10d. Further, the modules 10b, 10c, 10d can calculate changes $\Delta ß_1$, $\Delta ß_2$, $\Delta ß_3$ in the relative angles $ß_1$, $ß_2$, $ß_3$ throughout the procedure, rates of changes $\Delta ß_1/\Delta t$, $\Delta ß_2/\Delta t$, $\Delta ß_3/\Delta t$ and/or rates of changes $\Delta θ/\Delta t$, $\Delta φ/\Delta t$ in the azimuth and polar angles θ, φ of each of the modules 10b, 10c, 10d.

Because the relative angle $ß_1$ of the modules 10b, 10c with respect to one another does not change throughout the procedure since the modules 10b, 10c are on the same side of the osteotomy site O, the modules 10b, 10c, 10d can be configured to display only $\Delta ß_2$. The displays 50b, 50c, 50d can be configured not to display the change $\Delta ß_1$ since it will remain substantially equal to zero throughout the procedure, and not to display the change $\Delta ß_3$ because $\Delta ß_2$ and $\Delta ß_3$ will remain substantially equal to one another throughout the procedure. Of course, it will be appreciated by a person of skill in the art that the modules 10b, 10c, 10d could display either $\Delta ß_2$ and $\Delta ß_3$, since they are substantially equal to one another, and $\Delta ß_2$ has been chosen solely for purposes of illustration. Also, if at any point during the surgery, $\Delta ß_1$ ceases to be substantially equal to zero and/or $\Delta ß_2$ and $\Delta ß_3$ cease to be substantially equal to one another, all three relative angular changes $\Delta ß_1$, $\Delta ß_2$, $\Delta ß_3$ can be displayed on the displays 50b, 50c, 50d. Any of these values can be displayed on an external display alternatively or in addition.

The module 10e can be attached to the rongeur 90 via engagement features 40e on the module 10e at any point during the surgery to help the surgeon remove a desired amount of bone from a desired location. Like the modules 10b, 10c, 10d, the module 10e can be "zeroed" by user actuation of the zeroing button 60e when the module 10e is placed in an initial position and/or orientation, e.g., when the rongeur 90 to which the module 10e is coupled is inserted at a desired cutting angle and at a maximum desired cutting depth into the patient's body. Thus, as shown in FIG. 7, the module 10e can display two zeros, one indicating an initial angle and one indicating an initial distance. Preferably, the module 10e is zeroed before any angular correction in the patient's spine has been achieved and/or at the same time that the other modules 10b, 10c, 10d are zeroed.

Because the module 10e is able to detect that it is attached to a surgical instrument, e.g., the rongeur 90, as opposed to a surgical implant, e.g., the pedicle screws 70b, 70c, 70d, it can be configured to calculate and/or display different positional information than the modules 10b, 10c, 10d. This information can supplement the information displayed by the modules 10b, 10c, 10d to confirm that a desired angular correction has been achieved. In particular, whereas the modules 10b, 10c, 10d are configured to calculate and/or display changes in positional information with respect to one another, the module 10e can be configured to calculate and/or display changes in its own positional information throughout the surgery. Further, whereas the modules 10b, 10c, 10d are configured to calculate and/or display changes in their relative orientations, the module 10e can be configured to calculate and/or display changes in both orientation and position.

To perform these calculations, the module 10e can continually detect absolute azimuth and polar angles θ, φ of the module 10e with the sensor 28e, calculate an absolute angle $ß_4$ of the module 10e in the sagittal plane with the processor 22e, and store the absolute angle $ß_4$ for any given time in the memory 24e. Similarly, the sensor 28e can continually detect an absolute position (e.g., including a distance $d_4$ of the module 10e relative to a starting position) via triangulation, time-of-flight, or other positioning algorithms using ultrasonic, electromagnetic, and/or infrared location signals sent by each of the modules 10b, 10c, 10d, 10e and communicated therebetween. It will be appreciated by a person skilled in the art that, where at least three modules are used, unique position information can be created through location signals sent out by each of the modules and communication among all of the modules of the information received from the signals while the modules 10b, 10c, 10d are stationary, e.g., before they are moved together as part of reduction procedure. It will further be appreciated by a person skilled in the art that the position of the rongeur 90 can be determined through communication between the module 10e and other surgical electronic modules positioned in the operating room. As the position and/or orientation of the rongeur 90 changes during surgery, the processor 22e can calculate and the display 50e can display a change $\Delta ß_4$ in the angle $ß_4$ and/or a change $\Delta d_4$ in the distance $d_4$ of the module 10e—and therefore of the rongeur 90—in the sagittal plane. For example, as shown in FIG. 8, the display 50e can indicate that the rongeur 90 has moved by a distance of 49 mm and by an angle of 27 degrees from the initial position and orientation. In this way, the surgeon can know when the rongeur 90 has completed a desired motion to thereby remove a desired amount of bone. In some embodiments, the module 10e can be configured to alert the surgeon when the rongeur 90 is moved outside of or beyond a surgical plane, e.g., beyond a desired angle and/or distance, for example by displaying an error message on the display 50 and/or providing an audio signal or vibration. For example, the surgeon can be warned when the distal end of the rongeur is approaching or has exceeded a predetermined maximum insertion depth in the anterior direction (e.g., when the axial displacement of the rongeur relative to the starting position approaches zero or becomes negative).

Similarly to the exemplary pedicle subtraction osteotomy of FIGS. 4-6, when the desired angular correction of the spine in the sagittal plane has been achieved, the change $\Delta ß_2$ in the relative angle $ß_2$ displayed on the displays 50b, 50c, 50d will be equal to the desired angular correction. The patient's spine can then be stabilized in the corrected position via a spinal fixation element 80 that can be attached to the implanted pedicle screws 70b, 70c, 70d. The modules 10b, 10c, 10d can be removed from the pedicle screws 70b, 70c, 70d and the module 10e can be removed from the rongeur 90 either before or after fixation with the spinal fixation element 80.

It will be appreciated by a person skilled in the art that a greater number of modules can enhance the accuracy of the procedure by providing for a greater amount of positional information. For example, using more modules can provide positional information to a greater degree of precision and/or specificity, e.g., with more significant digits, which can be displayed to the surgeon. As each module is added in the procedure, the number of significant digits displayed to the surgeon can increase, thereby providing a measure of the increase in accuracy added by each additional module to the surgeon. Additionally or alternatively, using a greater number of modules can enable the modules to detect and/or calculate their positions and/or orientations in more dimensions. The positions, orientations and/or changes in the positions and/or orientations of the modules can be displayed to the user for each plane in which information is acquired. However, it will also be appreciated by a person of skill in the art that a position and/or an orientation of the module in certain planes need not be calculated since it can be assumed that the patient will not move in certain planes.

It will further be appreciated by a person skilled in the art that the devices and methods described herein can be particularly useful for robotic assisted surgery. For example, one or more surgical electronic modules as described herein can transmit positional information to a robotic manipulator, which can manipulate the one or more modules until they have reached a desired final position that has been input to the manipulator.

Further embodiments of devices and methods for intraoperatively measuring position or angular orientation are also provided. In one embodiment, measuring simultaneous angles in multiple orthogonal planes can be accomplished using a single device that includes an integrated display. Such a device can be permanently assembled to medical tools and instruments in some embodiments, while in other embodiments it can be modular to allow for use with a number of medical tools and instruments during surgery. A 9-axis inertial motion unit (IMU) or sensor consisting of a 3-axis accelerometer, a 3-axis gyroscope, and a magnetometer can be housed inside the device to allow angular measurements. In another embodiment, a 3-axis accelerometer alone can be used to allow angular measurement between orthogonal planes. In other embodiments, any of a variety of other sensors can be employed that can provide information related to the position and/or orientation of the sensor.

Figure 9A:
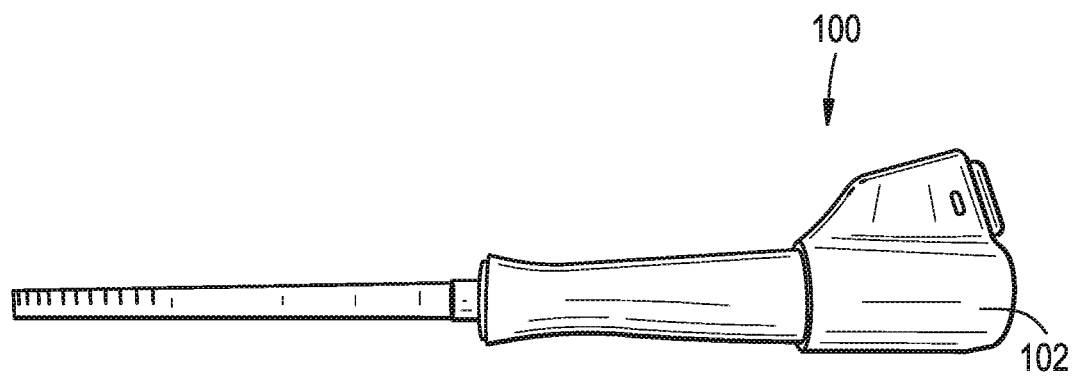
FIG. 9A is a side view of one embodiment of a surgical instrument including an electronic module.
Figure 9B:
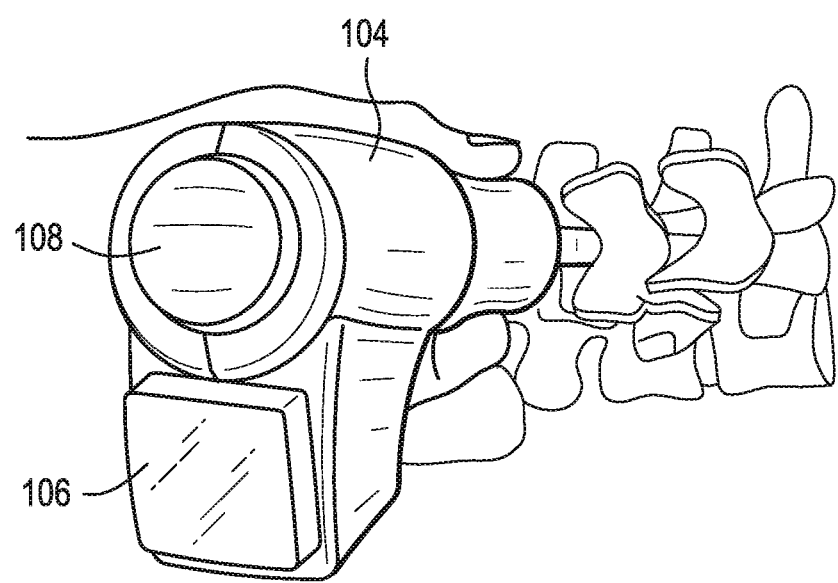
FIG. 9B is a top view of the surgical instrument of FIG. 9A.
Figure 10:
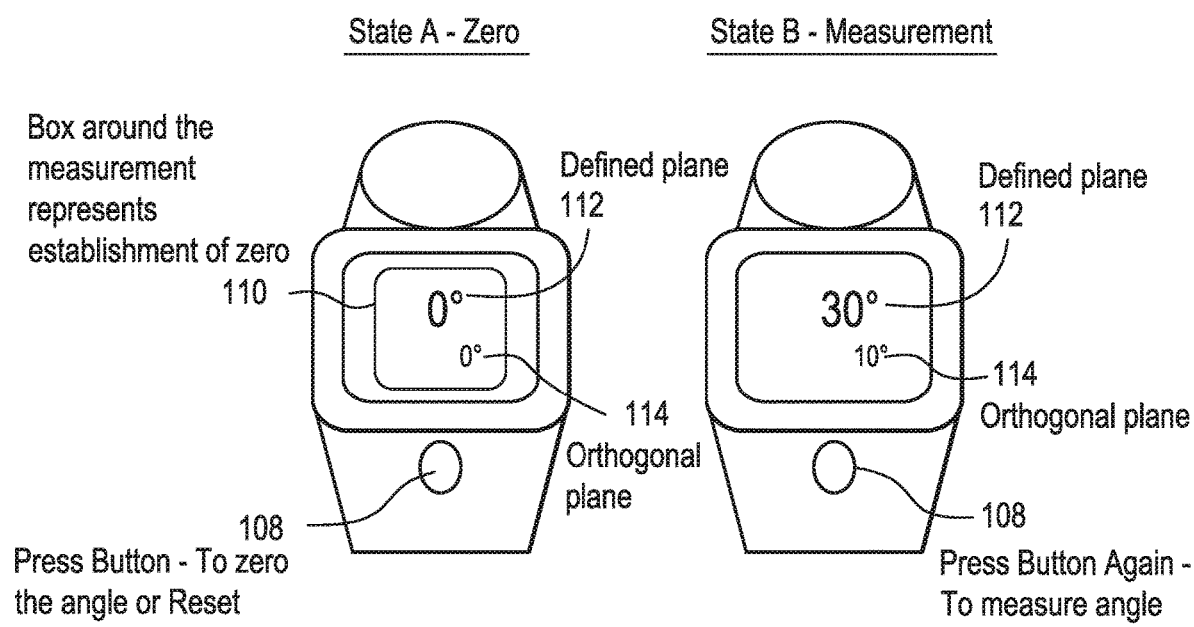
FIG. 10 is a schematic illustration of one embodiment of an electronic module with a single button input.

FIGS. 9A and 9B illustrate one embodiment of such a device 100 that is integrally formed with an electronic module 102 for detecting position or orientation information during use. The module 102 can include a housing 104 containing a sensor (not shown), a processor (not shown), and a display 106 for communicating information to a user. The device 100 can also include an input for receiving instruction from a user. In the illustrated embodiment, the input can be a single button 108, though in other embodiments different inputs, such as toggles, switches, a plurality of buttons, etc. can be utilized. For example, and as shown in FIGS. 9A-12, the button 108 can allow a user to zero and successively complete angular measurement. By way of further example, a single press of the button 108 can calibrate the sensor to initialize or zero the angular measurement at a desired starting location (see FIG. 10 left side, referred to as "State A"). This can be represented by a thin box 110 around the 0° displays, as shown in FIG. 10. A second press of the button 108 at a new location can define a desired plane between the starting and the new location. The instrument 100 can provide angular measurement between these locations in two planes, i.e., the newly defined plane 112 and the plane 114 that is orthogonal to the defined plane but still parallel to the gravitational field (see FIG. 10 right side, referred to as "State B").

In another embodiment, a device 120 can provide for defining a projection plane, parallel to a gravitational field, between two locations by using, for example, two depressions of a button or other input. For example, a user can press a button 122 once at a starting location (labeled State A and passing through point A in FIGS. 11A and 11B) and press the button a second time at a second, new location (labeled as State B and passing through point B in FIGS. 11A and 11B). This can allow for defining a desired projection plane (Plane X in FIGS. 11A-12) for angular measurement. Depression of the button 122, for example third and fourth times, can allow angular measurements between any other two locations. Measurements between these locations can be displayed as projected angles in the newly defined projection plane (Plane X in FIGS. 11A-12) and a plane orthogonal to the defined projection plane (Plane Y in FIGS. 11A-12).

Figure 11A:
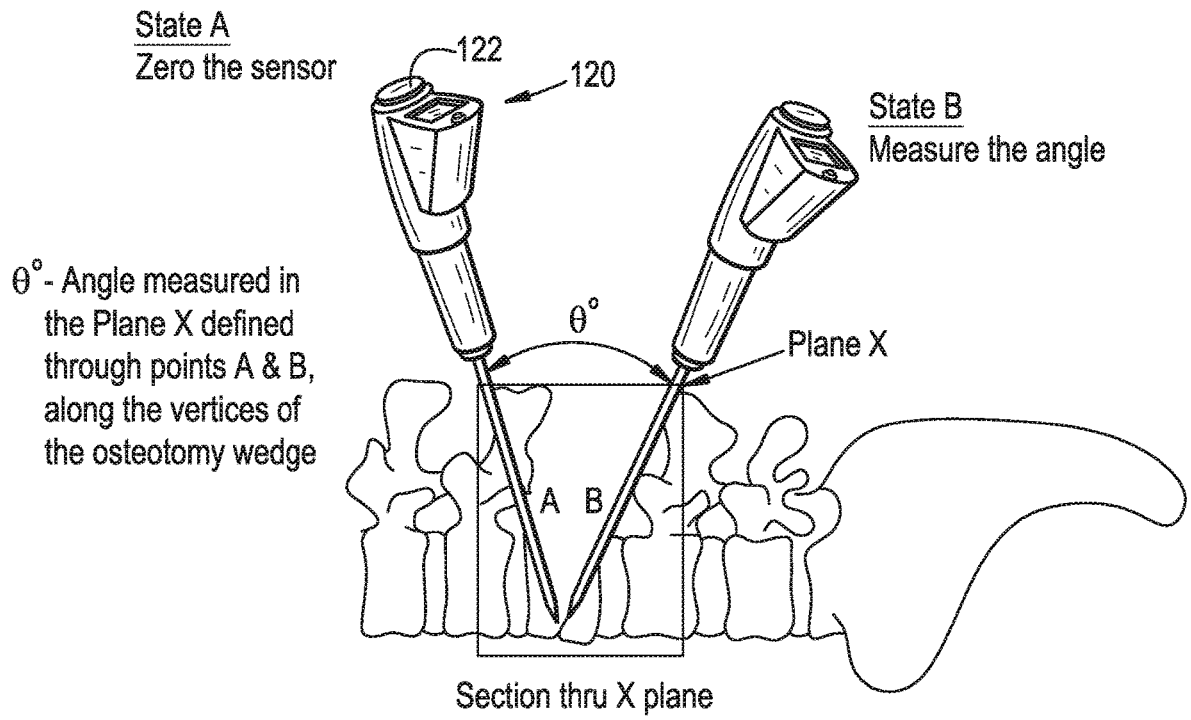
FIG. 11A is a schematic illustration of one embodiment of a surgical instrument with an electronic module measuring changes in position or orientation in a first plane.
Figure 11B:
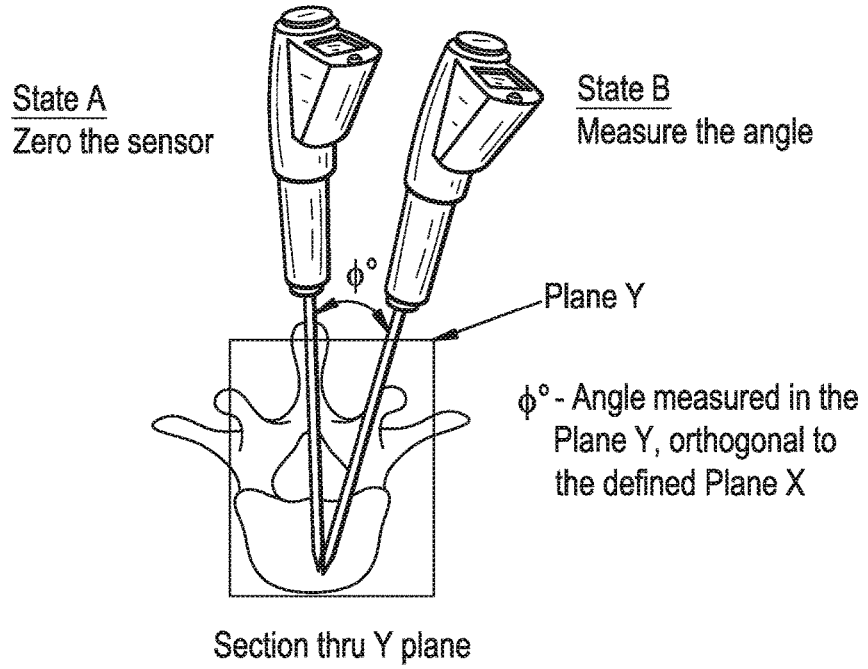
FIG. 11B is a schematic illustration of the surgical instrument of FIG. 11A measuring changes in position or orientation in a second plane orthogonal to the first plane.
Figure 12:
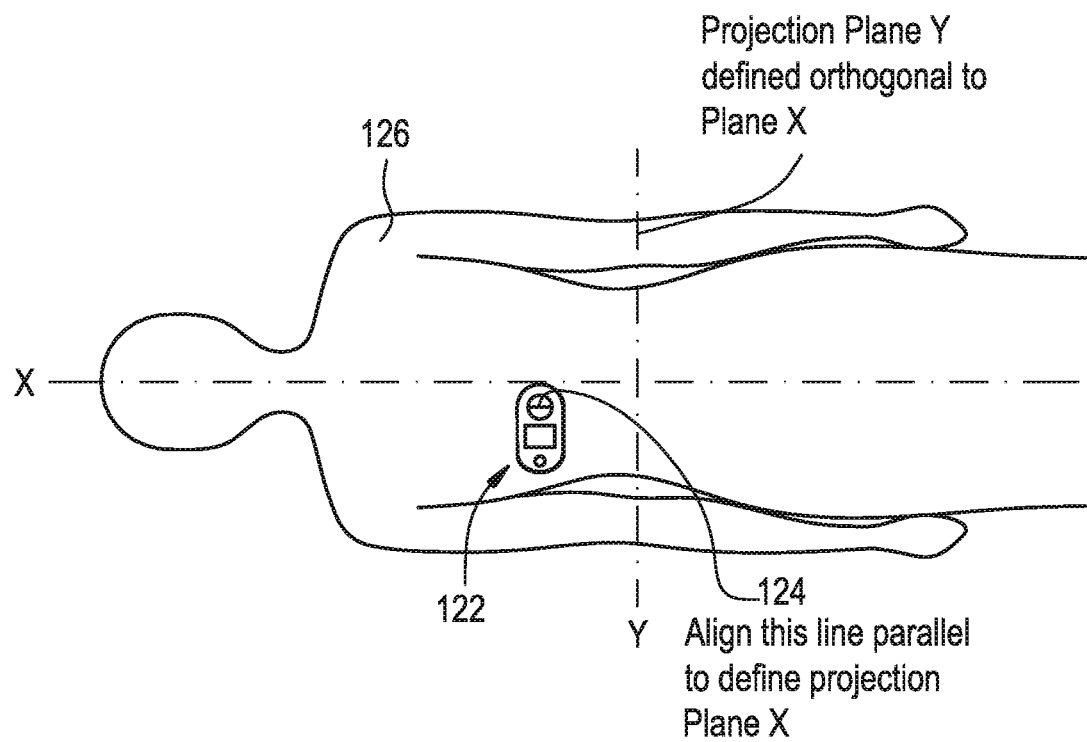
FIG. 12 is a schematic illustration of one embodiment of a surgical instrument defining first and second orthogonal projection planes in which to measure changes in position or orientation.

By way of further example, FIG. 11A illustrates the measurement of an angle θ in labeled Plane X between a first position of the instrument 120 at labeled State A and a second position of the instrument at labeled State B. FIG. 11B illustrates an orthogonal section view and the measurement of an angle φ in labeled Plane Y (which is orthogonal to Plane X in FIG. 11A) between the first position of the instrument 120 at labeled State A and the second position of the instrument at labeled State B. FIG. 12 illustrates the labeled planes X and Y from a top view, showing their orthogonal relationship to one another.

FIG. 12 also illustrates a top view the instrument 122 showing a reference plane alignment feature 124 to aid a user in defining orthogonal projection planes relative to a patient 126. The reference plane alignment feature 124 can be, for example, a ridge, depression, line, or other marking that a user can reference to align the instrument 122 with a desired reference or projection plane. In the illustrated embodiment, for example, the instrument is positioned such that the reference plane alignment feature 122 is aligned with the projection plane labeled Plane X. The projection plane labeled Plane Y is established based on Plane X without need for a dedicated reference feature on the instrument 122. In some embodiments, however, a secondary marking or feature could be included to explicitly denote the orientation of the orthogonal projection or reference plane.

The devices and methods described herein, including the sensors used to detect changes in position or orientation, can be utilized in connection with a number of surgical instruments. In one embodiment, for example, sensors can be attached to an osteotome or chisel for accurate bone cutting to create a desired wedge during a pedicle subtraction osteotomy to achieve planned sagittal balance. During cutting these osteotomies, surgeons often want to know both the angle for the wedge and also the angle of attack in the orthogonal plane. In some cases, surgeons cut osteotomies in a medial to lateral direction at a certain angle to avoid any unintended damage to the critical anatomy in case of slips and overcuts.

The devices and methods described herein can also allow surgeons to create asymmetric wedges at each level for complex deformity correction procedures that require correction of sagittal and coronal balance. Prior techniques often include in-vivo use of many cobbled together methods, including a combination of "eyeballing," experience, estimation, multiple fluoro images or the use of templates, wedges, and rasps to estimate bone removal work. Utilizing the devices and methods described herein can provide a number of advantages over these prior techniques. Furthermore, the devices and methods can be applied to other osteotomies performed in trauma, joints, and CMF (craniomaxillofacial) procedures.

For example, there is currently no quick way to measure sagittal balance and regional curves intraoperatively during deformity and degenerative surgeries. Prior techniques often involve taking fluoro-images, sending them to a PACs (Picture Archiving and Communication) system, and using the images to measure correction with a manual protractor. Such a technique can require a surgeon to leave a sterile field, which is not desirable and increases surgery time. In one embodiment, a device according to the teachings provided herein can be coupled to any medical device, tool, or instrument that can be aligned with two endplates at the apex of a desired curve by means of fluoro-images to measure desired lordosis or kyphosis plus scoliosis angles simultaneously.

In another embodiment, a sensor can be coupled to a deformity correction instrument, such as quick-sticks, towers, frames, or flex-clips, during derotation and axial correction of the spine. Surgeons can attach sensors to these instruments before starting the correction or maneuvers in some embodiments. During this time, a surgeon can decide to zero the sensors and, after final correction, the sensors can provide more information on the angular correction achieved in the axial and sagittal planes.

In still another embodiment, a surgeon can attach one or more sensors to Lenke probes, gearshifts, awls, drills, or taps that can assist surgeons to achieved planned pedicle screw trajectory or pedicle preparation trajectory. The devices and methods described herein can also be used to train surgeons to place mPACT (medialized Posterior Approach Cortical Trajectory) cortical screws, iliac screws and SAI (Sacral-Alar-Iliac) screws using an optimized trajectory.

Furthermore, a surgeon can use the devices described herein to measure and register an angle used to place a pedicle screw on one side of the vertebrae, and then use this registered information to mirror a pedicle screw trajectory on other side. This can allow surgeons to have pedicle screws inserted symmetrically across the spine, which can further allow similar bent rods to be placed on each side. Rod bending is a highly cumbersome and skilled art, using similar bent rods on each side of a patient's spine can save significant time.

The embodiments described above and illustrated in 9A-12 include a single sensor and a one-button interface. In other embodiments, a device can include, for example, a different number of buttons for an input or interface. By way of further example, a single sensor device can include a four-button interface, as described below and illustrated in FIGS. 13A-16. The number of buttons can be varied, however, based on desired workflow and/or usability. For example, short and long presses of one or more buttons can be utilized to provide functionality equivalent to other embodiments in which a larger number of buttons are included.

The embodiment described below can be utilized for measuring anatomical, instrumental, or device based change in position or angular orientation. In this embodiment, systems quantitatively measure changes in the position or angular orientation of a portion of a patient's anatomy or a medical device with respect to another portion of the patient's anatomy or a medical device during surgery. The devices and methods described herein can be utilized to achieve the same functionality described above and in U.S. application Ser. No. 14/471,120, entitled "SYSTEMS AND METHODS FOR INTRAOPERATIVELY MEASURING ANATOMICAL ORIENTATION," filed Aug. 28, 2014, and now issued as U.S. Pat. No. 9,993,177, the entire contents of which are hereby incorporated by reference. One advantage of the embodiments described herein, however, is that this functionality can be achieved with a single sensor housed in a medical device.

Figure 13A:
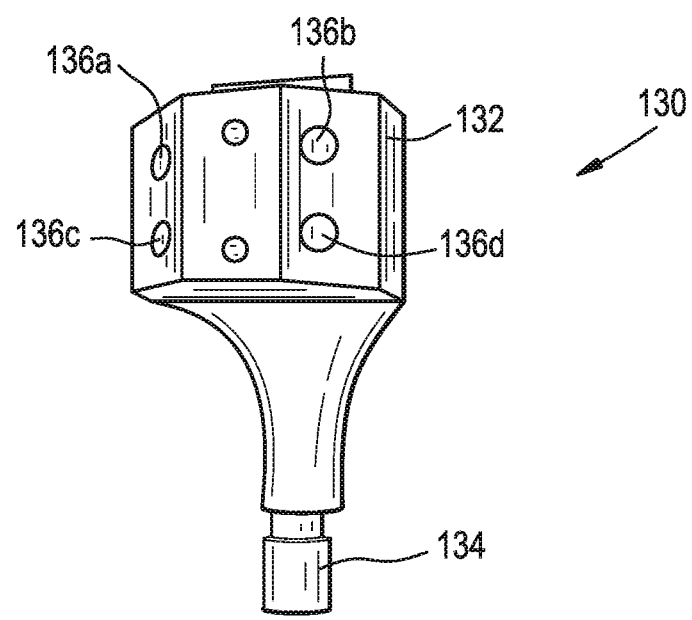
FIG. 13A is a side view of one embodiment of an electronic module with a four-button input.
Figure 13B:
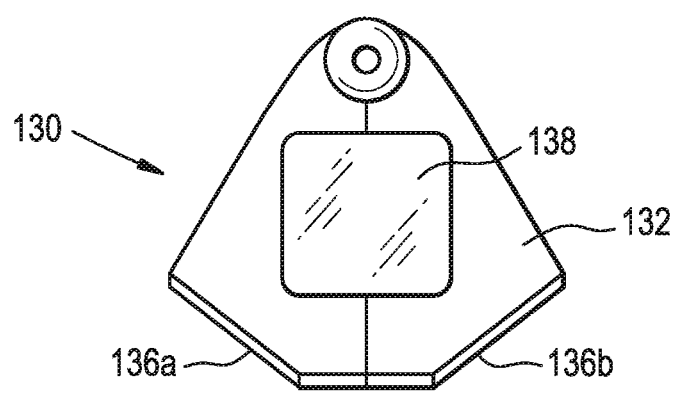
FIG. 13B is a top view of the electronic module of FIG. 13A.

As shown in FIGS. 13A and 13B, a device 130 can include an electronic module 132 permanently assembled to a medical tool and/or instrument 134 in one embodiment. In another embodiment, the module 132 can be modular to allow for use with number of medical tools and instruments during a surgery. As noted above, a 9-axis inertial motion unit (IMU) or sensor that can include a 3-axis accelerometer, a 3-axis gyroscope, and a magnetometer, can be housed inside the device to provide angular measurements. In another embodiment, a 3-axis accelerometer alone can be used to provide angular measurement between orthogonal planes.

Operation of devices, such as the device 130, illustrated in 13A-16 is described below. The device 130 can include an input 136 that, in the illustrated embodiment, includes four buttons 136a, 136b, 136c, 136d that can allow a user to provide instruction regarding measurement of a change in position or angle. Further, a display 138 can communicate measured or calculated position or orientation data back to a user during use.

Figure 14A:
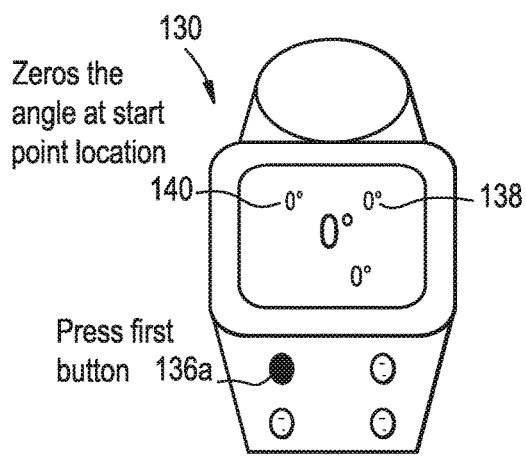
FIG. 14A is a schematic illustration of a first step in operating one embodiment of an electronic module with a four-button input.

As shown in FIG. 14A (and referred to as "State A"), a first button 136a can be initially lit to indicate to a user that this button should be pressed for a next action. Pressing the first button 136a can allow a user to zero and calibrate the sensor in a first starting position. The display can display one or more zeros 140 to denote positioning of the instrument at a starting position/orientation. For example, in FIG. 15A the instrument 130 is attached to the screw A in the starting position.

Figure 14B:
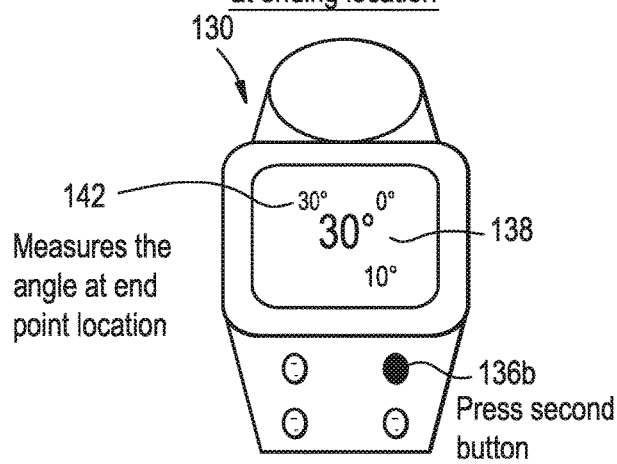
FIG. 14B is a schematic illustration of a second step in operating the electronic module of FIG. 14A.
Figure 15A:
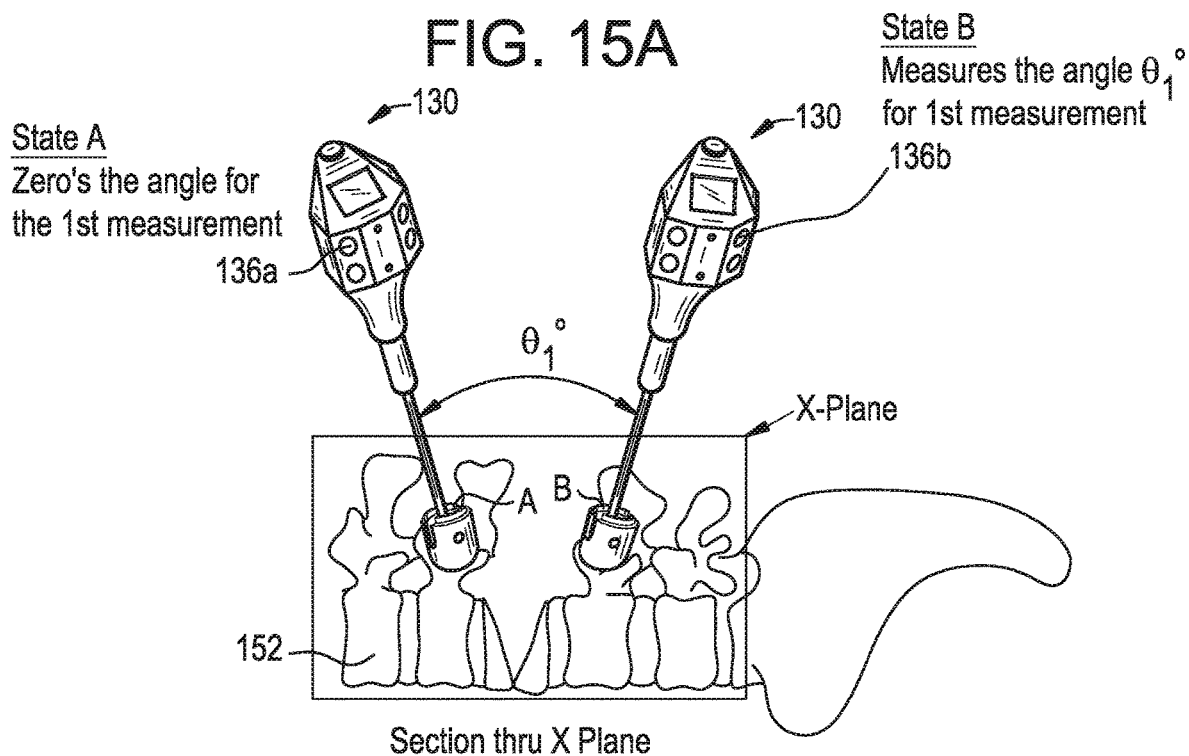
FIG. 15A is a schematic illustration of one embodiment of a surgical instrument with an electronic module measuring changes in position or orientation in a first plane prior to surgical manipulation.
Figure 15B:
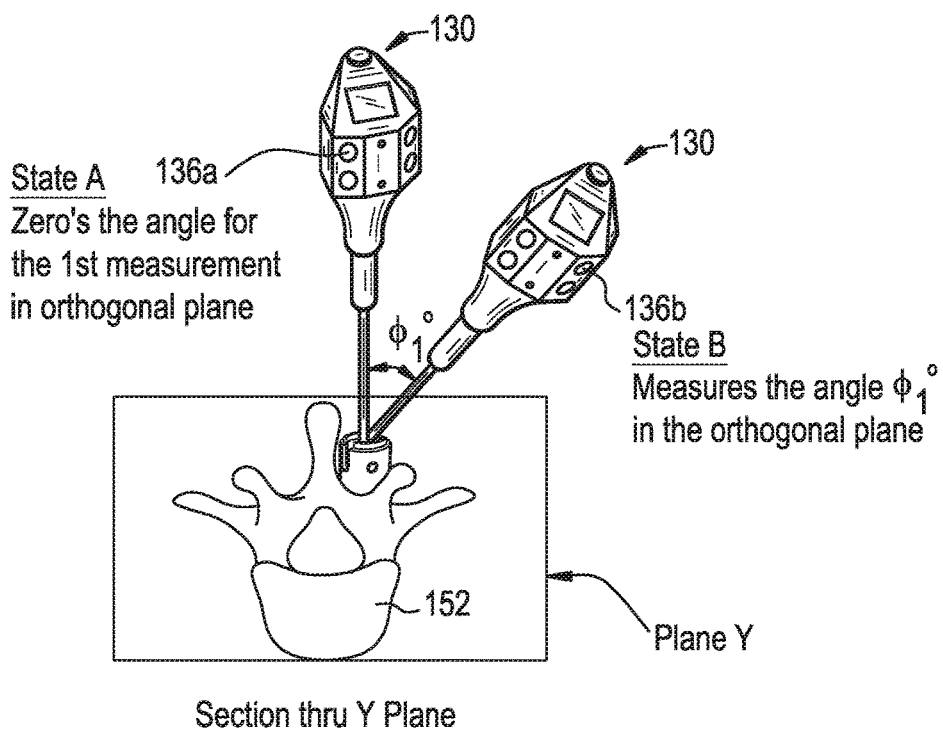
FIG. 15B is a schematic illustration of the surgical instrument of FIG. 15A measuring changes in position or orientation in a second plane orthogonal to the first plane prior to surgical manipulation.

FIG. 14B (referred to as "State B") illustrates a second button 136b that lights to indicate to a user to press this button for a next action. Prior to pressing the second button 136b, the instrument 130 can be moved to a new end point location. For example, in FIG. 15A the instrument is attached to the screw B in the new end point location. Pressing the second button 136b can allow the user to measure an angle between a start point location and this new end point location in two orthogonal planes (e.g., angles $\theta_1$ and $\varphi_1$ in planes X and Y, respectively, as shown in FIGS. 15A and 15B). The top-left of the display 138 can be updated with the measured angle 142 at the end point location (e.g., when the instrument 130 is attached to the screw B in FIG. 15A).

Figure 14C:
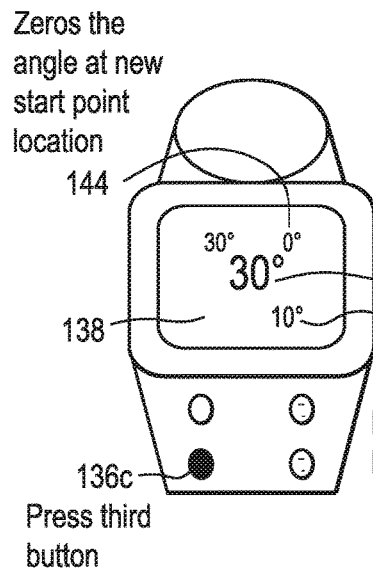
FIG. 14C is a schematic illustration of a third step in operating the electronic module of FIG. 14A.

FIG. 14C (referred to as "State C") illustrates a third button 136c that can be illuminated to indicate to a user to press this button for a next action. When a user has gone through an osteotomy closure during deformity correction, for example, they can take the sensor to the previous start point location (e.g., the position where the device 130 is in contact with the screw A shown in FIG. 15C). The third button can be pressed to zero the sensor at this location, as reflected by the display of 0° (ref. no. 144) in the upper right corner of the display 138.

Figure 14D:
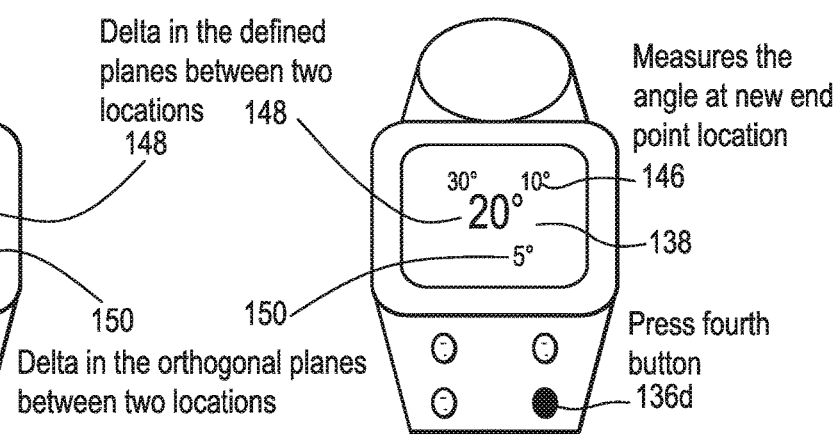
FIG. 14D is a schematic illustration of a fourth step in operating the electronic module of FIG. 14A.
Figure 15C:
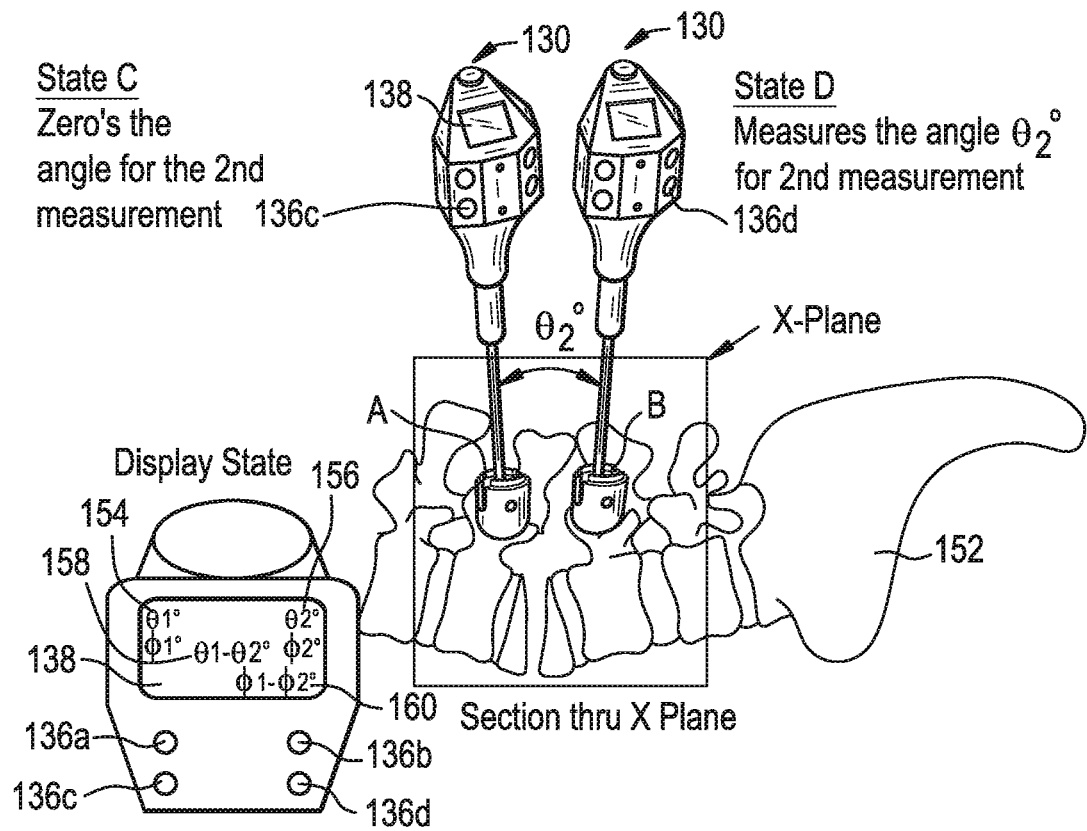
FIG. 15C is a schematic illustration of the surgical instrument of FIG. 15A measuring changes in position or orientation in the first plane after surgical manipulation.
Figure 15D:
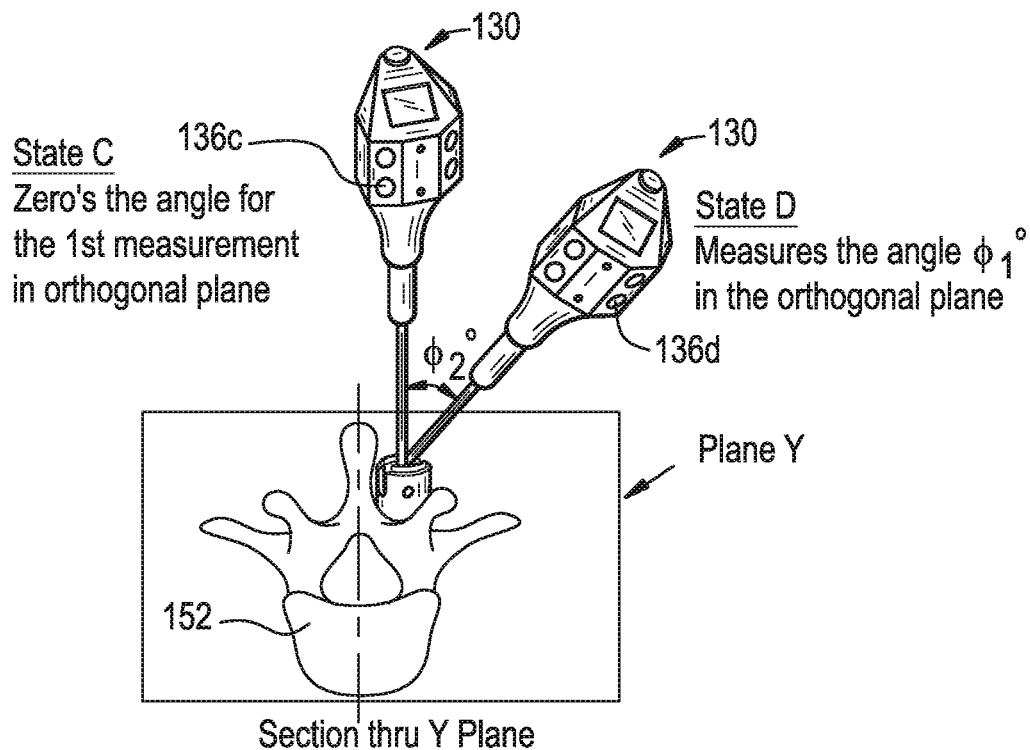
FIG. 15D is a schematic illustration of the surgical instrument of FIG. 15A measuring changes in position or orientation in the second plane after surgical manipulation.

The user can then move the sensor to the end point location (e.g., the position where the device 130 is in contact with screw B shown in FIG. 15C). A fourth button 136d can be lit indicating that the surgeon or other user can press it for a next action. Upon pressing the button 136d, as shown in FIG. 14D (referred to as "State D"), the top-right corner of the display 138 can be updated with a new measured angle 146 between the new start and end points in two orthogonal planes (e.g., angles $\theta_2$ and $\varphi_2$ in planes X and Y, respectively, as shown in FIGS. 15C and 15D). Furthermore, a first delta (e.g., $\theta_1-\theta_2$) 148 in the defined plane (Plane X) and a second delta ($\varphi_1$-$\varphi_2$) 150 in the orthogonal plane (Plane Y) can be updated indicating changes in the angular orientation of the original location (an initial location of a patient's anatomy, medical device, or implant before correction) with respect to the new locations (a final location of a patient's anatomy, medical device, or implant after correction).

Figure 14E:
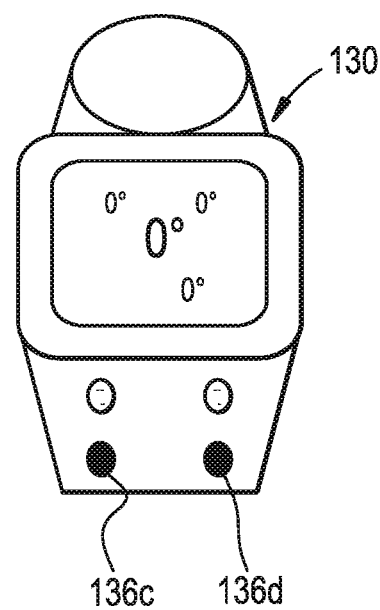
FIG. 14E is a schematic illustration of a resetting step in operating the electronic module of FIG. 14A.

In some embodiments, pressing any two buttons (e.g., 136c, 136d, etc.) together can instruct the system to reset all values and ready the device 130 for a new differential angular measurement, as shown in FIG. 14E (referred to as "State E").

In another embodiment, the device can allow for defining a projection plane, parallel to a gravitational field, between two locations with two depressions of a fifth button positioned at the center of the four buttons. Differential Measurements between any new locations can be displayed as projected angles in this newly defined projection plane (Plane X in FIGS. 15A-16) and a plane orthogonal to this defined projection plane (Plane Y in FIGS. 15A-16). For angular measurements, a similar workflow as outlined above for States A through E above can be used.

As noted above, FIGS. 15A-15D illustrate one example of how a device 130 with a four-button input or interface can be utilized to measure changes in position or orientation simultaneously in two orthogonal planes. As shown in the orthogonal section views of FIGS. 15A and 15B, the device 130 can be zeroed when in a first position where it is in contact with screw A by pressing the first button 136a. The device can then be moved to a second position where it is in contact with screw B and the second button 136b can be depressed. This can record the angle $\theta_1$ in the Plane X between the first and second positions, as well as the angle $\varphi_1$ between the first and second positions in the Plane Y (that is orthogonal to the Plane X).

Following surgical manipulation of the patient's anatomy 152, a second set of measurements can be made using the device 130. As shown in FIGS. 15C and 15D, the device 130 can be zeroed when in the first position where it is in contact with screw A by pressing the third button 136c. The device can then be moved to the second position where it is in contact with screw B and the fourth button 136d can be depressed. This can record the angle $\theta_2$ in the Plane X between the first and second positions, as well as the angle $\varphi_2$ between the first and second positions in the Plane Y (that is orthogonal to the Plane X).

The display 138 of the device 130 can communicate measured and calculated position or orientation data to a user. As shown in FIG. 15C, for example, the display 138 can include the angles $\theta_1$ and $\varphi_1$ in an upper left corner 154, the angles $\theta_2$ and $\varphi_2$ in an upper right corner 156, the delta $\theta_1$-$\theta_2$ in the center 158, and the delta $\varphi_1$-$\varphi_2$ in the lower right corner 160. The positioning of the information on the display 138 can be different in alternative embodiments, and any of a variety of types of information in different display formats can be communicated to a user.

Figure 16:
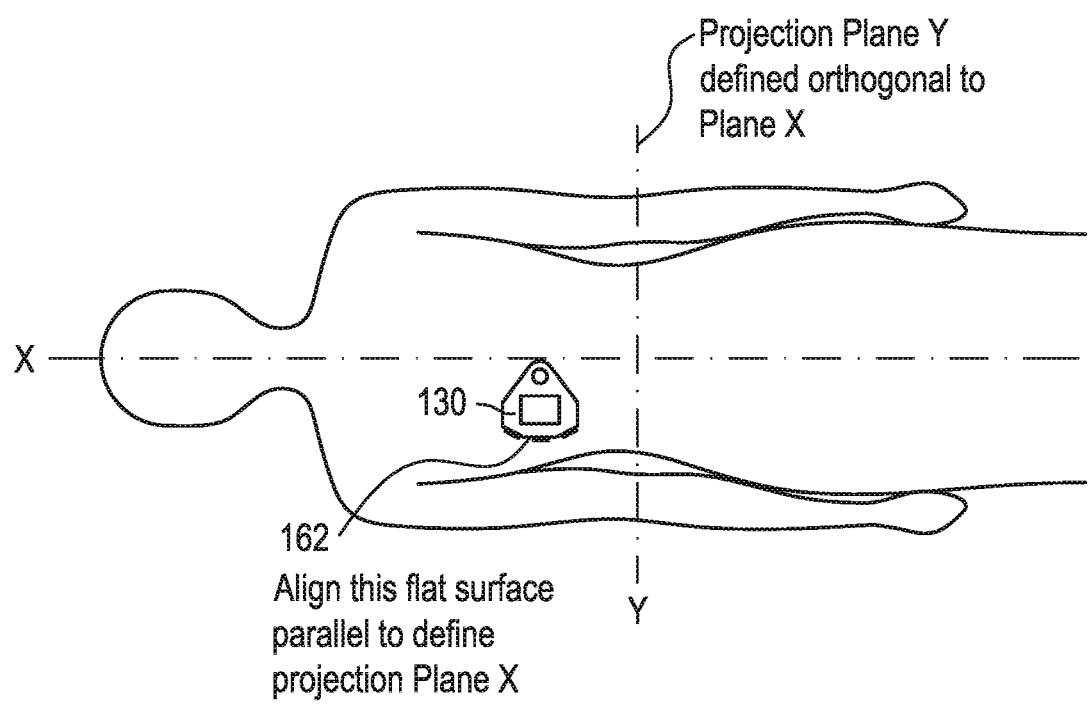
FIG. 16 is a schematic illustration of one embodiment of a surgical instrument defining first and second orthogonal projection planes in which to measure changes in position or orientation.

FIG. 16 illustrates the instrument 130 from a top view and highlights that the instrument can include a reference plane alignment feature 162 to aid a user in defining the reference plane (Plane X in the figure) and the orthogonal plane (Plane Y in the figure). In the illustrated embodiment, a flat surface on a side of the instrument 130 can serve as the reference plane alignment feature that can be oriented parallel to the reference plane (Plane X). In other embodiments, a marking, recess, protrusion, or other feature can be utilized, as described above. Further, in some embodiments an additional marking or feature can be included to denote the orientation of the orthogonal plane (Plane Y in the figure).

The above-described embodiments can have a number of advantages over prior devices and techniques. For example, the devices and methods described herein can provide an instrument for intraoperatively measuring anatomical orientation that can be easy to use and can be independent of a wirelessly (e.g., Wi-Fi®, Bluetooth®, etc.) or otherwise remotely-connected tablet or display. Moreover, there is currently no quick way to measure sagittal balance and regional curves intraoperatively during deformity and degenerative surgeries. Many prior techniques involve taking fluoro-images, sending them to a PACs (Picture Archiving and Communication) system, and using the images to measure correction using a manual protractor. This type of technique can require a surgeon to leave a sterile field, which is not desirable and can increase surgery time. In one embodiment, a device according to the teachings provided herein can be coupled to any medical device, tool, or instrument that can be aligned with two endplates at the apex of the desired curves by means of fluoro-images to measure starting lordosis or kyphosis plus scoliosis angles simultaneously as soon as patient is placed on the operating table. This can be advantageous because placing a patient prone on a table can change their regional curve. Surgeons are often interested in knowing this angle and registering it as reference starting point. All further corrections and improvements in sagittal balance, as well as subsequent changes in regional angular values, can be measured relative to this reference point using, for example, the third and fourth buttons 136c, 136d of the device described above. For example, the steps shown in FIGS. 14C, 14D, 15C, and 15D can be repeated as a surgeon or other user manipulates a patient's anatomy and measurements can be taken relative to the original starting positions recorded as shown in FIGS. 14A, 14B, 15A, and 15B.

The above described devices and methods can be utilized for a number of different procedures, including, for example, as a tool for measuring angular orientation of a portion of a patient's anatomy, an osteotome with angular orientation sensing capability, a tool for pedicle targeting, and a tool for rod bending, among others. These devices can provide surgeons with an ability to intraoperatively measure spinal correction achieved at each regional curve, including lordosis, kyphosis, and scoliosis. Further, devices and methods described herein can provide an association between correction achieved in a standing and a prone position, as well as an ability to provide coronal correction measurement. Such methods and devices can aid surgeons in achieving coronal alignment, shoulder and pelvic leveling during complex deformity correction procedures, and can provide degeneration and minimally invasive procedure surgeons with tools to intraoperatively monitor spinal alignment.

The devices and methods described herein can provide such functionality while minimizing sensor size and reducing visual obstruction to a surgeon. This can provide surgeons with real-time regional curve and osteotomy closure angle measurement without compromising workflow or visualization. Furthermore, the devices described herein can make use of wired or wireless components (e.g., wired components can in some cases be made smaller than wireless components, further reducing the size of a device). The methods described herein can provide quick, simple to use, low profile, and easy to connect components that can be used with a surgeon's existing tools. This can allow surgeons to quickly validate angles utilizing their existing instrumentation to achieve consistent surgical outcomes. Further, the devices described herein can include a variety of user interfaces, including a digital display, a single button, four buttons, five buttons, or another configuration. The devices described herein can be configured to couple to bone cutting tools, taps, Lenke probes, osteotomy closure clamps, harmonic tools, or rod benders. The devices and methods described herein could also be configured for use with lordotic cages to confirm achievement of proper angular correction at a particular level.

Moreover, the devices described herein can be incorporated into a modular handle that can be moved between various surgical instruments. This can allow the devices and methods described herein to be utilized in connection with other deformity, degenerative, and minimally invasive surgery (MIS) applications.

Exemplary features of the devices and methods described herein can include a disposable integrated handle with an angle sensor, a built-in display, and a low profile easy to connect feature for mating with existing surgical instruments. Such a device can allow a surgeon to intraoperatively measure actual regional angles after aligning a tool with respective end plates, or measure a change in angles projected on to any two orthogonal planes. A free-hand tool according to the teachings provided herein can be used to validate osteotomy wedge angles, enable accurate bone removal (as in osteotomies), target trajectory for pedicle screws, mirror trajectory for pedicle screws, and bend spinal rods.

Figure 17A:
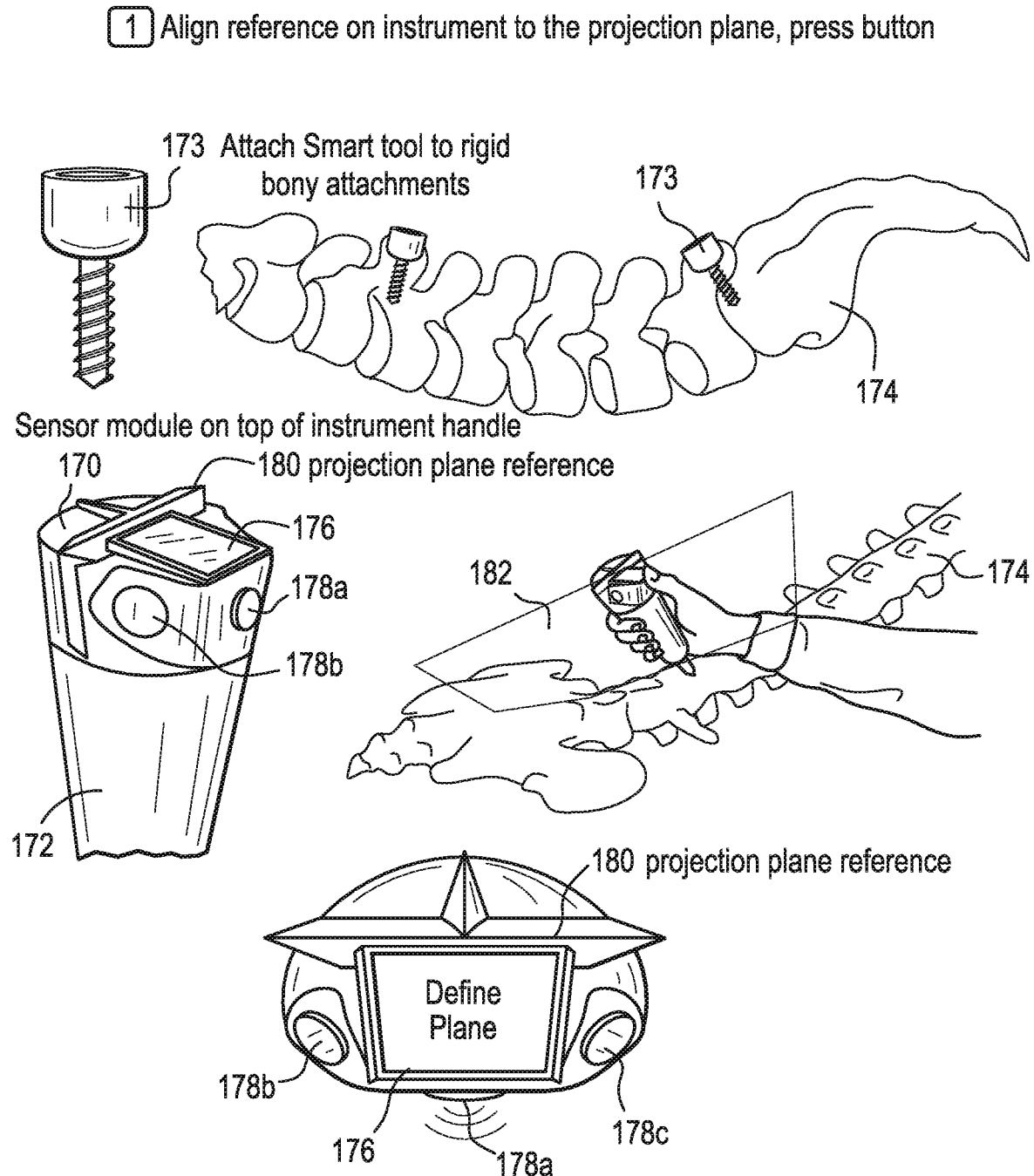
FIG. 17A is a schematic illustration of one embodiment of a surgical instrument defining a projection plane prior to surgical manipulation.

Further illustration of embodiments of the devices and methods described herein is shown in FIGS. 17A-22B. FIGS. 17A-17G, for example, illustrate one embodiment of a method of operation of an instrument for intraoperatively measuring anatomical orientation having a three-button input interface. FIG. 17A, for example, illustrates coupling of an electronic module 170 to an instrument 172 and positioning of the instrument 170 such that it is in contact with a pedicle screw or other rigid bony attachment 173 that can be implanted in, for example, a patient's spine 174. The module 170 can include a display 176, an input 178 including three buttons 178a, 178b, 178c, and a reference plane alignment feature 180. In the illustrated step of the method, the instrument 172 with electronic module 170 coupled thereto can be positioned at a first point in contact with the pedicle screw 173 or a portion of the patient's anatomy and the reference plane alignment feature 180 can be aligned with the desired reference plane (e.g., a patient's sagittal plane) into which measured angles can be projected. The first button 178a, which can be illuminated to prompt a user in connection with, for example, a prompt on the display 176, can be depressed to record the current position and/or orientation and define the reference plane.

Figure 17B:
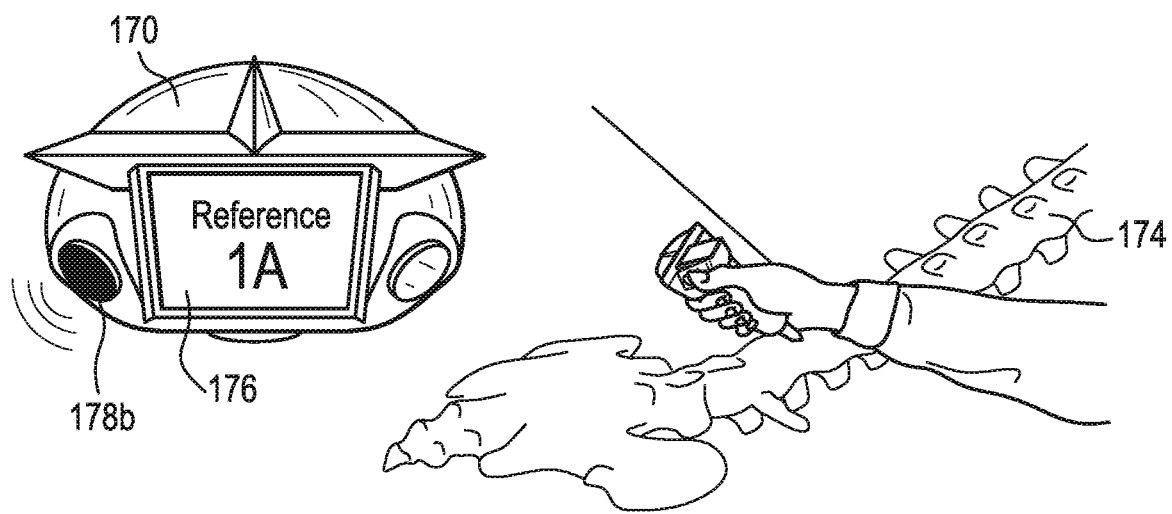
FIG. 17B is a schematic illustration of the surgical instrument of FIG. 17A recording position or orientation information at a first point prior to surgical manipulation.
Figure 17C:
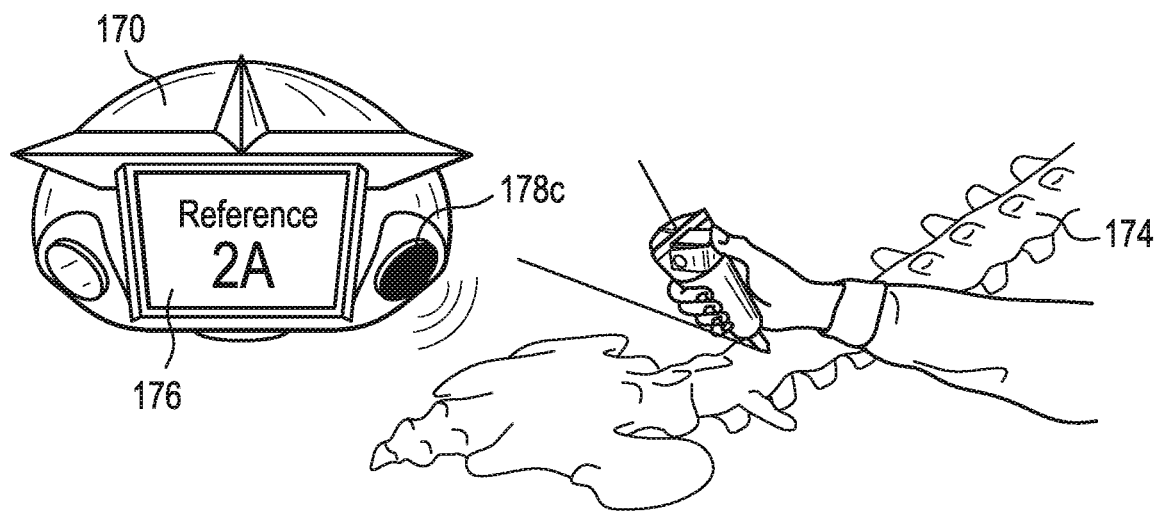
FIG. 17C is a schematic illustration of the surgical instrument of FIG. 17A recording position or orientation information at a second point prior to surgical manipulation.

FIG. 17B illustrates another step in which the instrument is moved to a first position and the second button 178b (which can be illuminated to prompt a user after the first button 178a is depressed to define the reference plane) can be depressed to record the current position and/or orientation at the first position. In another step illustrated in FIG. 17C, the instrument 172 can be moved to a second position and the third button 178c (which can be illuminated to prompt a user after the second button 178b is depressed to define the first position) can be depressed to record the current position and/or orientation at the second position. A processor included in the electronic module 170 can then calculate angular differences between the position or orientation of the instrument 172 in the first and second positions, as projected onto the reference plane and a plane orthogonal thereto. This measurement can serve as a baseline or pre-manipulation reference.

Figure 17D:
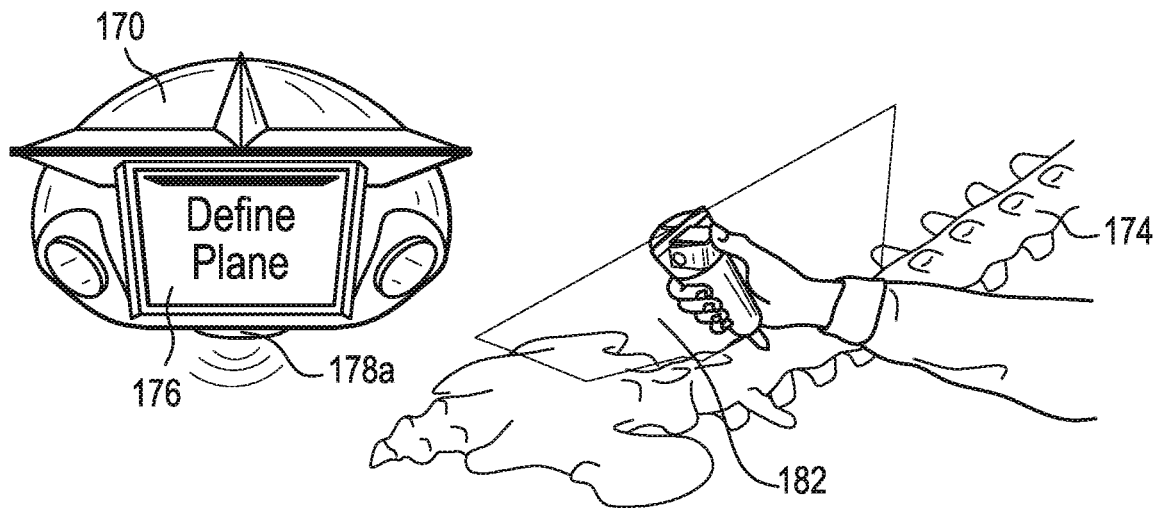
FIG. 17D is a schematic illustration of the surgical instrument of FIG. 17A defining a projection plane after surgical manipulation.
Figure 17E:
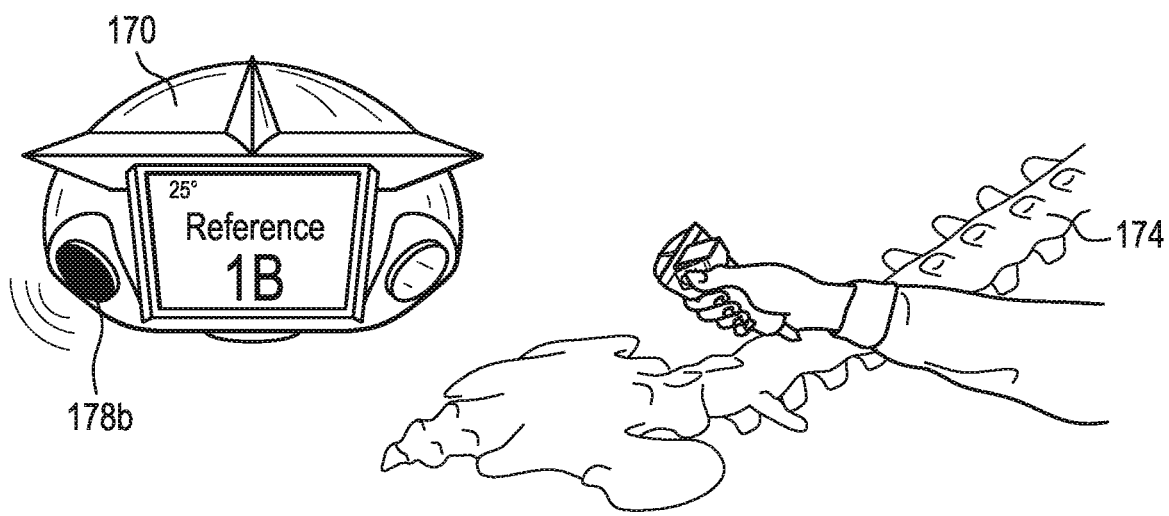
FIG. 17E is a schematic illustration of the surgical instrument of FIG. 17A recording position or orientation information at the first point after surgical manipulation.
Figure 17F:
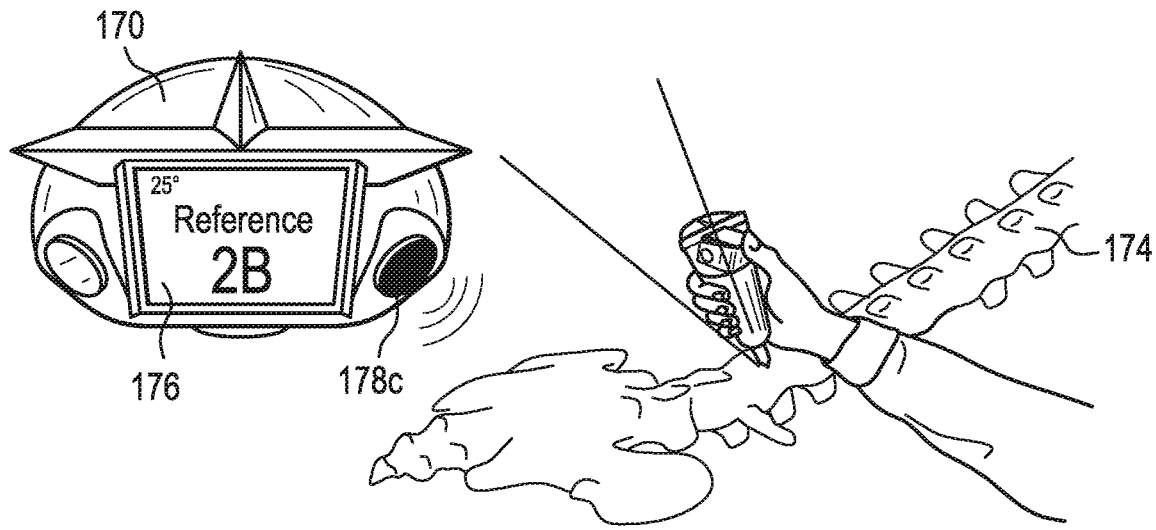
FIG. 17F is a schematic illustration of the surgical instrument of FIG. 17A recording position or orientation information at the second point after surgical manipulation.
Figure 17G:
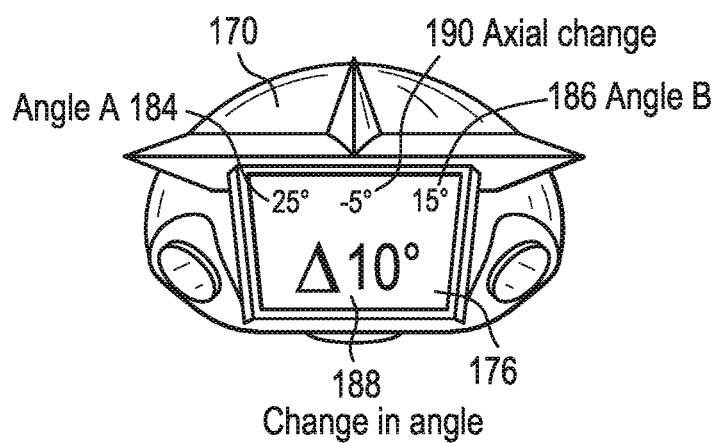
FIG. 17G is a schematic illustration of the surgical instrument of FIG. 17A displaying calculated position or orientation data after surgical manipulation.

Following surgical manipulation of the patient's anatomy (e.g., spine 174), the measurement process can be repeated as shown in FIGS. 17D-17F. In particular, the reference plane can be redefined using the first button 178a, as shown in FIG. 17D. In addition, position and/or orientation information can be captured at the first position using the second button 178b, as shown in FIG. 17E, and position and/or orientation information can be captured at the second position using the third button 176c, as shown in FIG. 17F. The processor of the module 170 can then communicate measured and calculated information to a user via the display 176, including a first angle 184 measured between the first and second positions before surgical manipulation and a second angle 186 measured between the first and second positions after surgical manipulation, as well as a delta 188 between those angles, as shown in FIG. 17G. These angles can be projected into the defined reference plane 182 and a further angle 190 can be included representing change in a plane orthogonal to the reference plane 182.

Figure 18A:
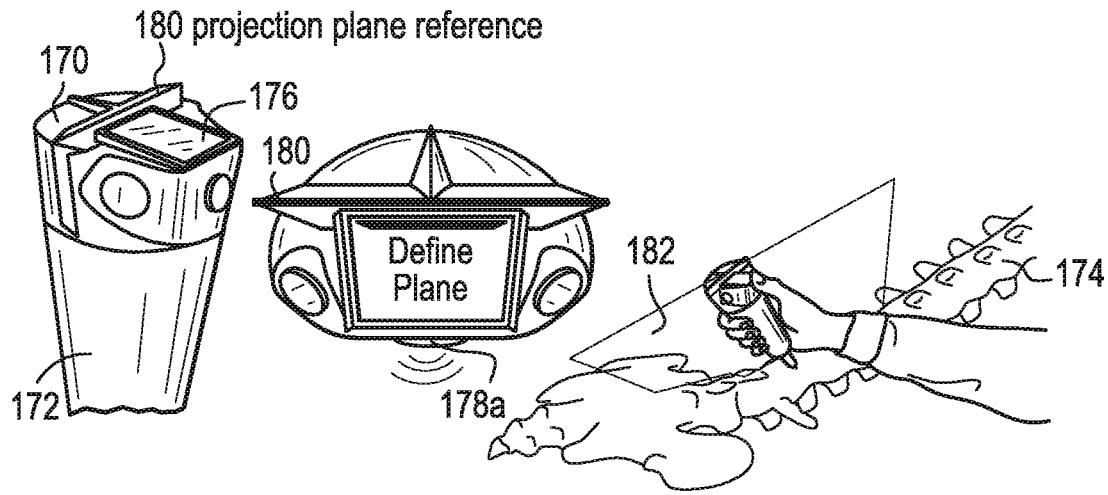
FIG. 18A is a schematic illustration of one embodiment of a surgical instrument defining a projection plane prior to surgical manipulation.
Figure 18B:
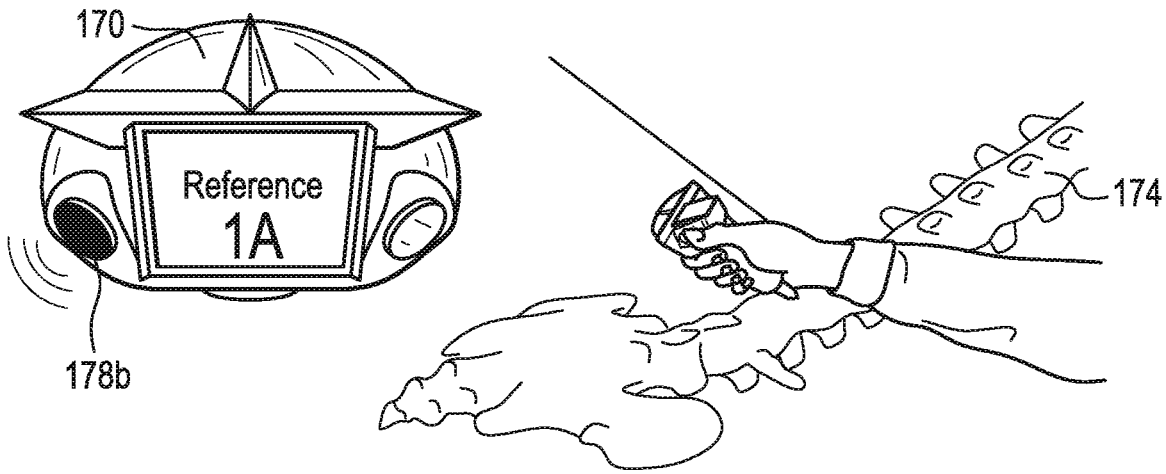
FIG. 18B is a schematic illustration of the surgical instrument of FIG. 18A recording position or orientation information at a first point prior to surgical manipulation.
Figure 18C:
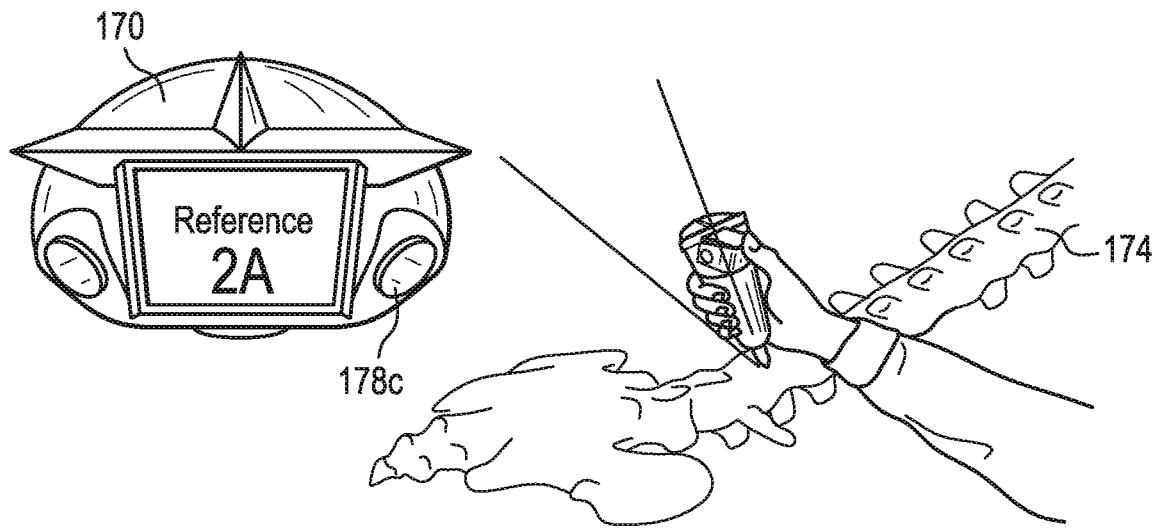
FIG. 18C is a schematic illustration of the surgical instrument of FIG. 18A recording position or orientation information at a second point prior to surgical manipulation.
Figure 18D:
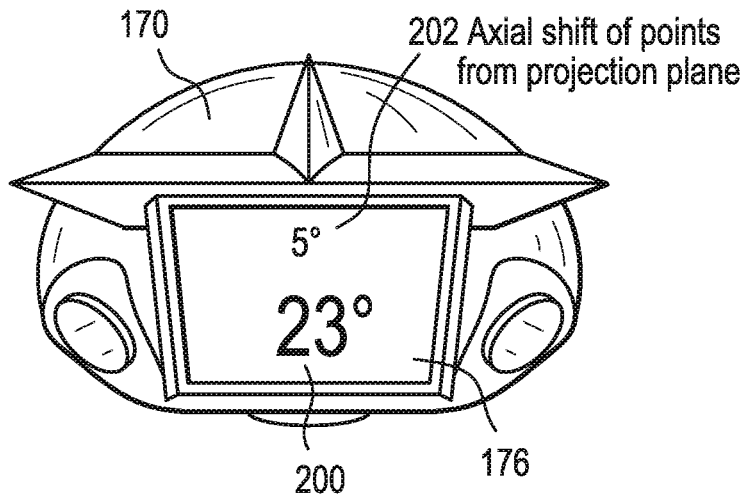
FIG. 18D is a schematic illustration of the surgical instrument of FIG. 18A displaying calculated position or orientation data prior to surgical manipulation.

FIGS. 18A-18J illustrate another embodiment of a method of operation of an instrument for intraoperatively measuring anatomical orientation having a three-button interface. The method is similar to the method described above and shown in FIGS. 17A-17G, but illustrates additional features that can be provided in various embodiments. For example, FIGS. 18A-18C illustrate a similar process for defining a reference plane (and a plane orthogonal thereto) and recording position and/or orientation information at first and second reference positions prior to surgical manipulation of a patient's anatomy. FIG. 18D illustrates that, in some embodiments, initial measured or calculated position and/or orientation data can be immediately displayed to a user. Such information can include, for example, the angle 200 between the first and second reference points as projected into the reference plane, as well as the angle 202 between the first and second reference points as projected into the plane orthogonal to the reference plane.

Figure 18E:
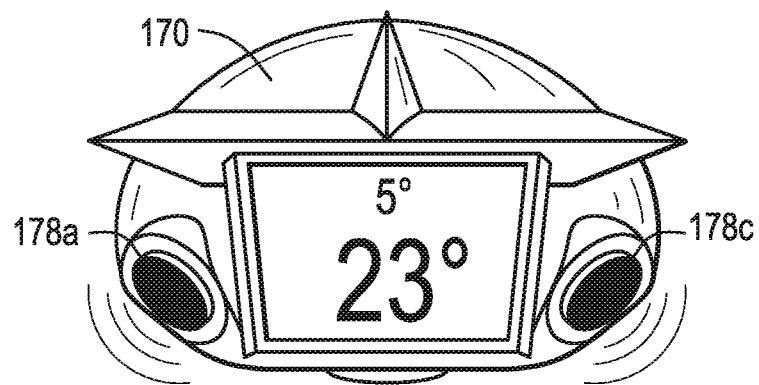
FIG. 18E is a schematic illustration of the surgical instrument of FIG. 18A saving calculated position or orientation data displayed in FIG. 18D.
Figure 18F:
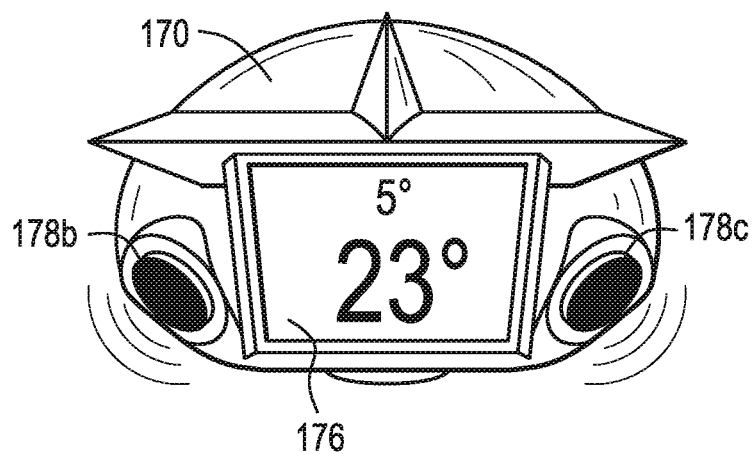
FIG. 18F is a schematic illustration of the surgical instrument of FIG. 18A recalling calculated position or orientation data displayed in FIG. 18D.
Figure 18G:
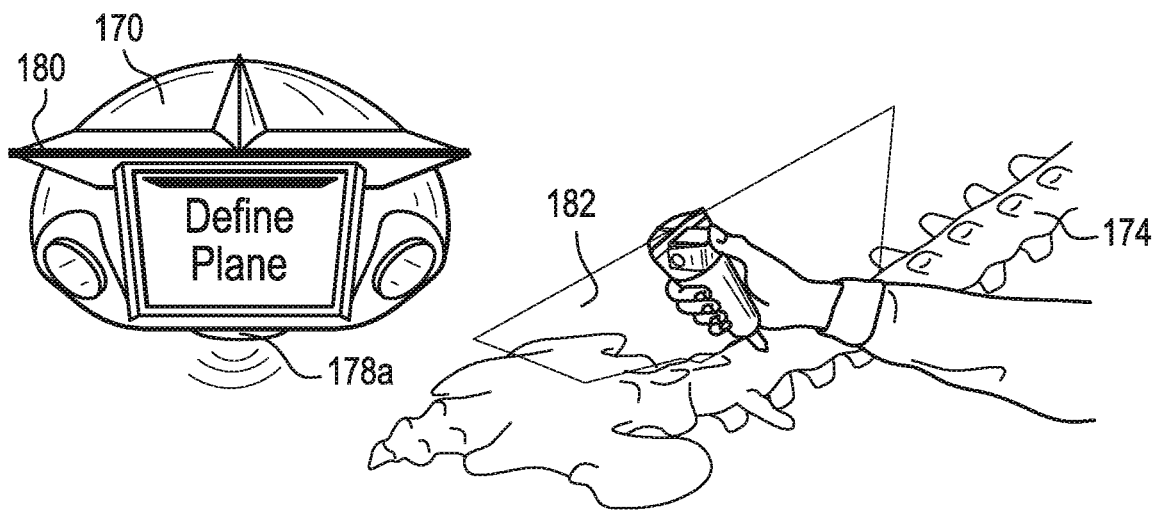
FIG. 18G is a schematic illustration of the surgical instrument of FIG. 18A defining a projection plane after surgical manipulation.
Figure 18H:
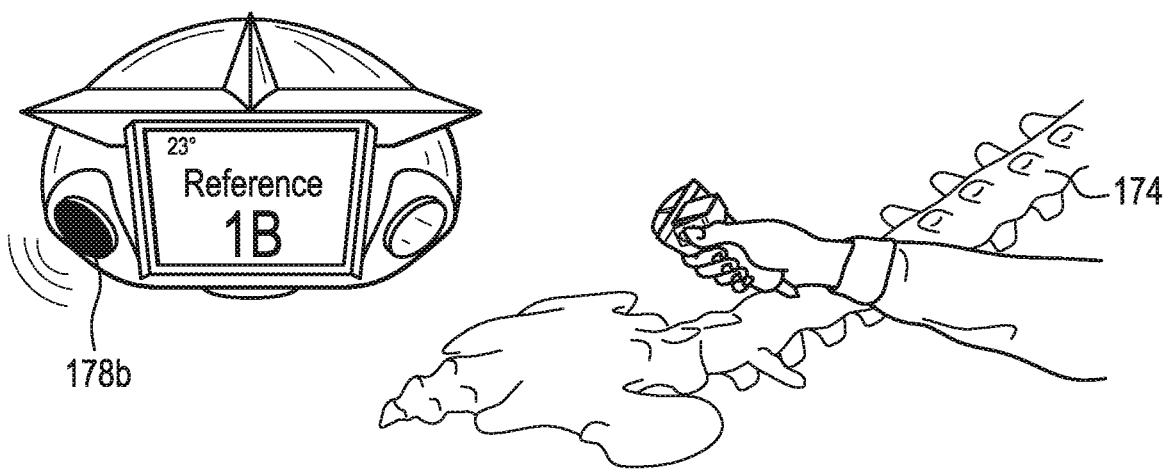
FIG. 18H is a schematic illustration of the surgical instrument of FIG. 18A recording position or orientation information at the first point after surgical manipulation.
Figure 18I:
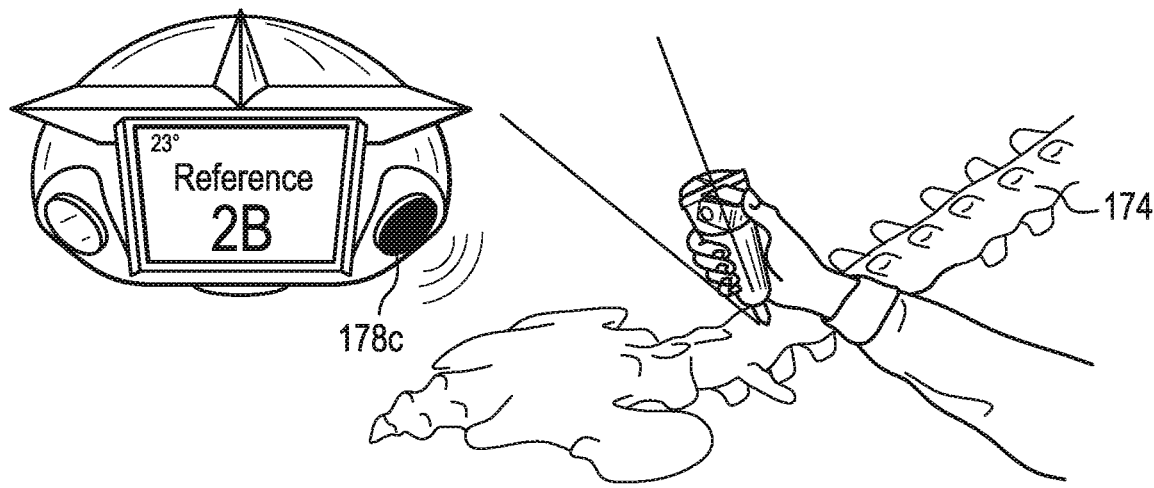
FIG. 18I is a schematic illustration of the surgical instrument of FIG. 18A recording position or orientation information at the second point after surgical manipulation.

In FIG. 18E, a step of simultaneously pressing the second button 178c and the third button 178c to save the captured information is illustrated. Alternatively, a user could re-take the measurements of FIGS. 18A-C if, for example, the instrument was improperly positioned, etc. As shown in FIG. 18F, at subsequent times the saves data can be recalled to the display 176 by simultaneously pressing the second and third buttons 178b, 178c again.

Figure 18J:
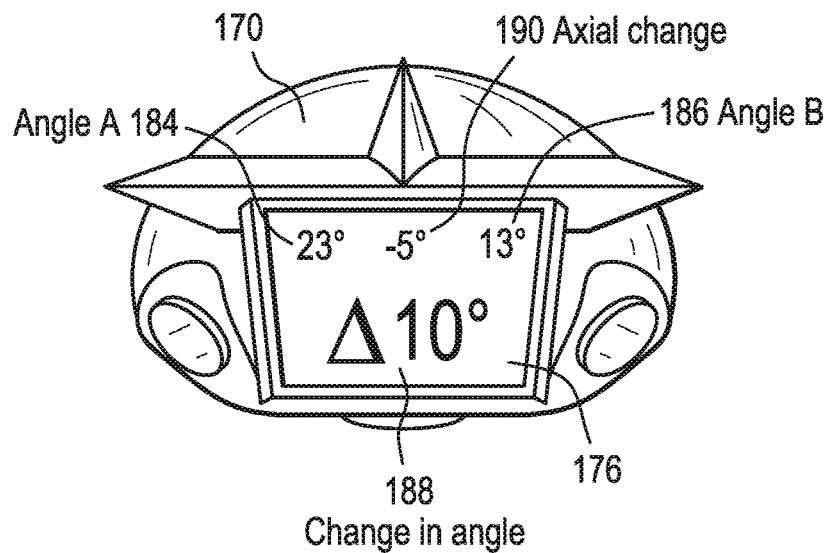
FIG. 18J is a schematic illustration of the surgical instrument of FIG. 18A displaying calculated position or orientation data.

FIGS. 18G-18J illustrate method steps similar to those described above and illustrated in FIGS. 17D-G that can be performed following surgical manipulation of a patient's anatomy 174. These can include redefining the reference plane (FIG. 18G), capturing data from the first and second positions (FIGS. 18H and 18I), and displaying measured and calculated position and/or orientation data to a user via the display 176 (FIG. 18J).

Figure 19A:
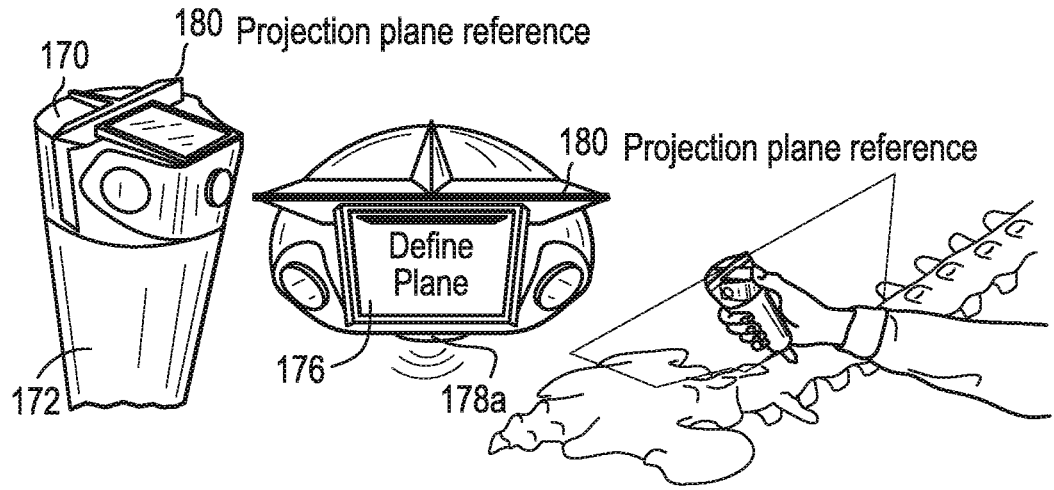
FIG. 19A is a schematic illustration of one embodiment of a surgical instrument defining a projection plane.
Figure 19B:
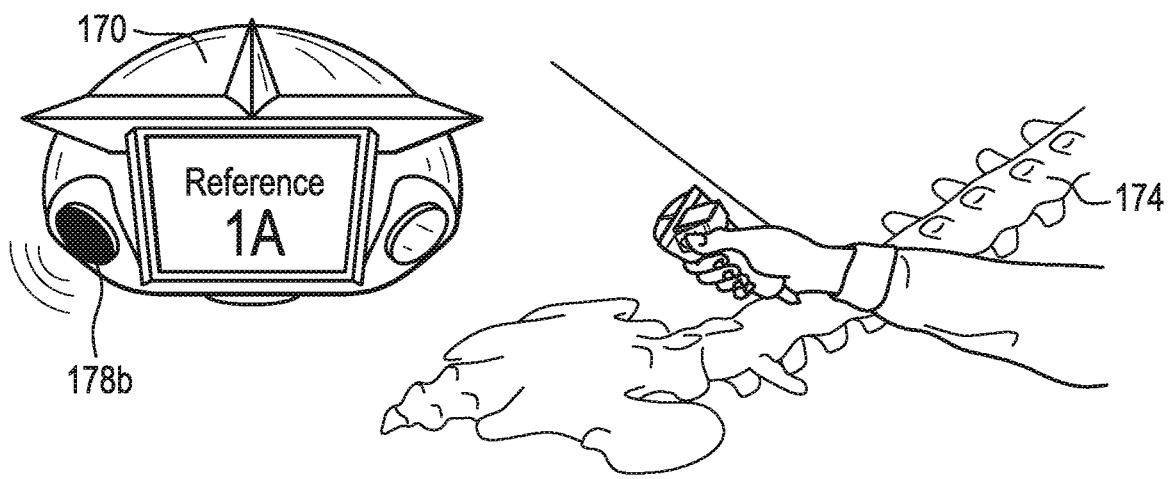
FIG. 19B is a schematic illustration of the surgical instrument of FIG. 19A recording position or orientation information at a first point.
Figure 19C:
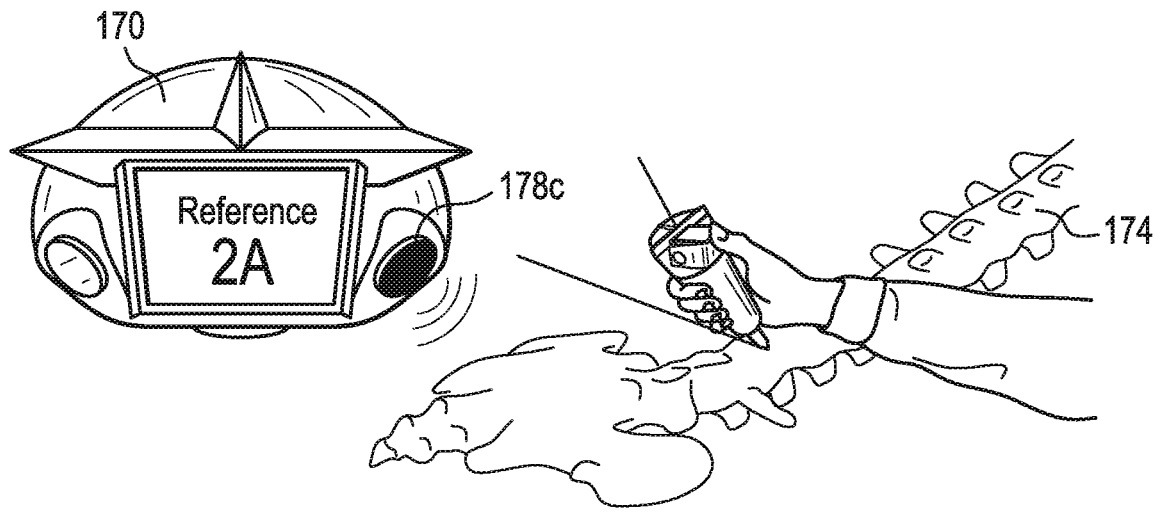
FIG. 19C is a schematic illustration of the surgical instrument of FIG. 19A recording position or orientation information at a second point.
Figure 19D:
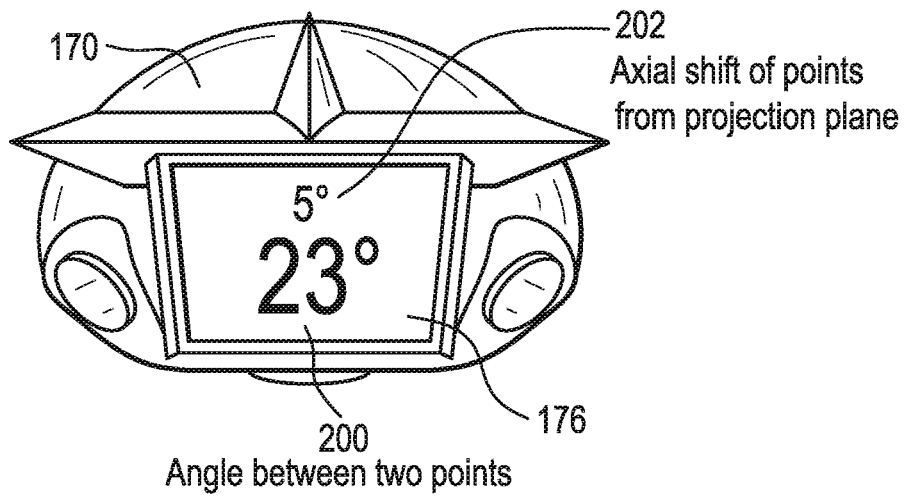
FIG. 19D is a schematic illustration of the surgical instrument of FIG. 19A displaying calculated position or orientation data.

FIGS. 19A-19D illustrate still another embodiment of a method of operation of an instrument for intraoperatively measuring anatomical orientation having a three-button interface. In this embodiment, the electronic module 170 and instrument 172 can be utilized without pre- and post-manipulation measurement comparisons to measure position and/or orientation changes between two reference points at any time. The method illustrated in FIGS. 19A-19D mirrors that described above and illustrated in FIGS. 18A-18D. For example, the method can include defining a reference plane into which angles can be projected (FIG. 19A), capturing position and/or orientation data at a first position (FIG. 19B) and a second position (FIG. 19C) and displaying measured or calculated data to a user (FIG. 19D). The displayed data can include, for example, a first angle 200 between the first and second reference positions measured in the reference plane and a second angle 202 between the first and second reference positions measured in a plane orthogonal to the reference plane.

FIG. 20A-20D illustrate one embodiment of a method of operating an osteotome 210 with a disposable sensor pod or module 212 that can be selectively coupled thereto. In particular, a housing 214 of the module 212 can include one or more engagement features 216 configured to interface with complementary features on the osteotome 210 (or other surgical instrument) to removably attach the housing thereto. Examples of engagement features 216 can include a protrusion, recess, latch, or other feature.

The module 212 can include a single button input 218 that can be used to operate the module in a manner similar to the method described above and illustrated in FIGS. 9A-12. In the illustrated embodiment, the module 212 includes a different type of display 220 that conveys first angle information 222 related to a reference plane and second angle information 224 related to a plane orthogonal to the reference plane using two illuminated indicators oriented orthogonally to one another.

Figure 20D:
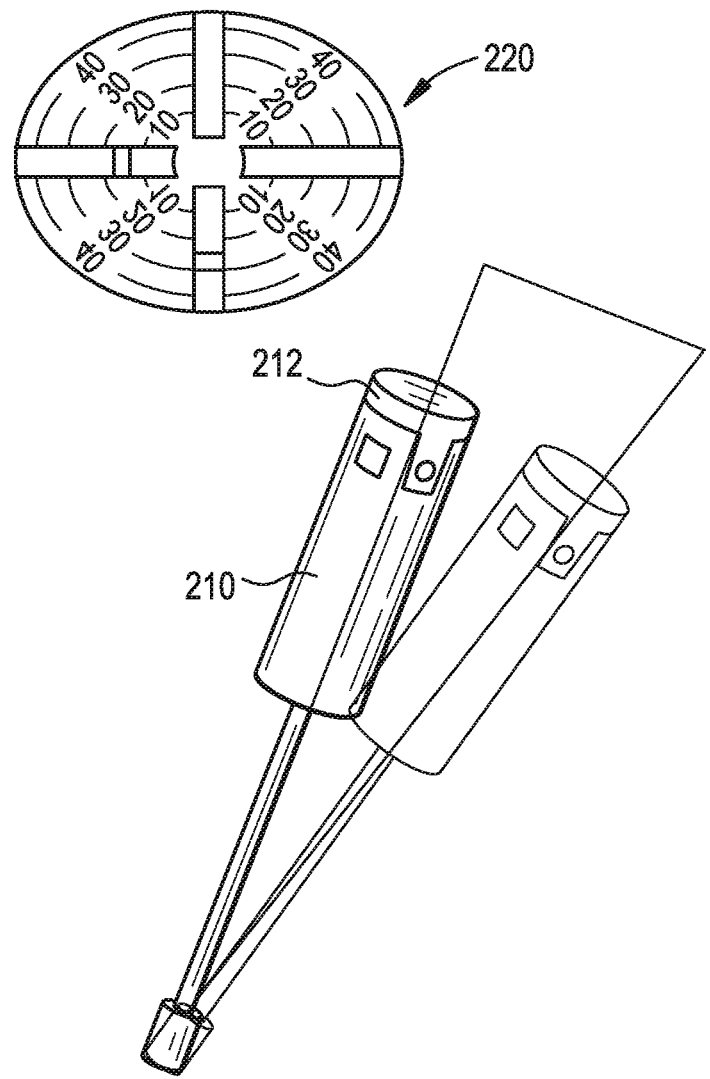
FIG. 20D is a schematic illustration of the electronic module and surgical instrument of FIG. 20A at a second position or orientation measuring a relative change from the first position or orientation.

FIGS. 20B-20D illustrate one example of a method of operating the module 212. Similar to the methods described above, the illustrated method can include positioning the osteotome in a first orientation, zeroing a display of orientation relative to gravity, moving the osteotome to a second orientation, and displaying a change in orientation relative to the first orientation. More particularly, as shown in FIG. 20B the osteotome 210 can be placed in a first reference position and the module 212 can indicate an initial angular orientation relative to gravity or the earth. A user can press the input button 218, as shown in FIG. 20C, to zero the module 212 when in the first reference position. The user can then move the osteotome 210 to a second reference position, as shown in FIG. 20D, and read the angular indications from the display 220 that are now shown relative to the first reference position.

Figure 21A:
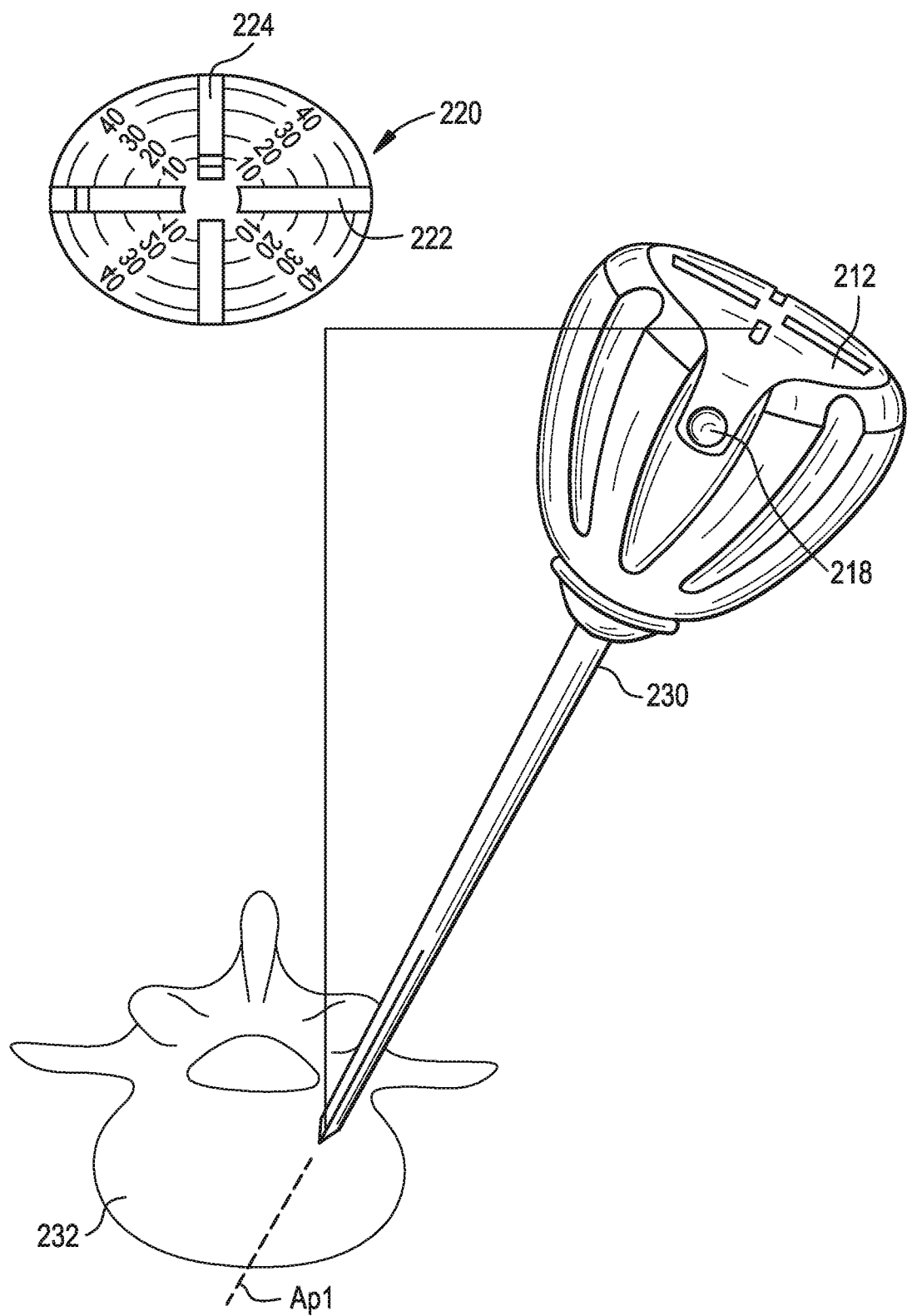
FIG. 21A is a schematic illustration of one embodiment of a surgical instrument recording a first pedicle screw trajectory.
Figure 21B:
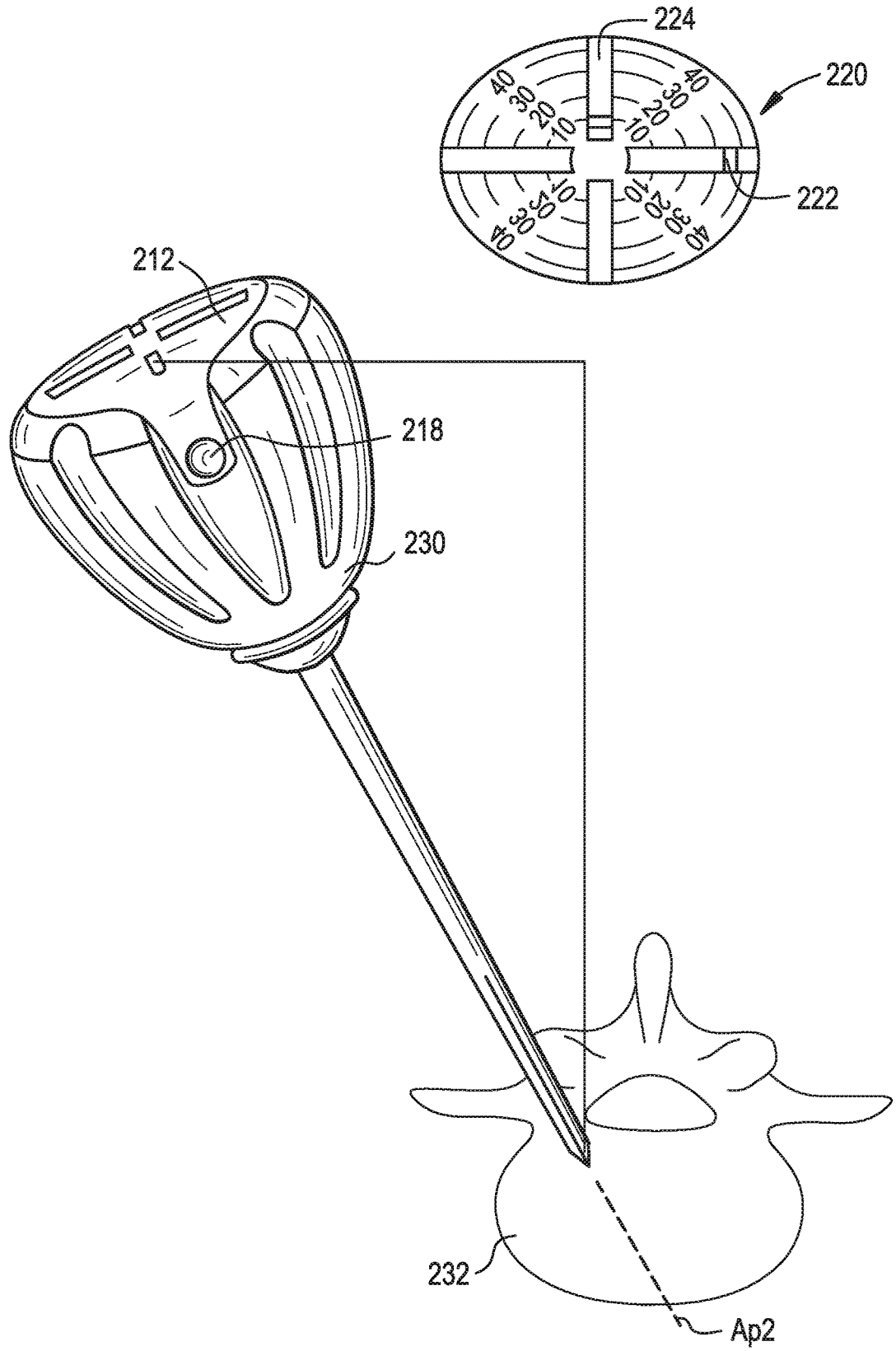
FIG. 21B is a schematic illustration of the surgical instrument of FIG. 21A aligned at a second pedicle screw trajectory that mirrors the first pedicle screw trajectory.

FIGS. 21A-21B illustrate one embodiment of a tool 230 that can be used in conjunction with the module 212 to determine pedicle screw trajectory. As shown in FIG. 21A, the tool 230 can be aligned with an axis of a first pedicle screw $A_{p1}$ being inserted into a patient's vertebra 232 and can record its position and/or orientation, e.g., by depressing the button 218. Angles measured relative to a reference plane and a plane orthogonal thereto can be displayed on the display 220 using the illuminated indicators 222, 224. The tool can then be utilized to determine a mirroring pedicle axis $A_{p2}$ orientation on an opposite side of a patient's vertebra 232, as shown in FIG. 21B. For example, a user can adjust a position of the tool 230 until the display 220 has a matching angular displacement readout, or the module 212 can be configured to flash the indicators 222, 224 or otherwise communicate feedback to a user when the position and/or orientation mirrors the orientation recorded as shown in FIG. 21B. The tool 230 and module 212 can thereby provide for symmetric insertion of pedicle screws on opposite sides of the spine. This can create an additional benefit of permitting similarly formed spinal fixation elements, such as spinal fixation rods, to be utilized on both sides of the patient's spine. Eliminating time spent customizing rod shape on each side of the spine can greatly increase the efficiency of a surgeon or other user by reducing complexity and time for a spinal correction procedure.

Figure 22A:
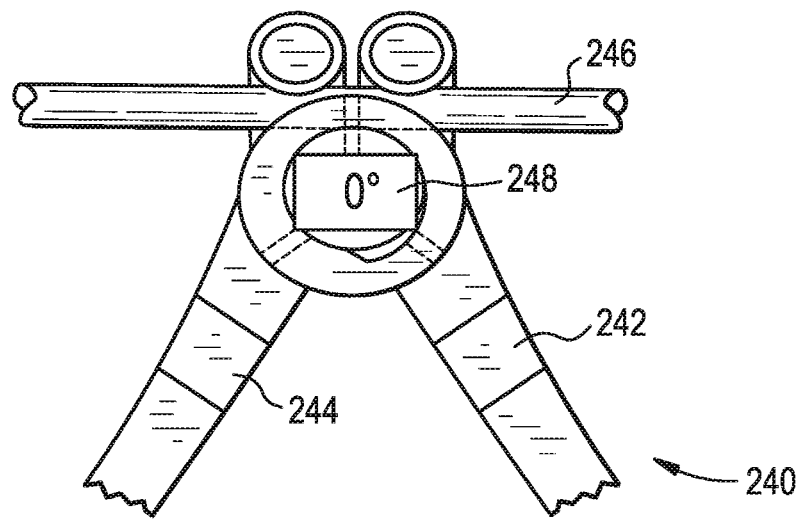
FIG. 22A is a schematic illustration of one embodiment of a surgical instrument for spinal rod bending in a first position.
Figure 22B:
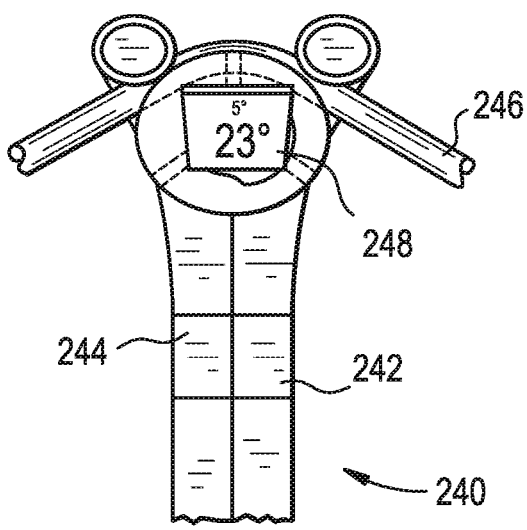
FIG. 22B is a schematic illustration of the surgical instrument of FIG. 22A in a second position and displaying position or orientation change from the first position.

FIGS. 22A-22B illustrate another embodiment in which sensors 242, 244 are coupled to a tool 240 used to bend a spinal fixation rod 246. The sensors 242, 244 can detect an angle of bend imparted to the rod 246 by the tool 240, and this angle can be displayed to a user on a display 248 coupled to the tool. In other embodiments described in more detail below, the sensors 242, 244 can be coupled to the rod 246 directly to detect a degree of bend imparted thereto in one or more planes.

Figure 23:
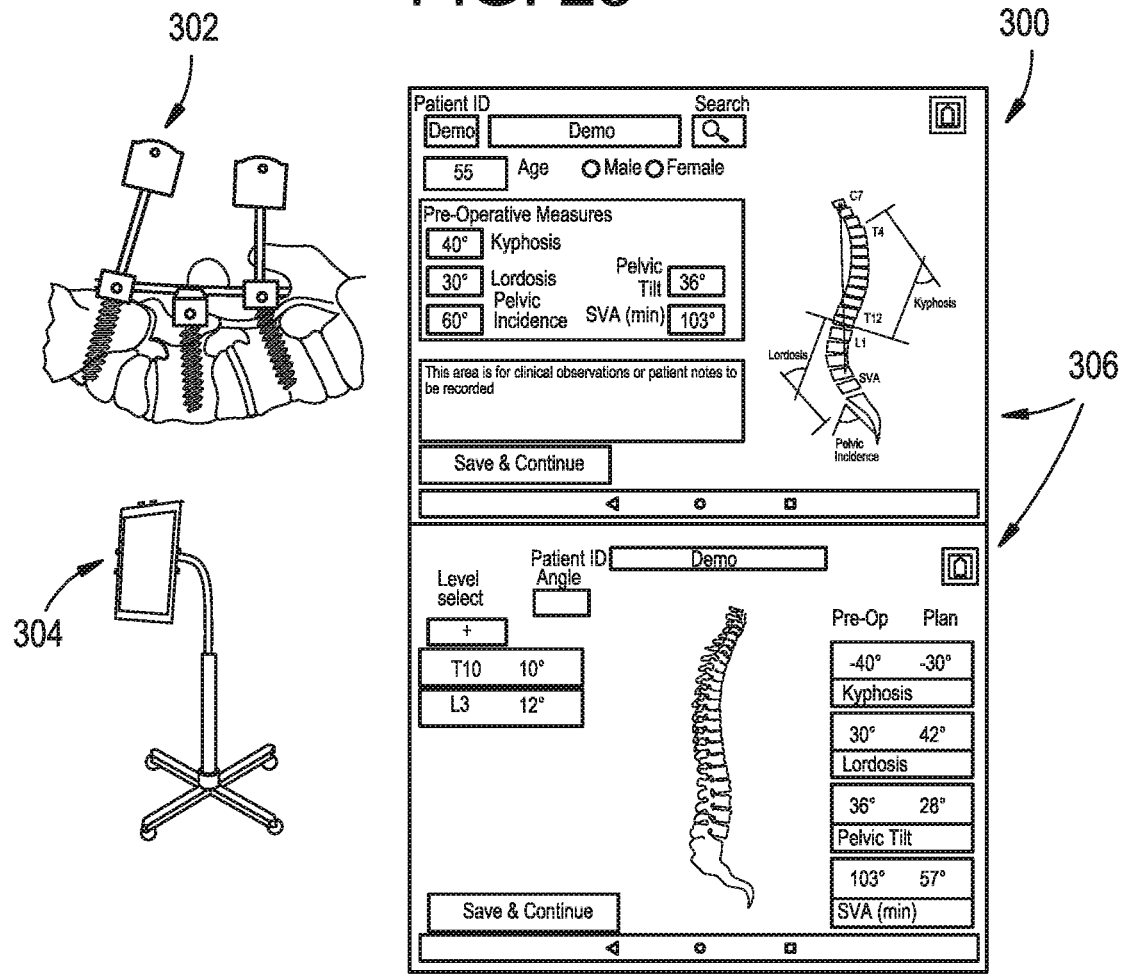
FIG. 23 is a schematic illustration of one embodiment of a surgical system according to the teachings provided herein.
Figure 24:
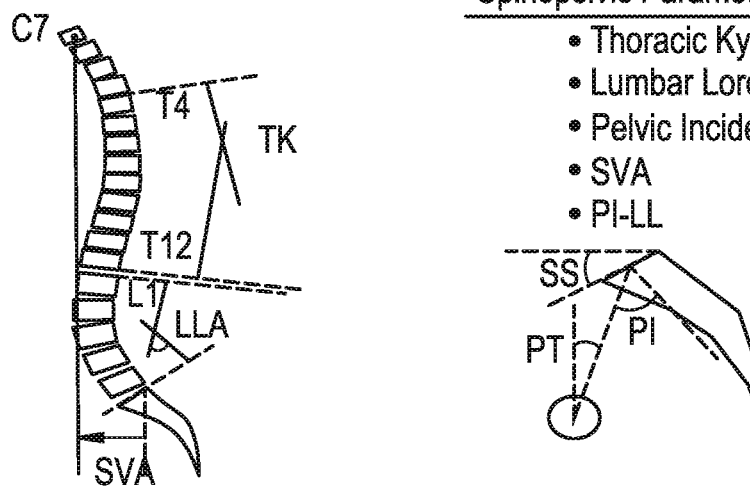
FIG. 24 is a schematic illustration of exemplary spinal regions and spinopelvic parameters.

FIG. 23 is a schematic illustration of an exemplary system 300 for measuring anatomical position and/or orientation. As shown, the system can include one or more sensors 302 of the type described herein, a computer system 304 with an electronic display (e.g., a tablet computer, a laptop computer, a mobile device, or the like), and a software application executed by the computer system. The software application can receive user inputs via, e.g., a keyboard, touchscreen display, etc. and can display various information to a user using a graphical user interface 306, such as data received from the sensors or information calculated using such data. The system can be configured to measure and/or calculate various anatomical parameters, including the various spinopelvic parameters shown in FIG. 24, such as thoracic kyphosis (TK), lumbar lordotic angle (LLA), sagittal vertical axis (SVA), sacral slope (SS), pelvic tilt (PT), and pelvic incidence (PI).

Figures 25A, 25B:
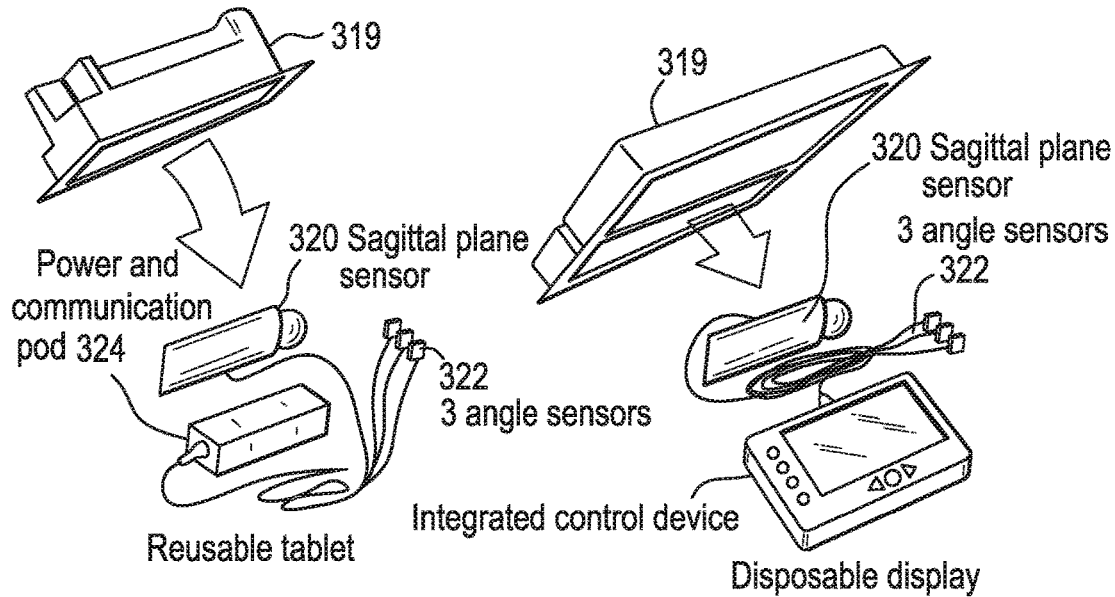
FIG. 25A is a schematic illustration of various embodiments of a display according to the teachings provided herein.
FIG. 25B is a schematic illustration of various embodiments of surgical system components according to the teachings provided herein.

An exemplary method of using the system 300 is shown schematically in FIGS. 25A-25H. FIG. 25A illustrates initial setup of the system 300 for embodiments that make use of a reusable tablet 310 and a disposable display 312. One distinction between the two versions can be that a reusable tablet 310 may not be sterile and, as a result, can communicate wirelessly with one or more sensors 314 that are sterilized and provided in sterile packaging. In the disposable display embodiment 312, all components can be sterilized and wired connections between the display and sensors can be employed because all components can be brought into the sterile field.

FIG. 25B illustrates removal of the various system components from a sterile packaging 319. As shown, the system can include a reference plane sensor 320 and one or more angle sensors 322. The system can also include a power and communication pod 324 which can be coupled to a reusable tablet or other computer system, or to a disposable computer system. The sensors 322 can be wired or wireless (e.g., Bluetooth, Wi-Fi, etc.). In the case of wired sensors, the wire size can be less than 5 mm. The sensors 322 can be approximately dime-sized, e.g., less than about 18 mm in diameter or width. Low profile sensors 322 can be used, for example sensors having a width less than 7 mm and a length less than 10 mm. In some embodiments, the sensors 322 do not include a housing, display, buttons, etc. It will be appreciated that sensors 322 and/or wires having any size can be used. The sensors 322 can be inertial measurement sensors, e.g., a 9-axis inertial measurement sensor with a gyroscope, magnetometer, and accelerometer. Other sensor types can also be used, including optical, infrared, ultrasound, RF, video tracker, video surface, fiber optic, surface RPT, laser scan, electromagnetic, combinations of sensors, and any sensors described herein.

Figure 25C:
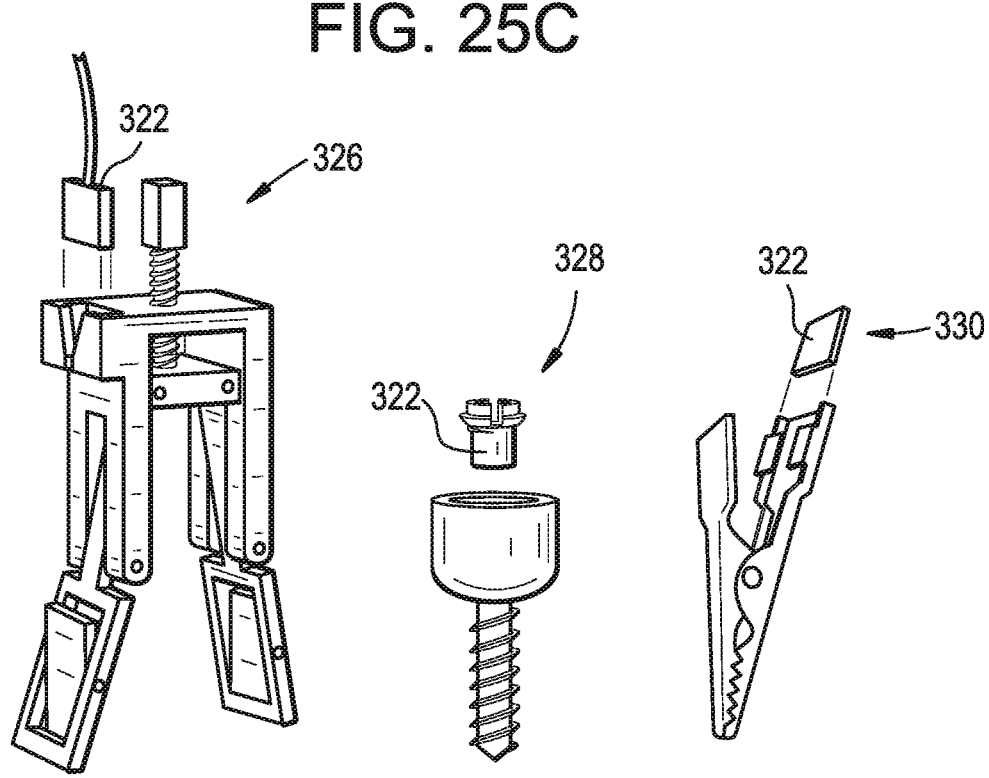
FIG. 25C is a schematic illustration of various embodiments of sensor mounts according to the teachings provided herein.

FIG. 25C illustrates various mounts for attaching the angle sensors 322 to the patient. It will be appreciated that any of the mounts disclosed above can be used instead or in addition. The illustrated mounts include a clamp 326 for attaching to the spinous process or other anatomical structure, a Steinman pin or pedicle screw 328, and an alligator clip 330. The mounts can be less than 1 inch in height in some embodiments.

Figure 25D:
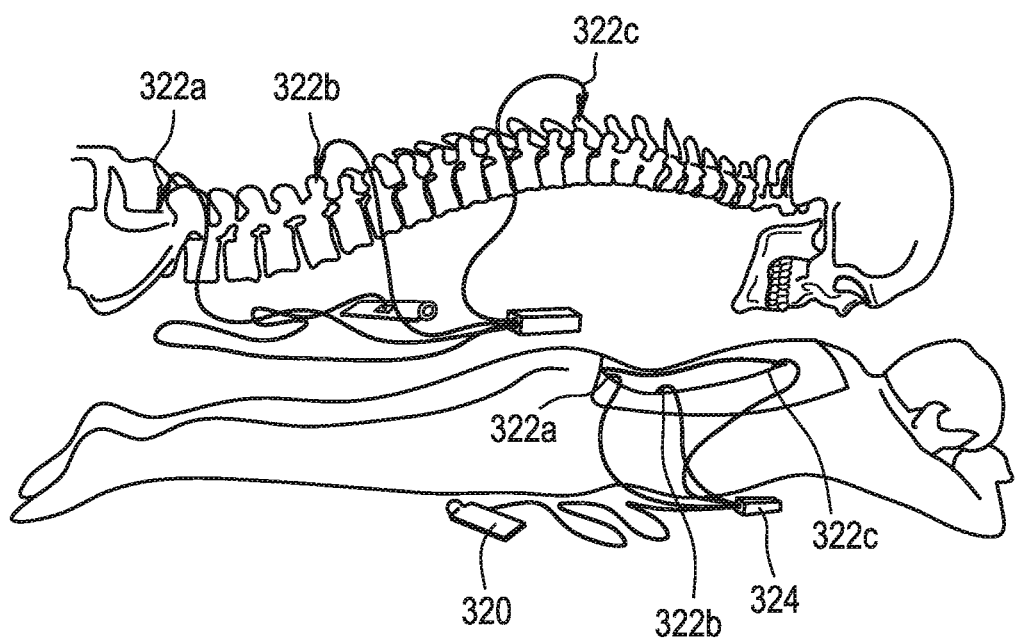
FIG. 25D is a schematic illustration of exemplary sensor placement on patient anatomy.

FIG. 25D illustrates placement of the angle sensors 322 with respect to the patient. The sensors 322 can be placed at any of a variety of locations on the patient. In an exemplary embodiment for measuring global spinal angles, such as lumbar lordosis and/or thoracic kyphosis, the sensors can be mounted in different regions of the patient's spine. For example, a sensor can be mounted at each of SI, LI, and T4 as shown by sensors 322a, 322b, and 322c. While not shown, sensors can also be mounted to the cervical spine to measure position or orientation of that region. The same or a similar arrangement of sensors can be used to measure coronal and derotation spinal angles.

Figure 25E:
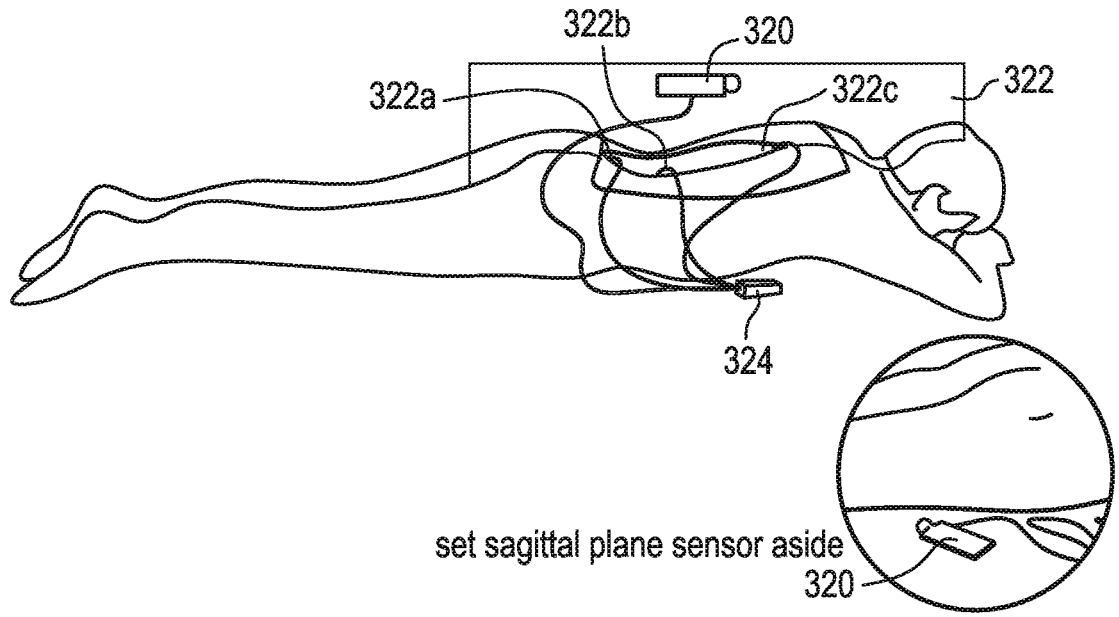
FIG. 25E is another schematic illustration of exemplary sensor placement on patient anatomy.

FIG. 25E illustrates establishment of a reference plane 332 (e.g., the sagittal plane of the patient) using the reference plane sensor 320. The reference plane sensor 320 can be the same as the angle sensors 322, and can include any of the same features as the angle sensors. The reference plane sensor 320 can include reference markings or indicia to guide a user in aligning the sensor with the patient. For example, a housing of the sensor can be human-shaped, or can include head and feet markings to indicate proper orientation. The housing can include a flat surface to allow the housing to be laid against the patient or the operating table. The housing can include a longitudinal line indicator configured to be aligned by the user with the patient's sagittal plane. In use, the user can position the reference plane sensor 320 in alignment with the patient's sagittal plane and push a button on the sensor to establish the current sensor position as the reference plane. The sagittal plane of the patient can move during the course of a surgery, especially in scoliosis and other cases where significant correction is performed. Accordingly, at any time the user desires, the reference plane 332 can be re-established by picking up the sensor 320, aligning it, and pushing the button to capture the current position as the reference plane.

Figure 25F:
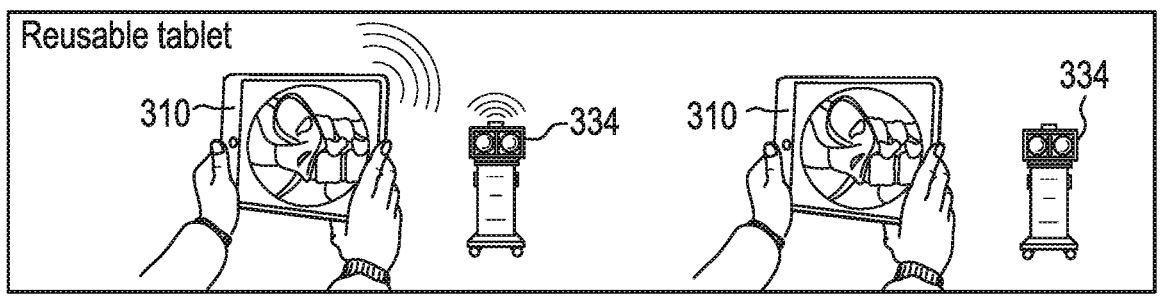
FIG. 25F is a schematic illustration of various embodiments of image capture according to the teachings provided herein.
Figure 25F:
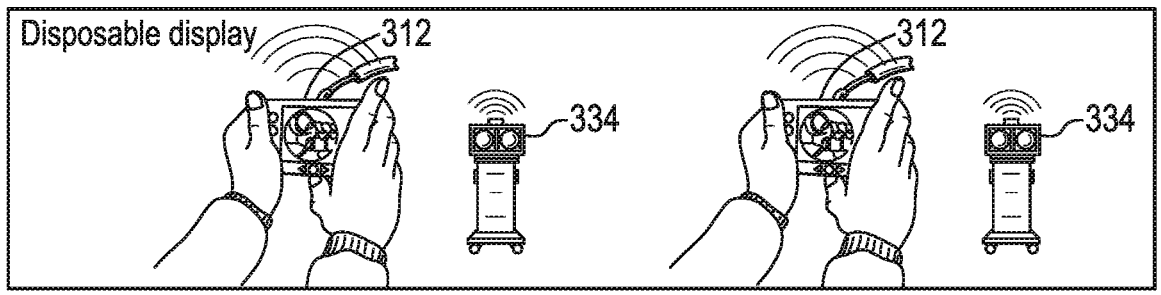

FIG. 25F illustrates capture of patient and sensor images. The images can be captured from a lateral perspective as shown. The image can be captured using fluoroscopy, MM, CT, or other imaging techniques. The captured image can be communicated to the software application executing on the computer system 304 (e.g., tablet 310). For example, an image capture device 334 used to capture the image can be integrated with the computer system 304 or can be coupled thereto (e.g., via a wireless or USB connection). The image can also be communicated using a camera of the computer system 304 to capture an image of a display screen on which the patient image is shown. For example, the integrated camera on the tablet computer 310 can be used to take a picture of the display screen of a fluoroscope to load the patient image into the tablet computer. The angle sensors 322 can be radiopaque, magnetic, metallic, or can have other properties that allow them to be visualized in the patient image. It will be appreciated that, in the case of fluoroscopy, only a small number of fluoro-shots are needed to capture an image of the sensors and of the patient anatomy (e.g., less than 3 shots, less than 2 shots, and/or a single shot in certain embodiments).

Figure 25G:
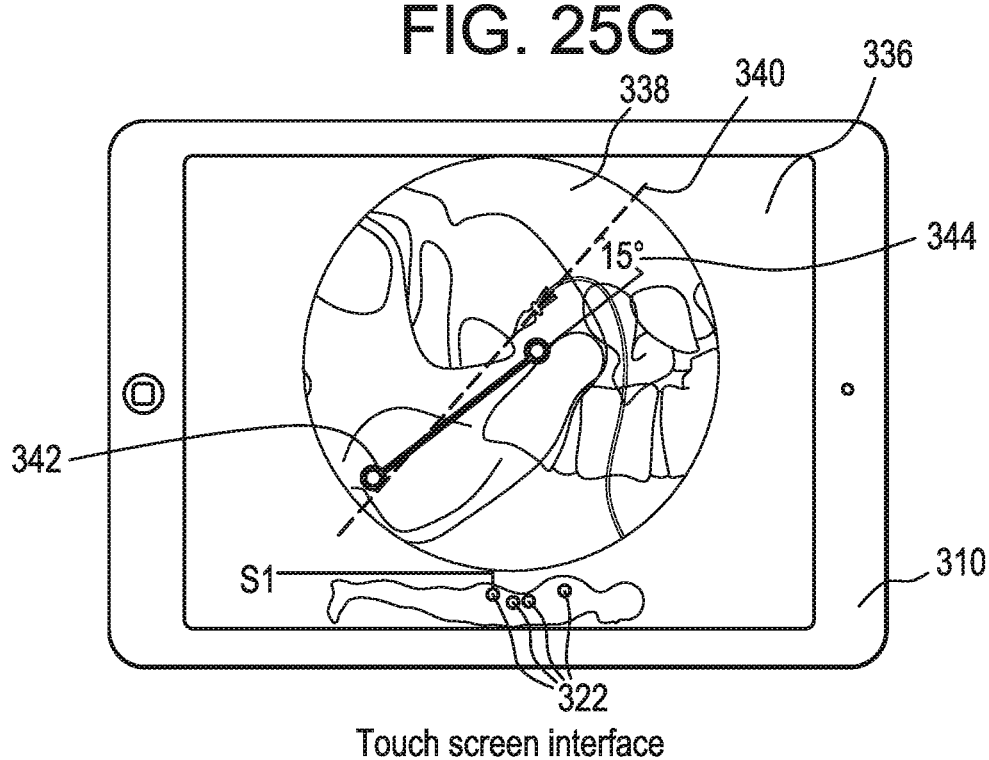
FIG. 25G is a schematic illustration of one embodiment of a graphical user interface.

In some cases, a user might position the angle sensors 322 such that their sensor axis is slightly offset from the endplate plane of the patient's vertebrae. The system can be configured to apply a correction such that angles or other measurements made by the angle sensors 322 can be calculated relative to the endplates. FIG. 25G illustrates an endplate definition step. As shown, an electronic display 336 of the computer system 304 (e.g., tablet 310) can display the captured patient image 338, showing the angle sensors 322. The computer system 304 can execute an image processing routine to identify the angle sensors 322 within the image 338 and to display a visual indicator 340 of the sensor axis to the user (a dotted line in the illustrated example). The user can then interact with the computer system 304, e.g., using a touch screen, mouse, or other input device, to draw a line parallel to the vertebral endplate 342 (a solid line with circular endpoints in the illustrated example). The computer system 304 can then calculate an angular offset between the sensor axis 340 and the user-input endplate plane 342 to determine a correction factor 344 (15 degrees in the illustrated example). This process can be performed for each of the angle sensors 322. Once complete, these compensatory angles can be used along with the angles measured by the angle sensors 322 to calculate actual absolute endplate angles, including regional angles such as lumbar lordosis, thoracic kyphosis, etc. The system can also track changes in such angles. The same or a similar approach can be used to determine coronal and/or axial angles, e.g., to obtain six degree-of-freedom information of the three-dimensional spine.

Figure 25H:
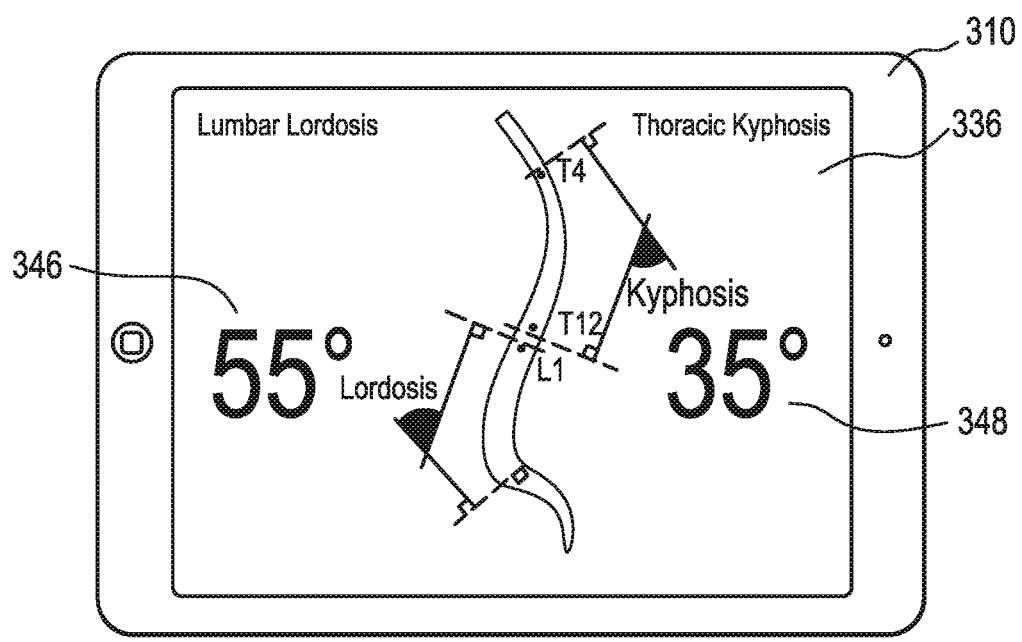
FIG. 25H is a schematic illustration of another embodiment of a graphical user interface.

FIG. 25H illustrates the system software displaying on an electronic display 336 one or more measurements captured using the system. For example, the system can display the absolute lumbar lordosis angle 346 and the absolute thoracic kyphosis angle 348 as shown. The system can also display other spinopelvic parameters, such as pelvic incidence, pelvic tilt, sagittal vertical axis, PI-LL, and so forth. The system can also display changes in any of these parameters. The system can display these measurements in real-time as the surgery is performed and as any corrections are applied to the patient's spine.

In some embodiments, measurement of certain spinopelvic parameters can allow for calculation of others. For example, the following formulas can be used to calculate pelvic tilt and sagittal vertical axis:

$$PT=1.14+0.71\times(PI)-0.52\times(\text{maximal lumbar lordosis})-0.19\times(\text{maximal thoracic kyphosis})$$

$$SVA=-52.87+5.90\times(PI)-5.13\times(\text{maximal lumbar lordosis})-4.45\times(PT)-2.09\times(\text{maximal thoracic kyphosis})+0.513\times(\text{patient age})$$

Figure 26A:
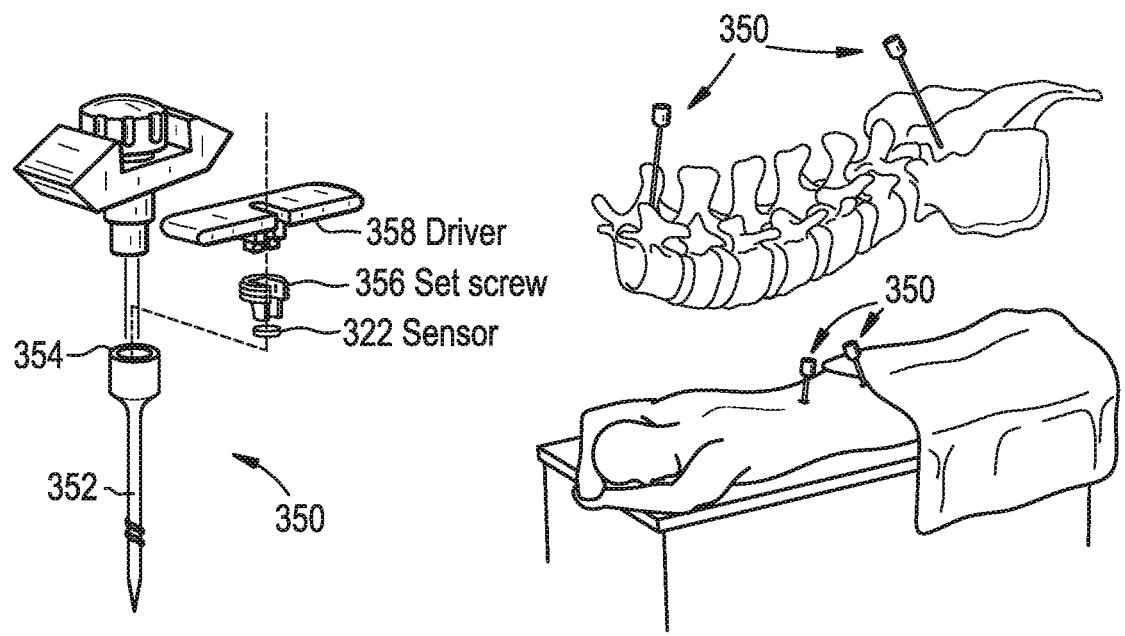
FIG. 26A is a schematic illustration of one embodiment of sensors mounted percutaneously to patient anatomy.

The system 300 can be used in any type of surgery, including open surgery and percutaneous or minimally-invasive surgery (MIS). As shown in FIG. 26A, the angle sensors 322 can be attached to the patient using percutaneous mounts 350 in some embodiments. Each mount 350 can include an elongate needle portion 352 that can be docked into vertebral bone of the patient to support the mount and attach the mount to the patient anatomy. A proximal end of the mount can include a recess 354 that can receive a sensor 322 and a set screw 356. The mount 350 can be selectively mated to a driver 358 to facilitate application of a rotational torque to the set screw 356 and/or to the mount 350 itself. The mount 350 can thus serve as a modular instrument for degenerative and MIS procedures, allowing for global alignment and measurement via a percutaneous approach.

Figure 26B:
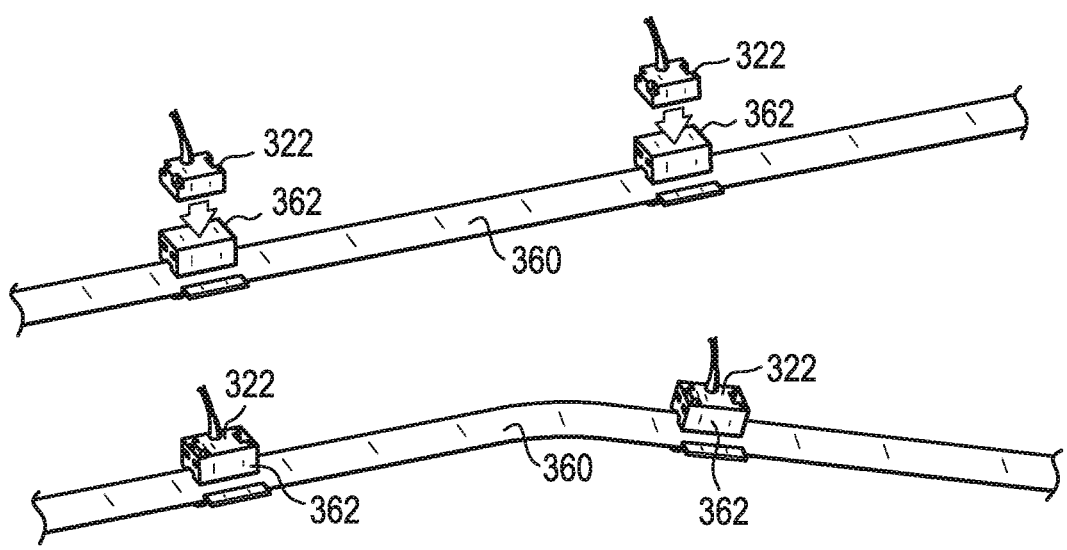
FIG. 26B is a schematic illustration of one embodiment of sensors mounted to a spinal fixation element.
Figure 26C:
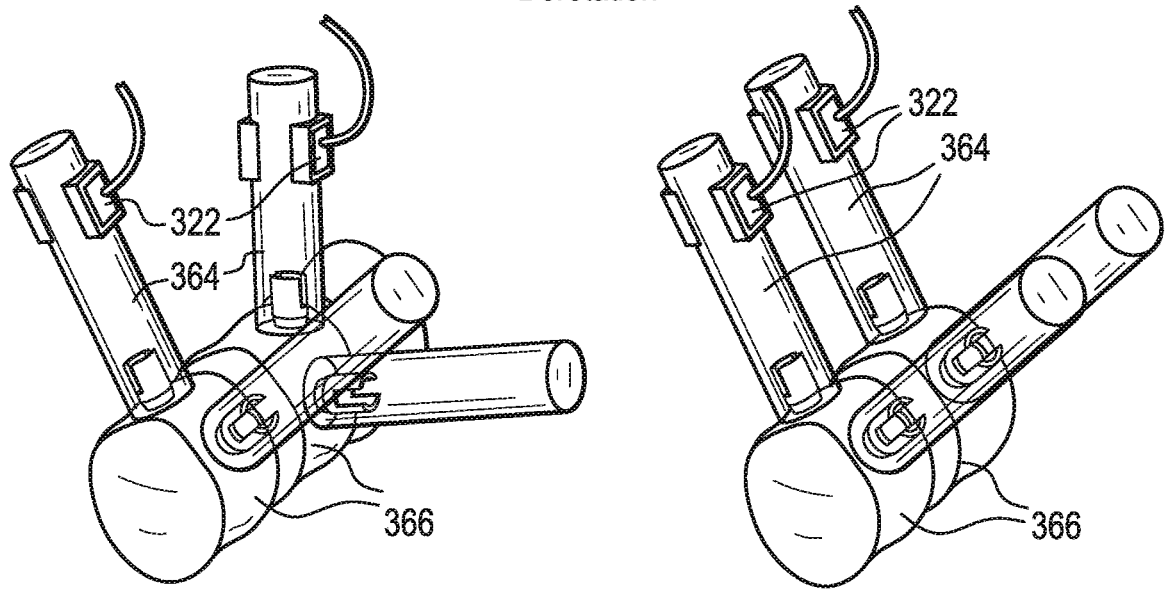
FIG. 26C is a schematic illustration of one embodiment of sensors mounted to derotation instruments.
Figure 26D:
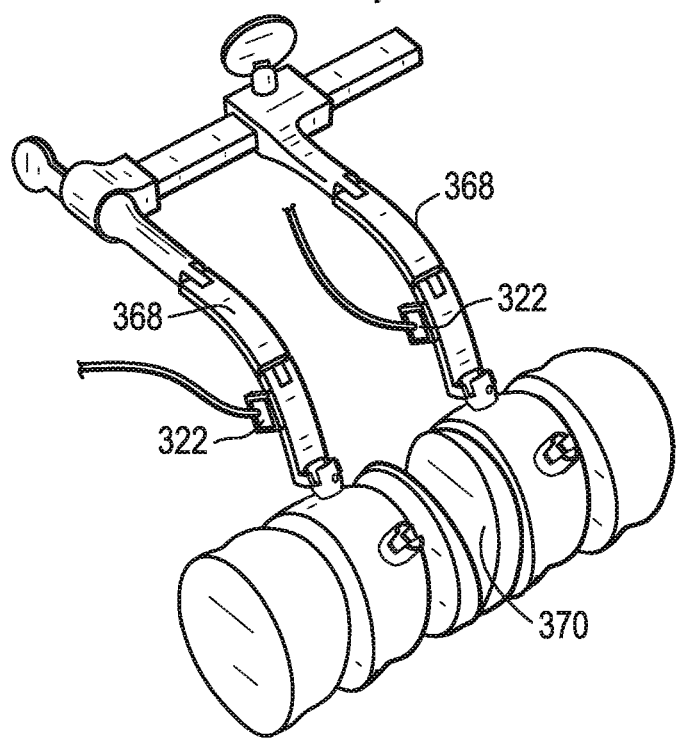
FIG. 26D is a schematic illustration of one embodiment of sensors mounted to an osteotomy closure instrument.

While use of the system is described above in the context of measuring various absolute spinal angles, it will be appreciated that the system can be used in any of a variety of other applications. For example, as shown in FIG. 26B, the system 300 can be used to measure a bend angle of a spinal rod 360 or other implant by coupling the angle sensors 322 thereto using clamps or other attachment mechanisms 362. As shown in FIG. 26C, the system 300 can also be used to measure a correction or change in position associated with a derotation maneuver, for example by coupling the angle sensors 322 to bone anchors, extension tabs, quick sticks, or other implants or instrumentation 364 attached to the vertebrae 366 being corrected. As shown in FIG. 26D, the system 300 can measure an osteotomy angle by attaching the angle sensors 322 to bone anchors, osteotomy frames, osteotomy clamps, or other implants or instrumentation 368 attached on either side of an osteotomy 370.

Figure 27A:
FIG. 27A is a schematic illustration of one embodiment of a graphical user interface showing pre-operative measurements.

FIGS. 27A-27J illustrate exemplary software functionality of the system, e.g., as implemented using a software application executing on a computer system 304 comprising a processor and a memory. As shown in FIG. 27A, the system can include a patient information module 380 for receiving user information relating to the patient and for displaying information related to the patient. The patient information module can facilitate entry and/or display of various attributes of the patient, including name, age, sex, pre-operative anatomical measurements, notes, patient images, and so forth. The patient input module can display a graphical representation 382 or an actual image of the patient's spine. Entered information can be saved to a storage unit or database of the computer system.

Figure 27B:
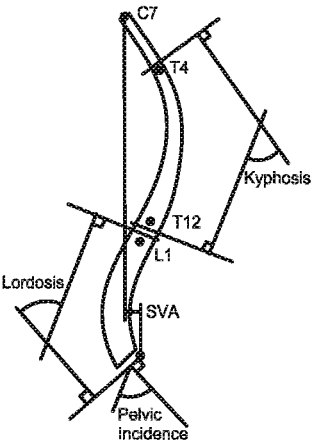
FIG. 27B is a schematic illustration of one embodiment of a graphical user interface showing user selection.

As shown in FIG. 27B, the system can support use with multiple patients, and can include a patient selection screen 384 for selecting the current patient.

Figure 27C:
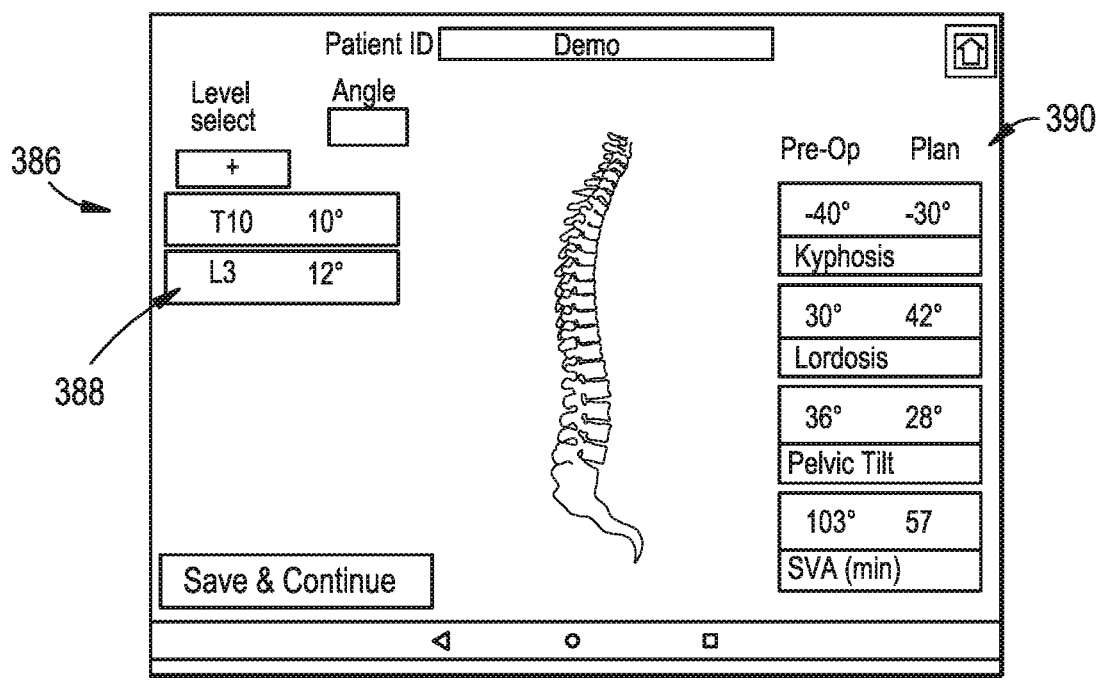
FIG. 27C is a schematic illustration of one embodiment of a graphical user interface showing pre-operative measurements and correction targets.

As shown in FIG. 27C, the system can include a planning module 386. The planning module 386 can permit entry of pre-operative planned corrections 388 and can calculate and display a predictive post-operative estimate 390. For example, a correction can be entered by specifying one or more locations (e.g., T10 and L3 as shown at ref. no. 388) and a correction angle to be performed at each level, for example via osteotomy. Based on the entered correction information, the system can calculate and display a predictive post-operative estimate 390. In the illustrated embodiment, a 10-degree correction at T10 and a 12 degree correction at L3 are estimated to result in a −30-degree post-operative kyphosis angle as compared to a −40-degree pre-operative kyphosis angle, a 42-degree post-operative lordosis angle as compared to a 30-degree pre-operative lordosis angle, a 28-degree post-operative pelvic tilt as compared to a 36-degree pre-operative pelvic tilt, and a 57 mm post-operative sagittal vertical axis (SVA) as compared to a 103 mm pre-op SVA. The user can continue entering or editing proposed corrections until the desired post-operative geometry is displayed, thereby establishing a surgical plan.

Figure 27D:
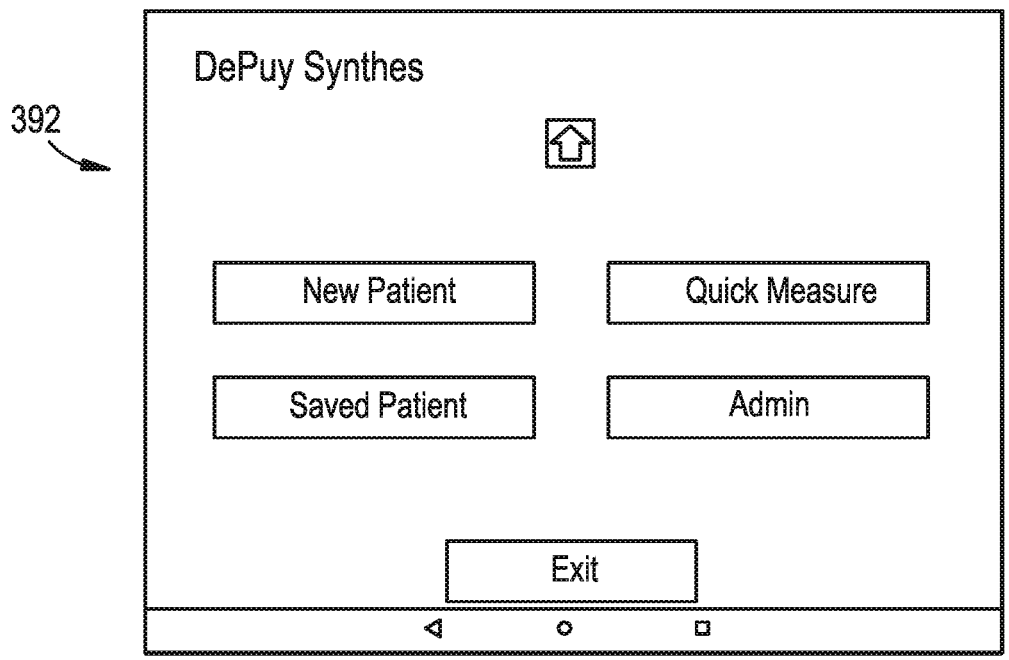
FIG. 27D is a schematic illustration of one embodiment of a graphical user interface menu.

As shown in FIG. 27D, the system can include a main menu screen 392 from which a user can begin a new procedure, recall a saved procedure, perform a quick measurement, change or view administrative settings, or exit the software application.

Figure 27E:
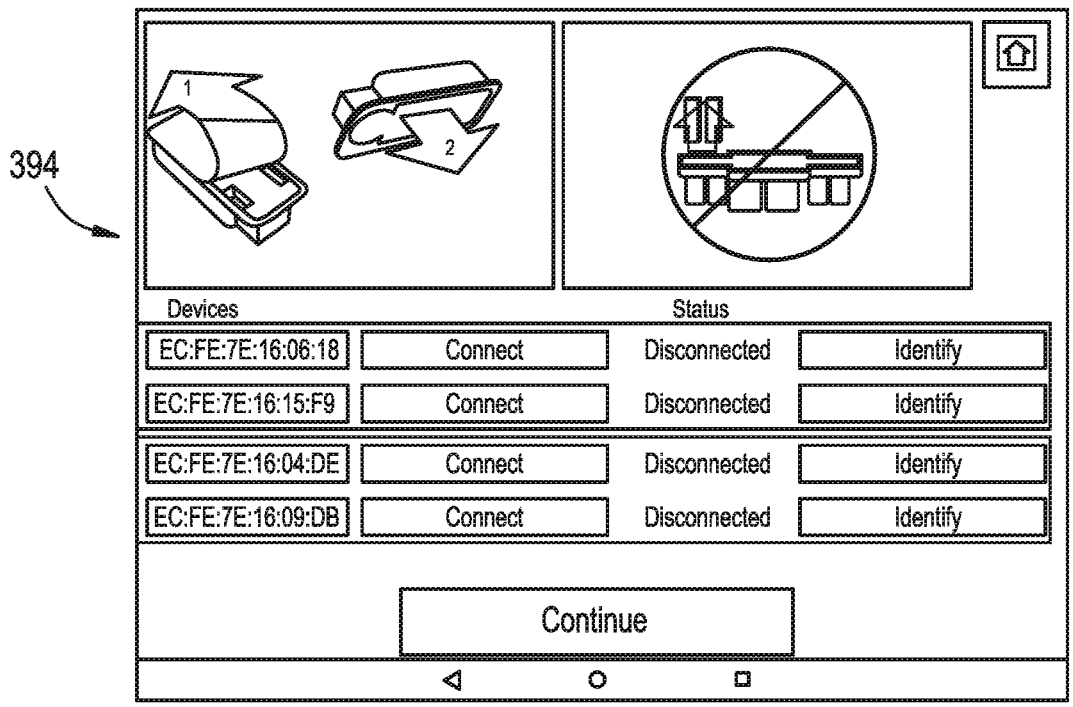
FIG. 27E is a schematic illustration of one embodiment of a graphical user interface showing instructions for sensor activation.

As shown in FIG. 27E, the system can include a sensor connection module 394. The sensor connection module 394 can display the connection status of the various sensors 320, 322 of the system to the software application and other information such as the MAC address or other identifier associated with the sensor. This information can be utilized by a surgeon or other user to ensure proper set-up of the system prior to use.

Figure 27F:
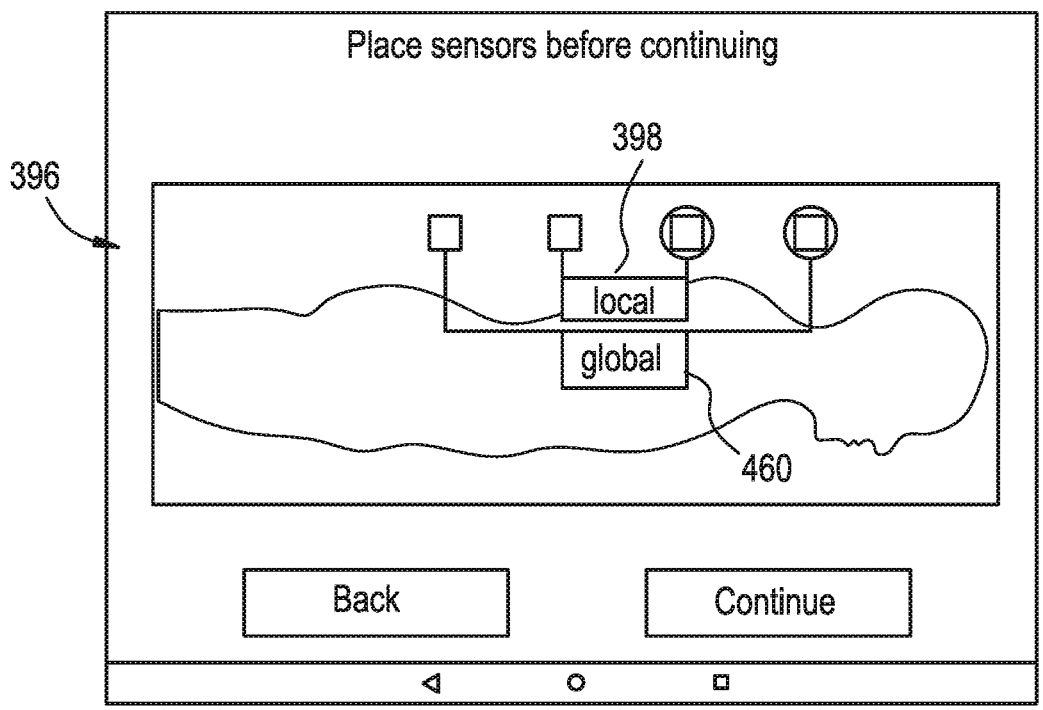
FIG. 27F is a schematic illustration of one embodiment of a graphical user interface showing instructions for sensor placement.

As shown in FIG. 27F, the system can include a sensor positioning module 396. The sensor positioning module can help guide a user in proper sensor placement. For example, the sensor positioning module 396 can control LEDs or other indicators on the sensors 322 to give the user an indication as to the use or positioning of any particular sensor. In the illustrated example, the sensor positioning module 396 can cause angle sensors for measuring a local angle to illuminate a blue (or other color) LED, and can display a color-coded graphical depiction 398 of the desired placement of the sensors relative to the patient. Similarly, the sensor positioning module 396 can cause angle sensors for measuring a global angle to illuminate a green (or other color) LED, and can display a color-coded graphical depiction 400 of the desired placement of the sensors relative to the patient.

Figure 27G:
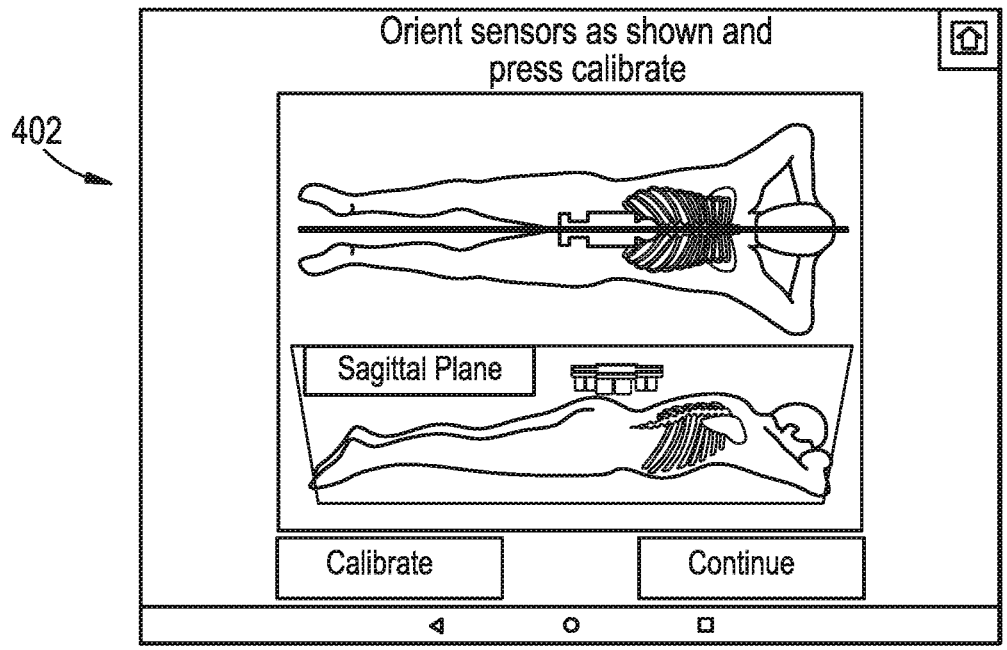
FIG. 27G is a schematic illustration of one embodiment of a graphical user interface showing instructions for sensor placement and calibration.

As shown in FIG. 27G, the system can include a reference plane calibration module 402. The reference plane calibration module can instruct the user to position the reference plane sensor 320 as shown to establish the sagittal plane of the patient (e.g., by correlating the sensor coordinate system to the patient's sagittal plane). In some embodiments, the calibration module 402 can perform a one-step calibration, in which the user simply aligns the reference plane sensor with the patient's sagittal plane and pushes a button on the sensor to establish the reference plane.

Figure 27H:
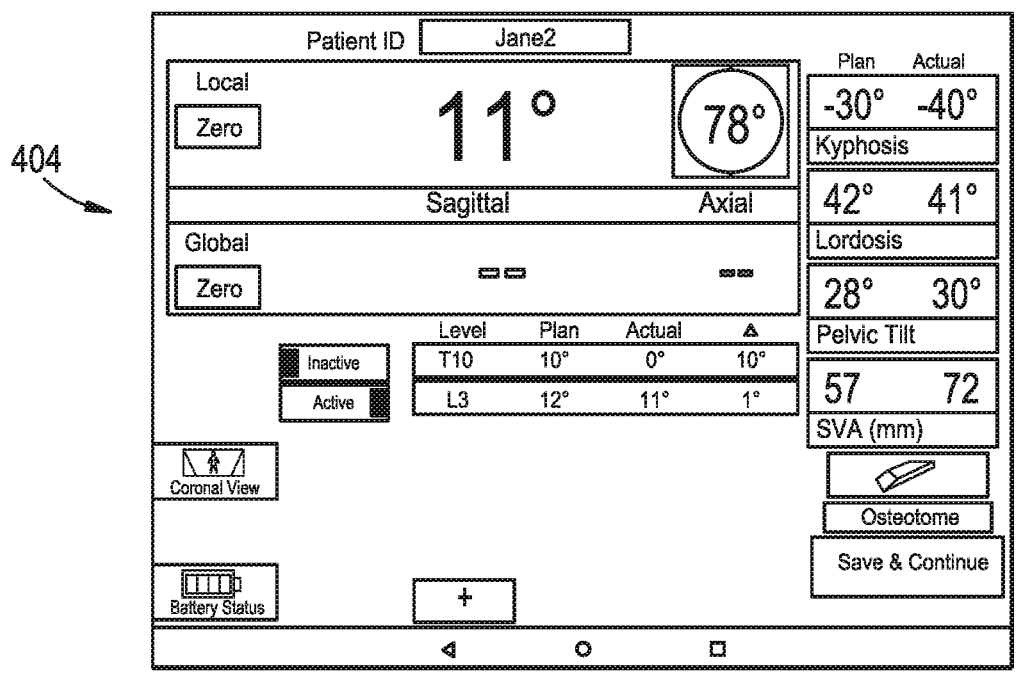
FIG. 27H is a schematic illustration of one embodiment of a graphical user interface showing intraoperative measurements.

As shown in FIG. 27H, the system can include an intuitive measurement screen 404 for various corrections, such as multi-level osteotomies as shown. The measurement screen 404 can include any of the various measured or calculated values described above, including comparisons of planned to actual values for various spinopelvic parameters.

Figure 27I:
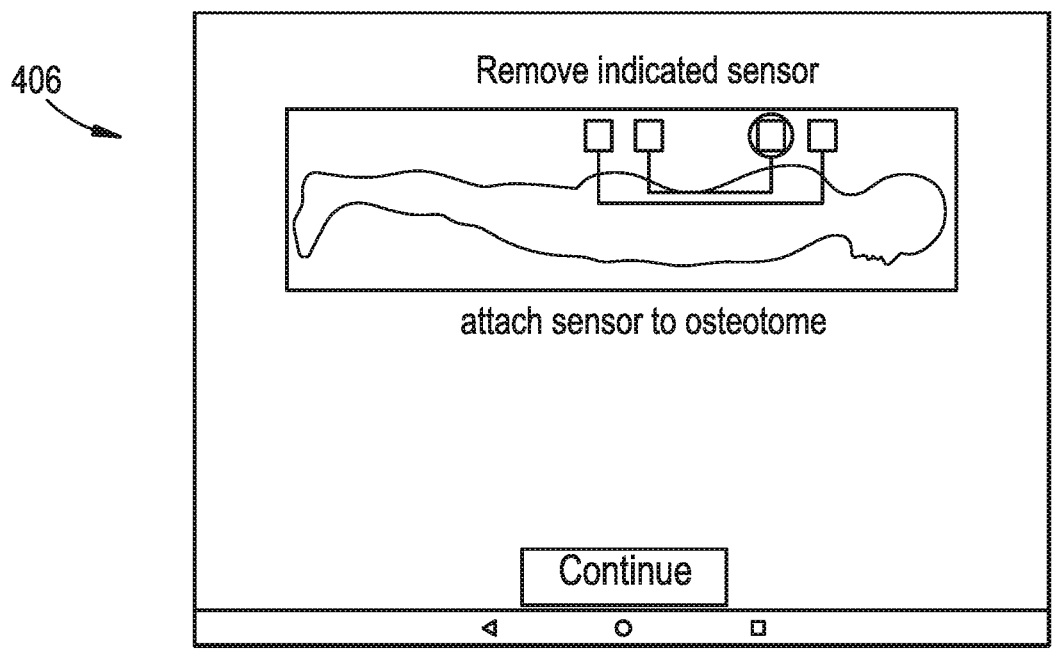
FIG. 27I is a schematic illustration of one embodiment of a graphical user interface showing instructions for relocating sensor to instrument.

As shown in FIG. 27I, the system can include an option to use one or more of the angle sensors 322 for tracking an instrument during the surgery. For example, one of the local angle sensors can be attached to an osteotome to allow a position and/or orientation of the osteotome to be measured before and during bone cutting. In such an embodiment, an instrument tracking module 406 can instruct a user regarding which sensor 322 should be detached from the patient's anatomy and coupled to the instrument to be tracked. The module 406 can further provide for designating the type of instrument being tracked such that any necessary calibration can be performed and/or data regarding the instrument loaded from a data store.

Figure 27J:
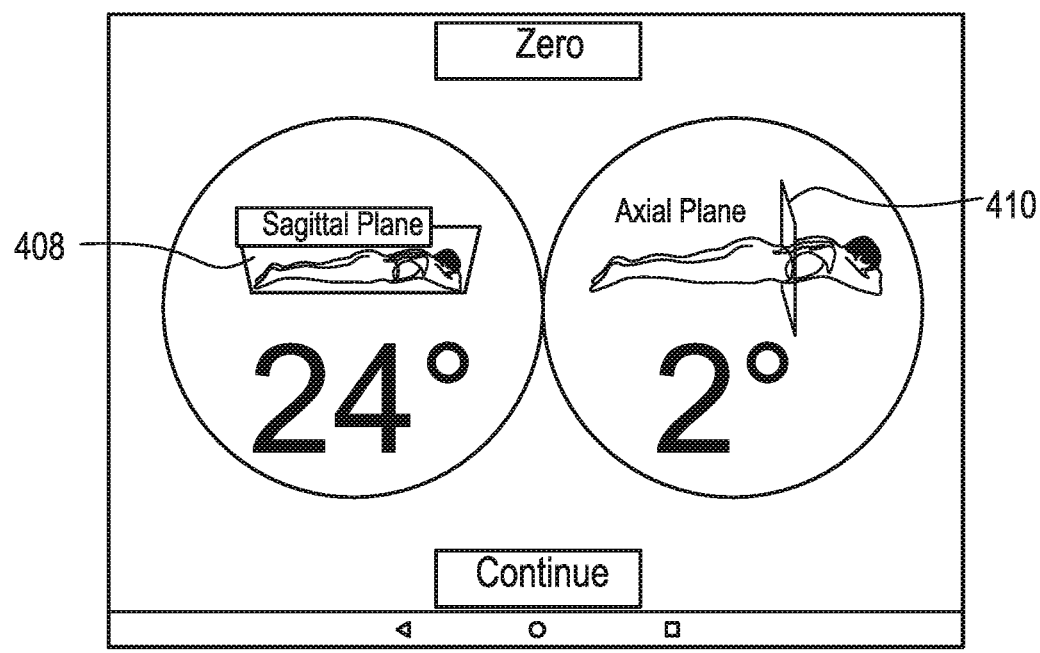
FIG. 27J is a schematic illustration of one embodiment of a graphical user interface showing intraoperative sensor measurements in two orthogonal planes.

As shown in FIG. 27J, the system can display angles measured in various planes, including, for example, sagittal plane 408 and axial plane 410 angle measurements. Accordingly, and as noted above, the system can be capable of measuring and calculating position and/or orientation data in both a reference plane and plane orthogonal to the reference plane.

The above system can be used to intraoperatively validate global spinal alignment. The system can allow continuous intraoperative monitoring, assessment, and validation of global alignment from the time a patient is placed on the operating table to the completion of the spinal deformity correction. The system can facilitate accurate and continuous intraoperative alignment validation during spinal reconstruction, which can be used to assist in measurement of the orientation of the anatomical regions of the spine prior to closing the wound when actions can still be taken to correct a less than optimal correction. The system can allow continuous validation of global spinal alignment, active real absolute value measurement of different regions of the spinal curve including thoracic kyphosis, lumbar lordosis, scoliosis and axial derotation, maintain association between standing and prone global alignment, allow spinopelvic parameter estimation, reduce wound exposure time, reduce number of steps, reduce setup errors, reduce frustration, improve speed, and enable ease of use. The system can allow segmental and global validation, measure sagittal, axial, and coronal angles, minimize setup time, enable simple calibration, provide an intuitive user interface workflow, provide accurate, repeatable and reproducible results, be adaptive to multi-level correction, use sensors having a size comparable to other instruments, and use modular sensor clips.

The system can allow surgeons to estimate spinal alignment correction achieved due to patient positioning, allow surgeons to estimate sagittal balance in concurrence with vertebral derotation, allow degenerative and MIS surgeons to maintain spinal alignment during surgery, assist surgeons in spinal rod bending, derotation maneuvers, and osteotomy closures, intraoperatively measure spinal correction achieved at each regional curve (e.g., lordosis, kyphosis, and scoliosis), maintain association between standing and prone patient position, provide actual regional angular value measurements and relative monitoring of the change in values during the correction, and/or allow monitoring of sagittal balance during degenerative and MIS cases.

The system can allow for optimization of interbody cage placement in some embodiments. For example, the system can be used to measure how much an interbody cage expanded disc space or corrected an angle in real time. In the case of expandable or adjustable cages, the system can be used to inform expansion or contraction of the cage based on real-time measurement of the achieved correction. This can increase the efficiency of operations to implant such cages.

Entire setup of the system can be completed before an actual osteotomy and correction is performed. As soon as setup is complete, a surgeon or other user can measure and associate changes in sagittal balance due to patient positioning. The surgeon can re-plan execution due to any correction achieved from patient positioning. The system can track changes in actual absolute regional angles due to operative execution. The system can allow continuous validation without requiring additional fluoro-shots, which is not possible with existing systems that require new fluoro-images be captured each time sagittal balance is to be validated.

Restoration of spinal global alignment can be important in complex spinal deformity surgery. Spinal osteotomies are established surgical techniques to correct spinopelvic malalignment. Reports have demonstrated that improved sagittal spinal alignment following spinal osteotomies correlate with improved health related quality of life (HRQOL) scores. Spine osteotomies can be broadly divided into four main types: Smith-Petersen, Ponte, Pedicle Subtraction Osteotomy (PSO), and Vertebral Column Resection (VCR). The type of osteotomy used depends on both the location of the spinal deformity and on the amount of correction that is required. A spinal fusion with instrumentation may also be performed along with spine osteotomy to stabilize the spine and prevent further curvature. It is commonly reported that many times outcome of these surgeries can result in negative impact of sagittal balance resulting in disability, pain, deficient forward gaze and poor health related quality of life (HRQOL). An intraoperative monitoring of the sagittal balance can help achieve optimum outcomes when treating spinal disorders. Even when addressing problems in the coronal and axial plane, an awareness of sagittal balance can avoid future complications. Global spinal malalignment is often difficult to assess and measure during the surgery when the patient is in the prone position. However, surgery is the crucial period because it is during surgery that alignment can be corrected. Currently there is no quick way to measure sagittal balance and regional curves intraoperatively during deformity and degenerative surgeries. Current techniques include in-vivo use of many cobbled together methods including a combination of "eyeballing," experience, estimation, multiple fluoro-images, or the use of templates, wedges, or rasps to estimate spinal angular correction to facilitate intra-operative validation of the global alignment to spinal reconstruction. In some cases, the technique is to take fluoro-images, send them to a PACs system, and use the images to measure correction using a manual protractor. This technique requires the surgeon to leave the sterile field, which is not desirable and results in increased surgery time. In addition, placing that patient prone on the operating table can change their global alignment and regional curves from what has been assessed in standing pre-operative film. This change in correction due to the patient positioning can warrant a change in the original plan for the osteotomy execution.

The instruments disclosed herein can be designed to be disposed of after a single use, or they can be designed to be used multiple times. In either case, however, the instrument can be reconditioned for reuse after at least one use. Reconditioning can include any combination of the steps of disassembly of the instrument, followed by cleaning or replacement of particular pieces, and subsequent reassembly. In particular, the instrument can be disassembled, and any number of the particular pieces or parts of the instrument can be selectively replaced or removed in any combination. Upon cleaning and/or replacement of particular parts, the instrument can be reassembled for subsequent use either at a reconditioning facility, or by a surgical team immediately prior to a surgical procedure. Those skilled in the art will appreciate that reconditioning of an instrument can utilize a variety of techniques for disassembly, cleaning/replacement, and reassembly. Use of such techniques, and the resulting reconditioned instrument, are all within the scope of the present disclosure.

The instruments described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the instrument due to the materials utilized, the presence of electrical components, etc.

One skilled in the art will appreciate further features and advantages of the disclosure based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. A method of measuring an absolute spinal angle, comprising:
    coupling first and second sensors to respective first and second portions of a patient's spine;
    capturing at least one image of the first and second sensors and the patient's spine using an imaging device;
    identifying in the at least one captured image first and second vertebral endplates that define the absolute spinal angle to be measured;
    calculating, by a processor, a first compensation angle between the first endplate and the first sensor in the at least one captured image;

calculating, by a processor, a second compensation angle between the second endplate and the second sensor in the at least one captured image;

obtaining a relative angle measured between the first and second sensors;

adjusting, by a processor, the relative angle based on the first and second compensation angles to calculate the absolute spinal angle; and communicating the absolute spinal angle to a user.

2. The method of claim 1, wherein the absolute spinal angle is calculated and communicated to the user in real-time or substantially in real-time.

3. The method of claim 1, wherein the absolute spinal angle is at least one of lumbar lordosis and thoracic kyphosis.

4. The method of claim 1, wherein communicating the absolute spinal angle comprises displaying the angle on an electronic display.

5. The method of claim 1, wherein identifying the endplates comprises interacting with a graphical user interface that displays the at least one captured image to select the endplates with an input device.

6. The method of claim 1, wherein coupling the first and second sensors comprises implanting the first and second sensors in the patient.

7. The method of claim 6, wherein the first and second sensors are percutaneously implanted in the patient.

8. The method of claim 1, wherein the identifying comprises identifying first and second vertebral endplates that define the absolute spinal angle to be measured;

wherein calculating the first compensation angle comprises calculating the first compensation angle between the first endplate and the first sensor in the at least one captured image; and wherein calculating the second compensation angle comprises calculating the second compensation angle between the second endplate and the second sensor in the at least one captured image.

9. The method of claim 8, wherein the first portion is a first vertebra of the patient and the second portion is a second vertebra of the patient, the second vertebra being non-adjacent to the first vertebra.

10. The method of claim 9, wherein the absolutely spinal angle is an angle in the sagittal plane between the first vertebra and the second vertebra.

11. The method of claim 10, further comprising:

conducting a surgical angular correction of the spine along the sagittal plane to move the patient's spine to a correct position while continuously communicating the absolute spinal angle to a user.

12. The method of claim 11, further comprising:

conducting a surgical spinal fixation or stabilization procedure to secure the patient's spine in the corrected position.

13. The method of claim 1, wherein each of the first and second sensors is an inertial motion sensor including any of an accelerometer, a gyroscope, and a magnetometer.

14. The method of claim 1, comprising continuously communicating the absolute spinal angle to a user during a surgical operation to correct the angular orientation of the spine along the sagittal plane.

* * * * *